United States Patent
Pan et al.

(10) Patent No.: US 10,065,959 B2
(45) Date of Patent: Sep. 4, 2018

(54) ELECTRONIC DEVICE

(71) Applicant: Merck Patent GmbH, Darmstadt (DE)

(72) Inventors: Junyou Pan, Frankfurt am Main (DE); Amir Hossain Parham, Frankfurt am Main (DE); Rene Peter Scheurich, Gross-Zimmern (DE); Thomas Rudolph, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 395 days.

(21) Appl. No.: 14/648,409

(22) PCT Filed: Nov. 4, 2013

(86) PCT No.: PCT/EP2013/003309
§ 371 (c)(1),
(2) Date: May 29, 2015

(87) PCT Pub. No.: WO2014/082705
PCT Pub. Date: Jun. 5, 2014

(65) Prior Publication Data
US 2015/0336959 A1 Nov. 26, 2015

(30) Foreign Application Priority Data

Nov. 30, 2012 (EP) ..................... 12008039

(51) Int. Cl.
| | |
|---|---|
| *H01L 51/00* | (2006.01) |
| *C07D 487/04* | (2006.01) |
| *C07D 471/04* | (2006.01) |
| *C09B 11/28* | (2006.01) |
| *C09B 15/00* | (2006.01) |
| *C09B 17/00* | (2006.01) |
| *C09B 19/00* | (2006.01) |
| *C09B 21/00* | (2006.01) |
| *C09B 57/00* | (2006.01) |
| *C07D 235/02* | (2006.01) |
| *C07D 403/04* | (2006.01) |
| *C07D 403/14* | (2006.01) |
| *C07D 409/14* | (2006.01) |
| *C07D 413/04* | (2006.01) |
| *C07D 413/10* | (2006.01) |
| *C07D 491/048* | (2006.01) |
| *C07D 491/052* | (2006.01) |
| *C07D 495/04* | (2006.01) |
| *C07D 498/04* | (2006.01) |
| *C07D 513/04* | (2006.01) |
| *C07D 519/00* | (2006.01) |
| *H01L 51/52* | (2006.01) |
| *H01L 51/50* | (2006.01) |

(52) U.S. Cl.
CPC ......... *C07D 487/04* (2013.01); *C07D 235/02* (2013.01); *C07D 403/04* (2013.01); *C07D 403/14* (2013.01); *C07D 409/14* (2013.01); *C07D 413/04* (2013.01); *C07D 413/10* (2013.01); *C07D 471/04* (2013.01); *C07D 491/048* (2013.01); *C07D 491/052* (2013.01); *C07D 495/04* (2013.01); *C07D 498/04* (2013.01); *C07D 513/04* (2013.01); *C07D 519/00* (2013.01); *C09B 11/28* (2013.01); *C09B 15/00* (2013.01); *C09B 17/00* (2013.01); *C09B 17/005* (2013.01); *C09B 19/00* (2013.01); *C09B 21/00* (2013.01); *C09B 57/00* (2013.01); *H01L 51/0067* (2013.01); *H01L 51/0071* (2013.01); *H01L 51/0072* (2013.01); *H01L 51/5024* (2013.01); *H01L 51/5076* (2013.01); *H01L 51/5206* (2013.01); *H01L 51/5221* (2013.01); *Y02E 10/549* (2013.01)

(58) Field of Classification Search
None
See application file for complete search history.

(56) References Cited

U.S. PATENT DOCUMENTS 5,587,112 A * 12/1996 Kauffman ............ C07D 209/80
252/301.16
6,333,146 B1 12/2001 Kobayashi et al.

FOREIGN PATENT DOCUMENTS

| JP | 11144867 A | | 5/1999 | |
|---|---|---|---|---|
| JP | 2000286056 A | | 10/2000 | |
| KR | 1020130115161 | * | 1/2006 | ........... C07D 487/04 |
| WO | WO-2011/126225 A1 | | 10/2011 | |
| WO | WO 2013085339 A2 | * | 6/2013 | ........... C07D 403/04 |

OTHER PUBLICATIONS

Osman et al. "Heterocyclic compounds. VIII. Studies on oxazolophenoxazines" Can. J. Chem. 1976, 54, 37-43.*
Maisuradze et al., "Synthesis of Novel Heterocyclic Systems, Benzo[b]furobenzimidazoles", Chemistry of Heterocyclic Compounds, 2012, vol. 48, No. 7, pp. 1125-1126.
Translation of Japanese Office Action for Japanese Application No. 2015-544372, dated Oct. 3, 2017, 3 pages.

* cited by examiner

Primary Examiner — Robert S Loewe
(74) Attorney, Agent, or Firm — Kim Winston LLP

(57) ABSTRACT

The present application relates to an electronic device comprising a heteroaromatic compound of a formula (I) as functional material, in particular as electron-transport material and as matrix material for emitter compounds.

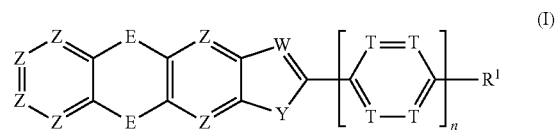

14 Claims, No Drawings

ELECTRONIC DEVICE

RELATED APPLICATIONS

This application is a national stage application, filed pursuant to 35 U.S.C. § 371, of PCT/EP2013/003309, filed Nov. 4, 2013, which claims the benefit of European Patent Application No. 12008039.5, filed Nov. 30, 2012, which is incorporated herein by reference in its entirety.

The present application relates to an electronic device which comprises at least one organic layer which in turn comprises at least one compound of the formula (I), as defined below. The compound of the formula (I) represents a functional material which is preferably employed as electron-transport material and/or as matrix material for emitter compounds in the electronic device. The invention furthermore relates to a compound of the formula (I-1) which is particularly suitable for use in an electronic device, in particular in the above-mentioned functions.

In accordance with the present invention, the term electronic device is generally taken to mean electronic devices which comprise organic materials. Such devices are also known as organic electronic devices. For the purposes of the present application, this term is preferably taken to mean OLEDs and some further embodiments of organic electronic devices which are disclosed later in the application.

The general structure and functional principle of OLEDs is known to the person skilled in the art and is described, inter alia, in U.S. Pat. Nos. 4,539,507, 5,151,629, EP 0676461 and WO 1998/27136.

Further improvements are necessary with respect to the performance data of electronic devices, in particular in view of broad commercial use, for example in displays or as light sources. Of particular importance in this connection are the lifetime, the efficiency and the operating voltage of the electronic devices and the colour values achieved in light emission.

A starting point for improving these parameters is the choice of suitable organic materials for use in the electronic devices. Through the choice of suitable materials, performance data of the electronic device can be crucially influenced.

For use as electron-transporting compounds, for example in the electron-transport layer or as matrix material in the emitting layer, a multiplicity of materials are known from the prior art.

These include, for example, LiQ, AlQ3 and other quinolinates (U.S. Pat. No. 4,356,429, US 2007/0092753), and heteroaromatic compounds, for example triazines (WO 2010/015306, WO 2007/063754 or WO 2008/056746), carbazoles (WO 2005/039246, US 2005/0069729, JP 2004/288381, EP 1205527 or WO 2008/086851), and ketones, phosphine oxides, sulfoxides and sulfones (WO 2004/093207, WO 2010/006680 or WO 2005/003253).

The prior art furthermore discloses the use of benzimidazole derivatives and similar heteroaromatic compounds as electron-transport materials and/or as matrix materials in the emitting layer of electronic devices (WO 2004/080975, US 2009/184633, JP 2008/130754 and JP 2006/156847).

However, electronic devices comprising the compounds have potential for improvement, in particular with respect to efficiency, operating voltage, lifetime and processability. Of particular importance here are lifetime and operating voltage of the electronic device.

The prior art furthermore discloses OLEDs comprising benzimidazole derivatives in which two benzimidazole groups are bonded symmetrically to one another via a central five-membered ring (WO 2011/126225). The compounds are employed in the electron-transport layer or in the emitting layer as matrix materials.

Thus, there continues to be interest in electronic devices, in particular OLEDs, having high efficiency and low operating voltage as well as a long lifetime.

Surprisingly, it has now been found that electronic devices comprising a benzimidazole derivative which carries a condensed-on heterocyclic group having an aromatic six-membered ring which is in turn condensed on have the above-mentioned properties and thus achieve the technical object.

The present invention thus relates to an electronic device comprising anode, cathode and at least one organic layer comprising at least one compound of the formula (I)

formula (I)

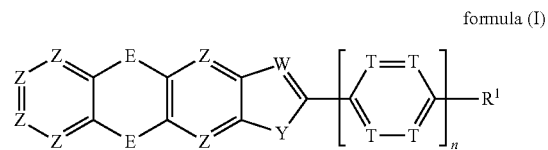

where:
E is selected on each occurrence, identically or differently, from a single bond, B(R$^1$), C=O, N(R$^1$), P(R$^1$), P(=O)R$^1$, O, S, S=O and S(=O)$_2$, where both groups E cannot be a single bond;
T is on each occurrence, identically or differently, CR$^1$ or N;
W is CR$^1$ or N;
Y is N(R$^1$), O or S;
Z is on each occurrence, identically or differently, CR$^2$ or N;
R$^1$ is on each occurrence, identically or differently, H, D, F, C(=O)R$^3$, CN, Si(R$^3$)$_3$, N(R$^3$)$_2$, P(=O)(R$^3$)$_2$, S(=O)R$^3$, S(=O)$_2$R$^3$, a straight-chain alkyl, or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO or SO$_2$ and where one or more H atoms in the above-mentioned groups may be replaced by D, F or CN, or an aromatic or heteroaromatic ring system having 5 to 30 aromatic ring atoms, which may in each case be substituted by one or more radicals R$^3$, or an aryloxy or heteroaryloxy group having 5 to 30 aromatic ring atoms, which may be substituted by one or more radicals R$^3$;
R$^2$ is on each occurrence, identically or differently, H, D, F, C(=O)R$^3$, CN, Si(R$^3$)$_3$, N(R$^3$)$_2$, P(=O)(R$^3$)$_2$, S(=O)R$^3$, S(=O)$_2$R$^3$, a straight-chain alkyl, or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, C=O, C=NR$^3$, —C(=O)O—, —C(=O)NR$^3$—, NR$^3$, P(=O)(R$^3$), —O—, —S—, SO or SO$_2$ and where one or more H atoms in the above-mentioned groups may be replaced by D, F or CN, or an aromatic or heteroaromatic ring system having 5 to 30 aromatic ring atoms, which may in each case be substituted by one or more radicals R$^3$, or an aryloxy or heteroaryloxy group having 5 to 30 aromatic ring atoms, which may be substituted by one or more radicals R$^3$, where two or more radicals R$^2$ may be linked to one another and may form an aliphatic or heteroaliphatic ring;

R$^3$ is on each occurrence, identically or differently, H, D, F, C(=O)R$^4$, CN, Si(R$^4$)$_3$, N(R$^4$)$_2$, P(=O)(R$^4$)$_2$, S(=O)R$^4$, S(=O)$_2$R$^4$, a straight-chain alkyl, or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals R$^4$ and where one or more CH$_2$ groups in the above-mentioned groups may be replaced by —R$^4$C=CR$^4$—, —C≡C—, Si(R$^4$)$_2$, C=O, C=NR$^4$, —C(=O)O—, —C(=O)NR$^4$—, NR$^4$, P(=O)(R$^4$), —O—, —S—, SO or SO$_2$ and where one or more H atoms in the above-mentioned groups may be replaced by D, F or CN, or an aromatic or heteroaromatic ring system having 5 to 30 aromatic ring atoms, which may in each case be substituted by one or more radicals R$^4$, or an aryloxy or heteroaryloxy group having 5 to 30 aromatic ring atoms, which may be substituted by one or more radicals R$^4$, where two or more radicals R$^3$ may be linked to one another and may form a ring;

R$^4$ is on each occurrence, identically or differently, H, D, F or an aliphatic, aromatic or heteroaromatic organic radical having 1 to 20 C atoms, in which, in addition, one or more H atoms may be replaced by D or F; two or more substituents R$^4$ here may be linked to one another and may form a ring;

n is equal to 0 or 1;

where at least one group R$^1$ or R$^2$ in the compound of the formula (I) is selected from an aromatic or heteroaromatic ring system having 5 to 40 aromatic ring atoms, which may be substituted by one or more radicals R$^3$.

The compounds according to the invention preferably have one or more of the advantages indicated below:

On use of the compounds according to the invention in electronic devices, high power efficiency and a low operating voltage of the devices can be achieved.

On use of the compounds according to the invention, high stability or a long lifetime of the electronic device is obtained.

The compounds according to the invention have significantly better solubility and film-formation properties compared with materials known from the prior art, in particular compared with matrix materials having a carbazole skeleton.

General definitions of chemical groups follow:

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an spa-hybridised C, Si, N or O atom, an sp$^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following scheme:

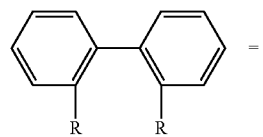

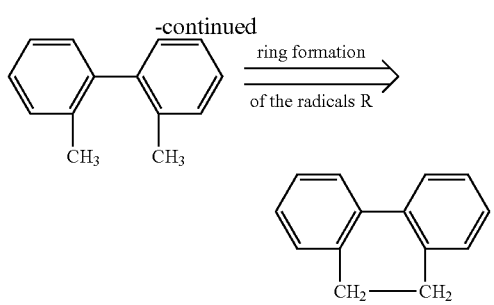

Furthermore, however, the above-mentioned formulation is also intended to be taken to mean that, in the case where one of the two radicals represents hydrogen, the second radical is bonded at the position to which the hydrogen atom was bonded, with formation of a ring. This is illustrated by the following scheme:

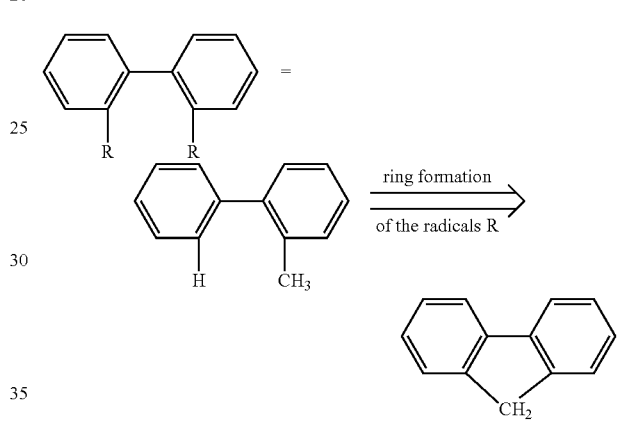

According to a preferred embodiment, at least one group $R^1$ in the compound of the formula (I) is selected from an aromatic or heteroaromatic ring system having 5 to 40 aromatic ring atoms, which may be substituted by one or more radicals $R^3$.

According to a particularly preferred embodiment, at least one group $R^1$ or $R^2$, preferably at least one group $R^1$, in the compound of the formula (I) is selected from a group containing at least one of the following groups:

heteroaryl groups having 5 to 20 aromatic ring atoms which contain at least one heteroaromatic five-membered ring having two or more heteroatoms selected from N, O and S;

heteroaryl groups having 6 to 20 aromatic ring atoms which contain at least one heteroaromatic six-membered ring having one or more heteroatoms selected from N, O and S; and carbazole groups.

Carbazole groups here are also taken to mean carbazole derivatives containing condensed-on groups, such as, for example, indenocarbazoles or indolocarbazoles, as well as carbazole derivatives in which one or more carbon atoms in the aromatic six-membered rings have been replaced by nitrogen.

Furthermore preferably, at least one group $R^1$ or $R^2$ in the compound of the formula (I), particularly preferably at least one group $R^1$, is selected from groups of the formulae (Het-a) to (Het-e)

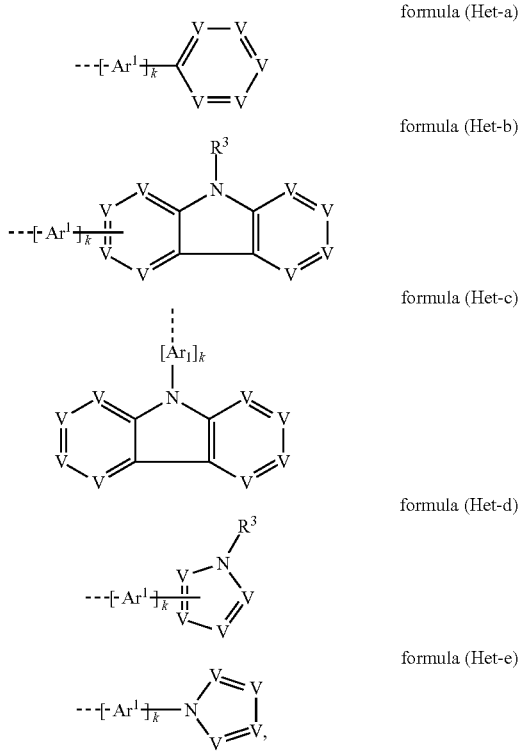

formula (Het-a)

formula (Het-b)

formula (Het-c)

formula (Het-d)

formula (Het-e)

where
Ar¹ is an aromatic or heteroaromatic ring system having 5 to 20 aromatic ring atoms, which may be substituted by one or more radicals $R^3$;
V is on each occurrence, identically or differently, N or $CR^3$;
k is equal to 0 or 1;
and the dashed line denotes the bond to the remainder of the compound;
and where at least one group V in the ring in formula (Het-a), (Het-d) and (Het-e) is equal to N.

According to a preferred embodiment, the compound of the formula (I) has a molecular weight of 250 to 1500 Da, particularly preferably 275 to 1250 Da and very particularly preferably 300 to 1000 Da.

According to a further preferred embodiment, the compound of the formula (I) is asymmetrical, particularly preferably asymmetrical in that it is asymmetrical with respect to any desired mirror plane which is perpendicular to the paper plane. This has the advantage that the compound has better solubility. Furthermore and preferably in combination with the above-mentioned advantage, this has the advantage that the compounds have a higher T1 level.

According to a preferred embodiment, n is equal to 1.

It is furthermore preferred for not more than three groups T in the formula (I) to be equal to N. Furthermore preferably, not more than two adjacent groups T are equal to N. Particularly preferably, all groups T are equal to $CR^1$.

It is furthermore preferred for not more than three groups Z per ring in the formula (I) to be equal to N. Furthermore preferably, not more than two adjacent groups Z are equal to N. Particularly preferably, all groups Z are equal to $CR^2$.

W is furthermore preferably equal to $CR^1$.

E is furthermore preferably on each occurrence, identically or differently, a single bond, C=O, N($R^1$), O, S, S=O or S($=$O)$_2$, where both groups E cannot be a single bond.

$R^1$ is preferably on each occurrence, identically or differently, H, D, CN, Si($R^3$)$_3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —$R^3$C=C$R^3$—, —C≡C—, Si($R^3$)$_2$, C=O, C=N$R^3$, —C(=O)O—, —C(=O)N$R^3$—, N$R^3$, P(=O)($R^3$), —O—, —S—, SO or SO$_2$ and where one or more H atoms in the above-mentioned groups may be replaced by D, F or CN, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$;

$R^1$ is particularly preferably on each occurrence, identically or differently, H, D, a straight-chain alkyl group having 1 to 10 C atoms or a branched or cyclic alkyl group having 3 to 10 C atoms, where the alkyl groups may each be substituted by one or more radicals $R^3$, or an aromatic or heteroaromatic ring system having 6 to 24 aromatic ring atoms, which may be substituted by one or more radicals $R^3$.

It is preferred for no ring formation to be present between two or more radicals $R^2$.

$R^2$ is preferably on each occurrence, identically or differently, H, D, CN, Si($R^3$)$_3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^3$ and where one or more CH$_2$ groups in the above-mentioned groups may be replaced by —$R^3$C=C$R^3$—, —C≡C—, Si($R^3$)$_2$, C=O, C=N$R^3$, —C(=O)O—, —C(=O)N$R^3$—, N$R^3$, P(=O)($R^3$), —O—, —S—, SO or SO$_2$ and where one or more H atoms in the above-mentioned groups may be replaced by D, F or CN, or an aromatic or heteroaromatic ring system having 5 to 30 aromatic ring atoms, which may in each case be substituted by one or more radicals $R^3$, or an aryloxy or heteroaryloxy group having 5 to 30 aromatic ring atoms, which may be substituted by one or more radicals $R^3$;

$R^2$ is particularly preferably on each occurrence, identically or differently, H, D, a straight-chain alkyl group having 1 to 10 C atoms or a branched or cyclic alkyl group having 3 to 10 C atoms, where the alkyl groups may each be substituted by one or more radicals $R^3$, or an aromatic or heteroaromatic ring system having 6 to 24 aromatic ring atoms, which may be substituted by one or more radicals $R^3$.

$R^3$ is preferably on each occurrence, identically or differently, H, D, CN, Si($R^4$)$_3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, where the above-mentioned groups may each be substituted by one or more radicals $R^4$ and where one or more CH$_2$ groups in the above-mentioned groups may be replaced by —$R^4$C=C$R^4$—, —C≡C—, Si($R^4$)$_2$, C=O, C=N$R^4$, —C(=O)O—, —C(=O)—N$R^4$—, N$R^4$, P(=O)($R^4$), —O—, —S—, SO or SO$_2$ and where one or more H atoms in the above-mentioned groups may be replaced by D, F or CN, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which may be substituted by one or more radicals $R^4$;

$R^3$ is particularly preferably on each occurrence, identically or differently, H, D, a straight-chain alkyl group having 1 to 10 C atoms or a branched or cyclic alkyl group having 3 to 10 C atoms, where the alkyl groups may each be substituted by one or more radicals $R^4$, or an aromatic or heteroaromatic ring system having 6 to 24 aromatic ring atoms, which may be substituted by one or more radicals $R^4$.

Preferred embodiments of compounds of the formula (I) conform to the following formulae (I-A) to (I-F)

formula (I-A)

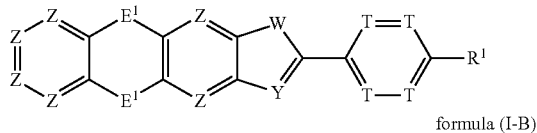

formula (I-B)

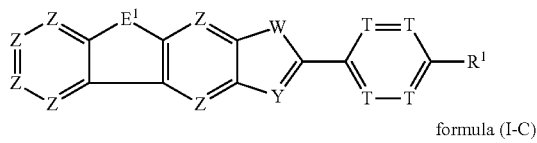

formula (I-C)

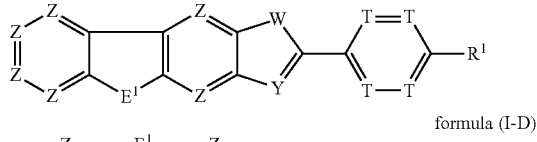

formula (I-D)

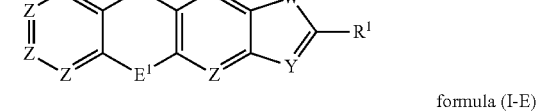

formula (I-E)

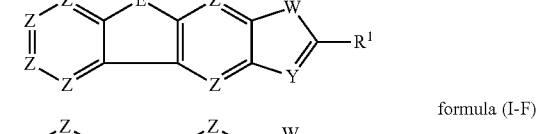

formula (I-F)

where
$E^1$ is selected on each occurrence, identically or differently, from C=O, N($R^1$), O and S; and
where the remaining symbols occurring are defined as above; and
where at least one group $R^1$ or $R^2$ in the compound of the formulae (I-A) to (I-F) is selected from an aromatic or heteroaromatic ring system having 5 to 40 aromatic ring atoms, which may be substituted by one or more radicals $R^3$.

The above-mentioned preferred embodiments of the symbols are also regarded as preferred for the formulae (I-A9 to (I-F).

For the formulae (I-A) to (I-F), T is especially preferably equal to $CR^1$.

Furthermore, for the formulae (I-A) to (I-F), Z is especially preferably equal to $CR^1$.

Furthermore, for the formulae (I-A) to (I-F), W is especially preferably equal to N.

Furthermore, at least one group $R^1$ or $R^2$, preferably at least one group $R^1$ in the compound of the formulae (I-A) to (I-F) is especially preferably selected from a group containing at least one of the following groups:

heteroaryl groups having 5 to 20 aromatic ring atoms which contain at least one heteroaromatic five-membered ring having two or more heteroatoms selected from N, O and S;
heteroaryl groups having 6 to 20 aromatic ring atoms which contain at least one heteroaromatic six-membered ring having one or more heteroatoms selected from N, O and S; and
carbazole groups.

The invention furthermore relates to a compound of the formula (I-1), which represents a specific embodiment of the formula (I):

formula (I-1)

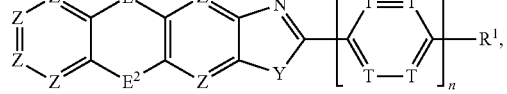

where:
$E^2$ is on each occurrence, identically or differently, a single bond, C=O, N($R^1$), O or S, where both groups $E^2$ cannot be a single bond;
the remaining symbols are defined as above;
and where at least one group $R^1$ is selected from groups of the formulae (Het-a) to (Het-e), as defined above.

The above-mentioned preferred embodiments of the symbols are likewise regarded as preferred for formula (I-1).

For formula (I-1), T is especially preferably equal to $CR^1$.

Furthermore, for formula (I-1), Z is especially preferably equal to $CR^1$.

Furthermore, for formula (I-1), Y is especially preferably equal to $NR^1$.

For formula (I-1), $E^2$ is preferably on each occurrence, identically or differently, a single bond, $NR^1$, O, or S, where both $E^2$ cannot be a single bond. Preferred embodiments of compounds of the formula (I-1) are the following compounds of the formulae (I-1-A) to (I-1-F)

formula (I-1-A)

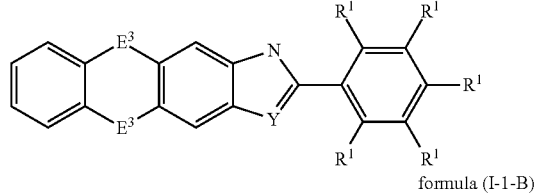

formula (I-1-B)

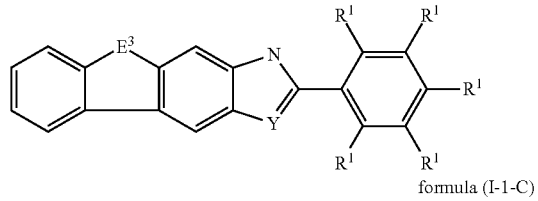

formula (I-1-C)

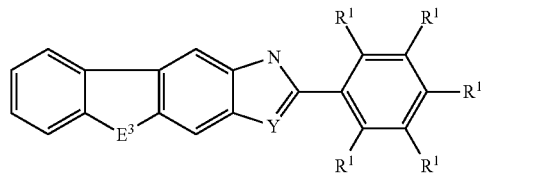

-continued formula (I-1-D)

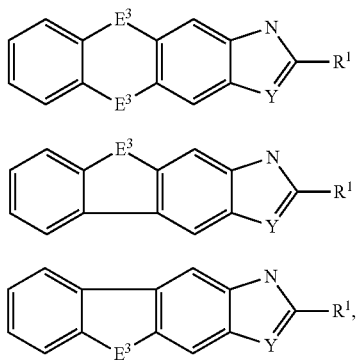

formula (I-1-E)

formula (I-1-F)

where the compounds may be substituted at all free positions by radicals $R^2$, and where $E^3$ is on each occurrence, identically or differently, C=O, $N(R^1)$, O or S; and Y, $R^1$, $R^2$ are defined as above; and where at least one group $R^1$ is selected from groups of the formulae (Het-a) to (Het-e), as defined above.

The above-mentioned preferred embodiments of groups are likewise regarded as preferred.

In particular, the preferred embodiments of groups $R^1$ and/or $R^2$ are regarded as preferred for formulae (I-1-A) to (I-1-F).

Furthermore, for formulae (I-1-A) to (I-1-F), Y is especially preferably equal to $NR^1$.

Examples of compounds of the formula (I) are depicted in the following table.

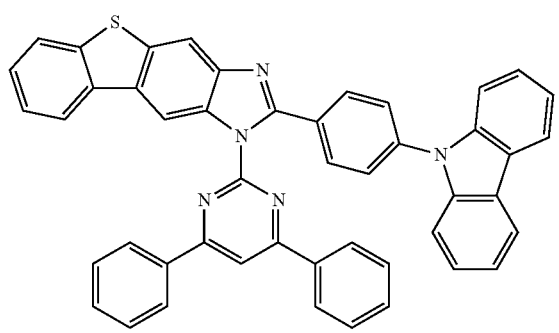 [SMILES: c1ccc(-c2cc(-c3ccccc3)nc(-n3c(-c4ccc(-n5c6ccccc6c6ccccc65)cc4)nc4cc5sc6ccccc6c5cc43)n2)cc1]

1

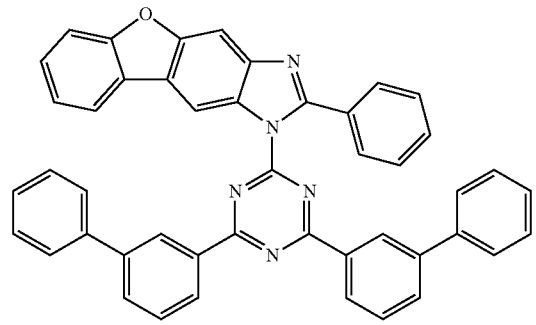 [SMILES: c1ccc(-c2cccc(-c3nc(-c4cccc(-c5ccccc5)c4)nc(-n4c(-c5ccccc5)nc5cc6oc7ccccc7c6cc54)n3)c2)cc1]

2

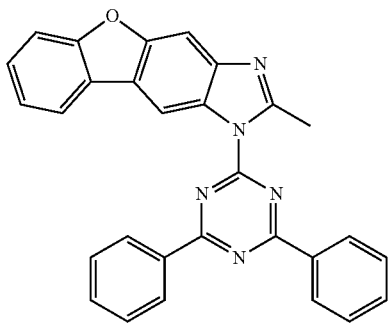 [SMILES: Cc1nc2cc3oc4ccccc4c3cc2n1-c1nc(-c2ccccc2)nc(-c2ccccc2)n1]

3

-continued
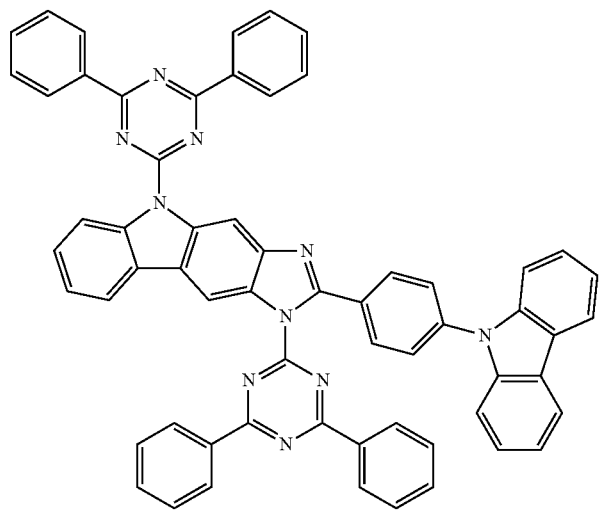 [SMILES: c1ccc(-c2nc(-c3ccccc3)nc(-n3c(-c4ccc(-n5c6ccccc6c6ccccc65)cc4)nc4cc5c(cc43)c3ccccc3n5-c3nc(-c4ccccc4)nc(-c4ccccc4)n3)n2)cc1]
4
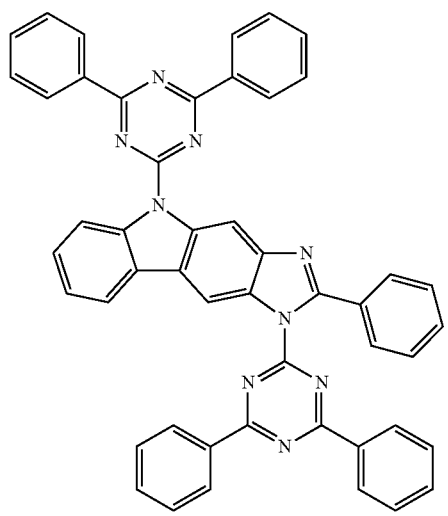 [SMILES: c1ccc(-c2nc(-c3ccccc3)nc(-n3c(-c4ccccc4)nc4cc5c(cc43)c3ccccc3n5-c3nc(-c4ccccc4)nc(-c4ccccc4)n3)n2)cc1]
5
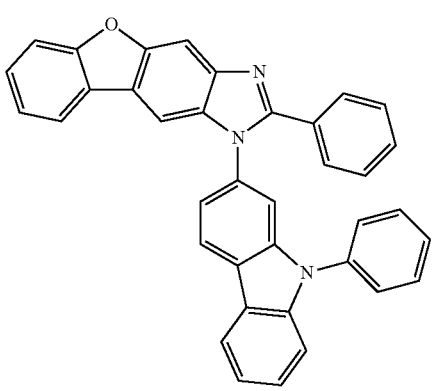 [SMILES: c1ccc(-c2nc3cc4oc5ccccc5c4cc3n2-c2ccc3c4ccccc4n(-c4ccccc4)c3c2)cc1]
6

-continued
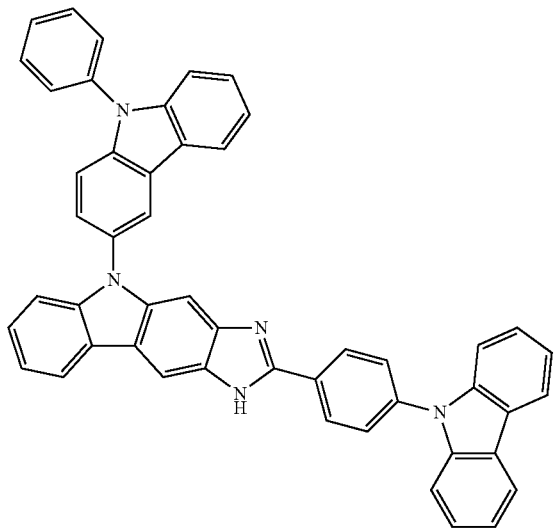 [SMILES: c1ccc(-n2c3ccccc3c3cc(-n4c5ccccc5c5cc6[nH]c(-c7ccc(-n8c9ccccc9c9ccccc98)cc7)nc6cc54)ccc32)cc1]
7
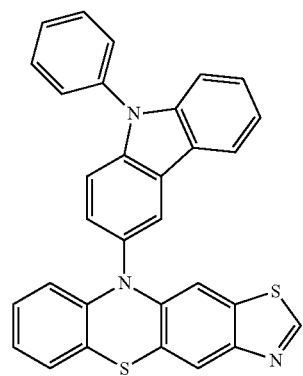 [SMILES: c1ccc(-n2c3ccccc3c3cc(N4c5ccccc5Sc5cc6ncsc6cc54)ccc32)cc1]
8
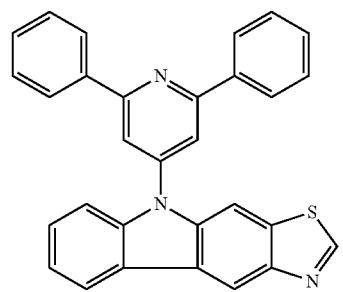 [SMILES: c1ccc(-c2cc(-n3c4ccccc4c4cc5ncsc5cc43)cc(-c3ccccc3)n2)cc1]
9

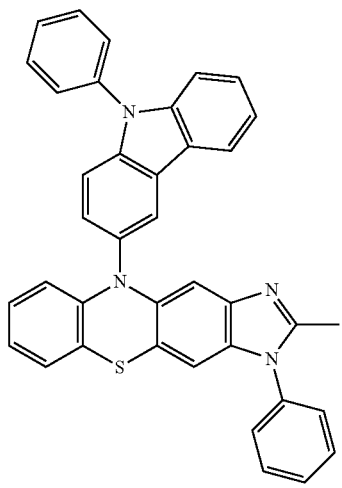 [SMILES: Cc1nc2cc3c(cc2n1-c1ccccc1)Sc1ccccc1N3c1ccc2c(c1)c1ccccc1n2-c1ccccc1]
10
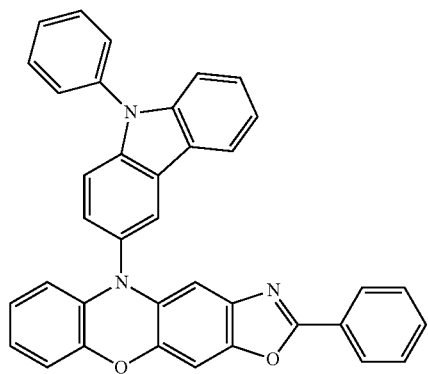 [SMILES: c1ccc(-c2nc3cc4c(cc3o2)Oc2ccccc2N4c2ccc3c(c2)c2ccccc2n3-c2ccccc2)cc1]
11
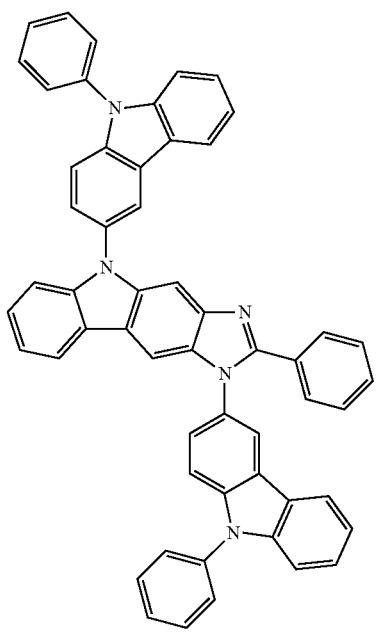 [SMILES: c1ccc(-c2nc3cc4c(cc3n2-c2ccc3c(c2)c2ccccc2n3-c2ccccc2)c2ccccc2n4-c2ccc3c(c2)c2ccccc2n3-c2ccccc2)cc1]
12

-continued
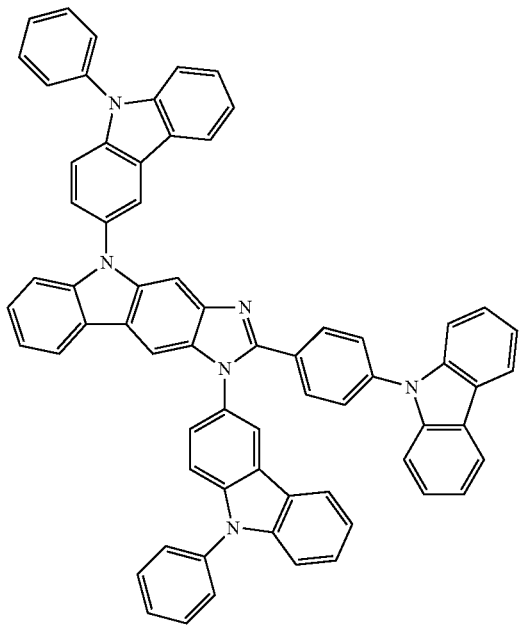 [SMILES: c1ccc(-n2c3ccccc3c3cc(-n4c(-c5ccc(-n6c7ccccc7c7ccccc76)cc5)nc5cc6c(cc54)c4ccccc4n6-c4ccc5c(c4)c4ccccc4n5-c4ccccc4)ccc32)cc1]
13
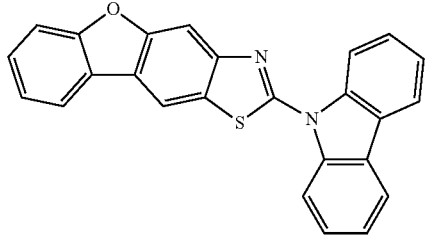 [SMILES: c1ccc2c(c1)oc1cc3nc(-n4c5ccccc5c5ccccc54)sc3cc12]
14
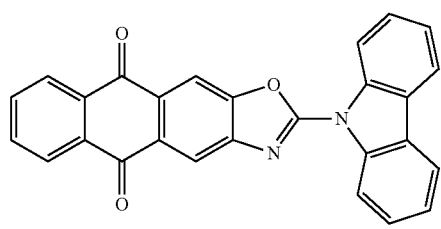 [SMILES: O=C1c2ccccc2C(=O)c2cc3oc(-n4c5ccccc5c5ccccc54)nc3cc21]
15
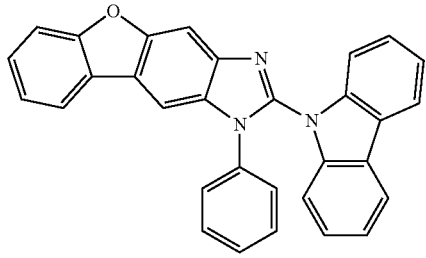 [SMILES: c1ccc(-n2c(-n3c4ccccc4c4ccccc43)nc3cc4oc5ccccc5c4cc32)cc1]
16
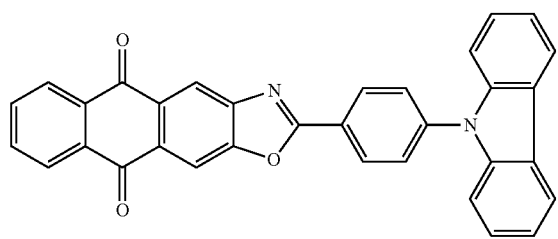 [SMILES: O=C1c2ccccc2C(=O)c2cc3oc(-c4ccc(-n5c6ccccc6c6ccccc65)cc4)nc3cc21]
17

-continued
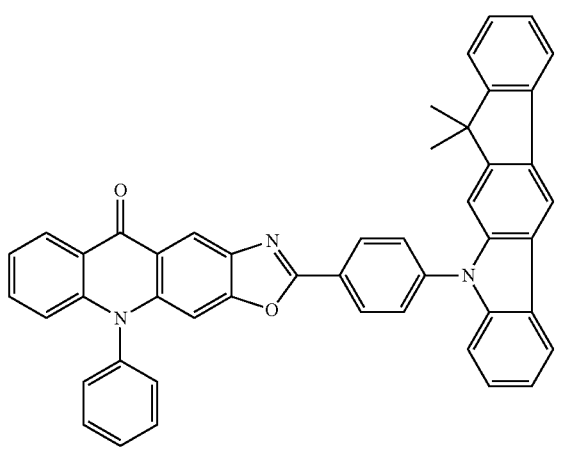 [SMILES: CC1(C)c2ccccc2-c2cc3c4ccccc4n(-c4ccc(-c5nc6cc7c(=O)c8ccccc8n(-c8ccccc8)c7cc6o5)cc4)c3cc21]
18
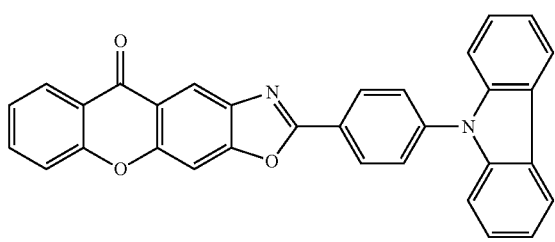 [SMILES: O=c1c2ccccc2oc2cc3oc(-c4ccc(-n5c6ccccc6c6ccccc65)cc4)nc3cc12]
19
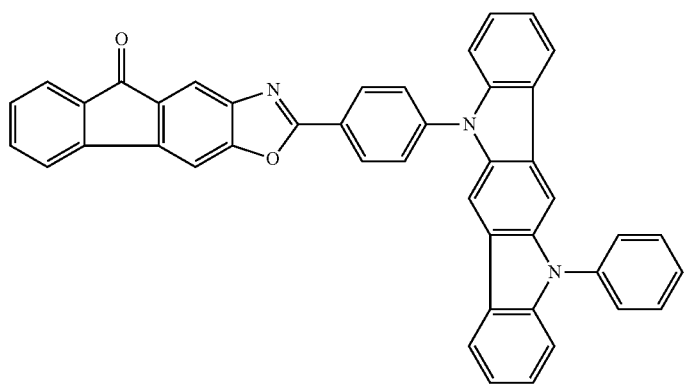 [SMILES: O=C1c2ccccc2-c2cc3oc(-c4ccc(-n5c6ccccc6c6cc7c(cc65)c5ccccc5n7-c5ccccc5)cc4)nc3cc21]
20
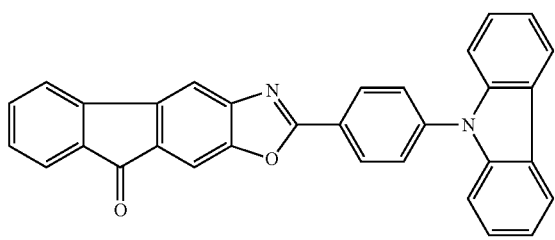 [SMILES: O=C1c2ccccc2-c2cc3nc(-c4ccc(-n5c6ccccc6c6ccccc65)cc4)oc3cc21]
21

-continued
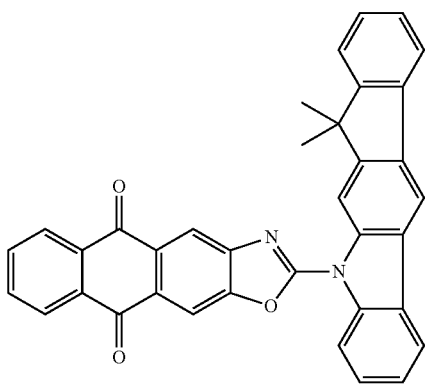 [SMILES: CC1(C)c2ccccc2-c2cc3c4ccccc4n(-c4nc5cc6c(cc5o4)C(=O)c4ccccc4C6=O)c3cc21]
22
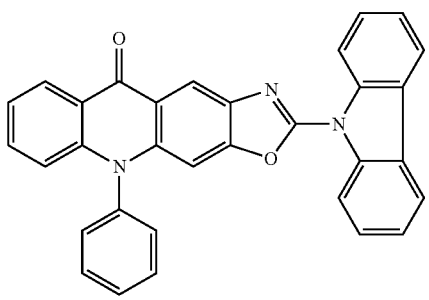 [SMILES: O=c1c2ccccc2n(-c2ccccc2)c2cc3oc(-n4c5ccccc5c5ccccc54)nc3cc12]
23
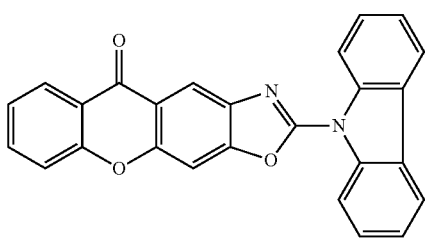 [SMILES: O=c1c2ccccc2oc2cc3oc(-n4c5ccccc5c5ccccc54)nc3cc12]
24
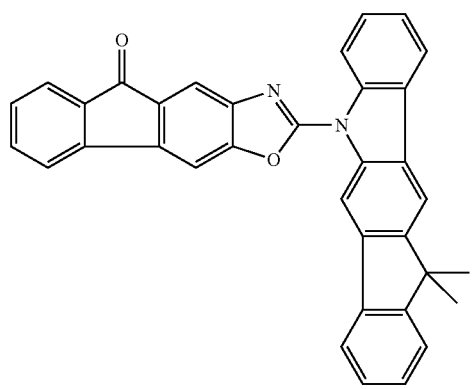 [SMILES: CC1(C)c2ccccc2-c2cc3c(cc21)c1ccccc1n3-c1nc2cc3c(cc2o1)-c1ccccc1C3=O]
25
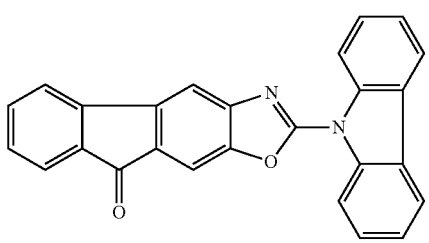 [SMILES: O=C1c2ccccc2-c2cc3nc(-n4c5ccccc5c5ccccc54)oc3cc21]
26

27
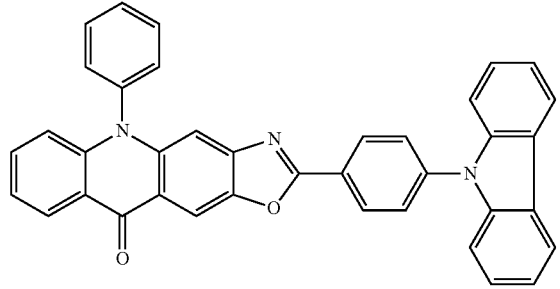 [SMILES: O=c1c2ccccc2n(-c2ccccc2)c2cc3nc(-c4ccc(-n5c6ccccc6c6ccccc65)cc4)oc3cc12]
28
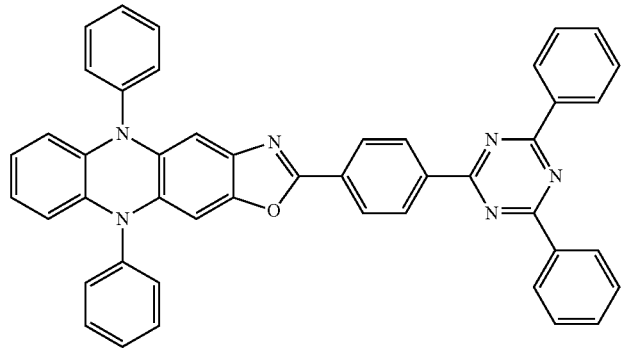
29
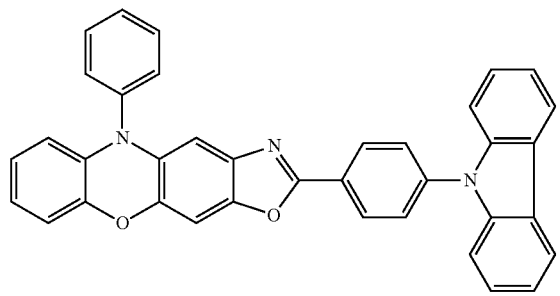 [SMILES: c1ccc(N2c3ccccc3Oc3cc4oc(-c5ccc(-n6c7ccccc7c7ccccc76)cc5)nc4cc32)cc1]
30
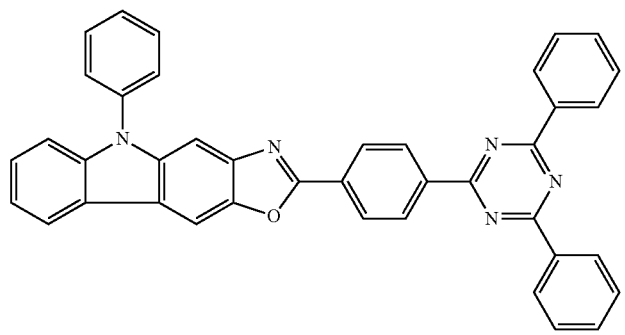 [SMILES: c1ccc(-c2nc(-c3ccccc3)nc(-c3ccc(-c4nc5cc6c(cc5o4)c4ccccc4n6-c4ccccc4)cc3)n2)cc1]
31
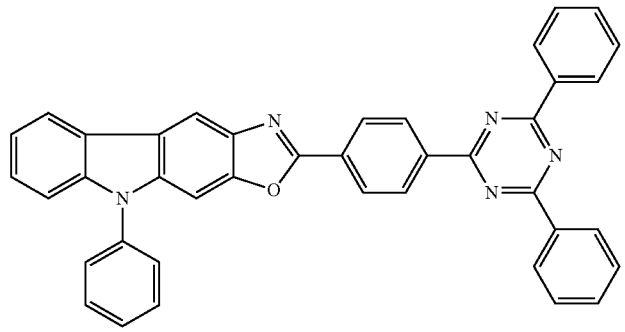

-continued
32
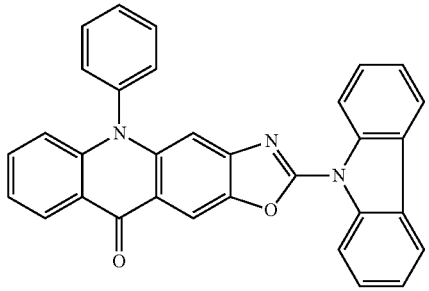 [SMILES: O=c1c2ccccc2n(-c2ccccc2)c2cc3nc(-n4c5ccccc5c5ccccc54)oc3cc12]
33
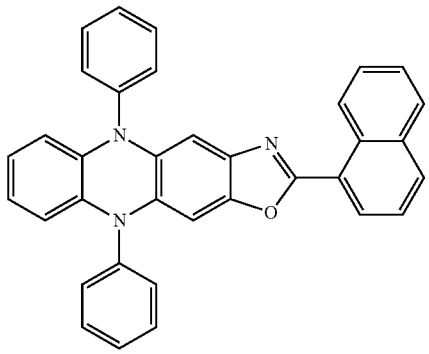 [SMILES: c1ccc(N2c3ccccc3N(c3ccccc3)c3cc4oc(-c5cccc6ccccc56)nc4cc32)cc1]
34
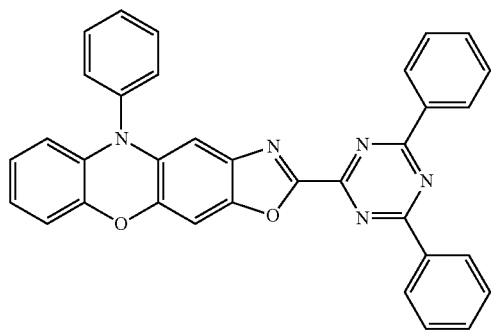 [SMILES: c1ccc(-c2nc(-c3ccccc3)nc(-c3nc4cc5c(cc4o3)Oc3ccccc3N5c3ccccc3)n2)cc1]
35
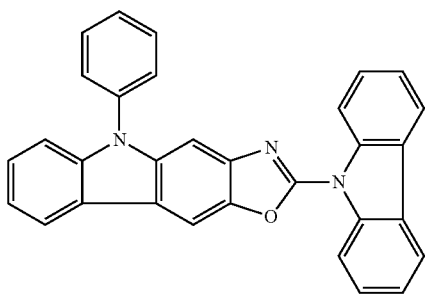 [SMILES: c1ccc(-n2c3ccccc3c3cc4oc(-n5c6ccccc6c6ccccc65)nc4cc32)cc1]
36
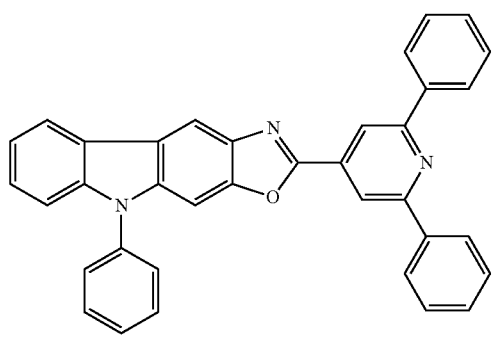 [SMILES: c1ccc(-c2cc(-c3nc4cc5c6ccccc6n(-c6ccccc6)c5cc4o3)cc(-c3ccccc3)n2)cc1]

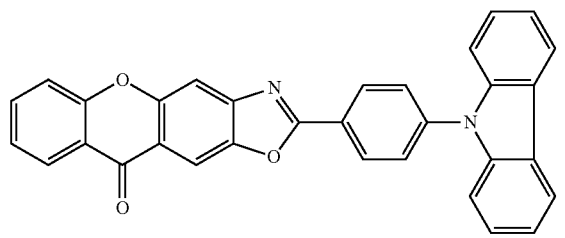 [SMILES: O=c1c2ccccc2oc2cc3nc(-c4ccc(-n5c6ccccc6c6ccccc65)cc4)oc3cc12]
37
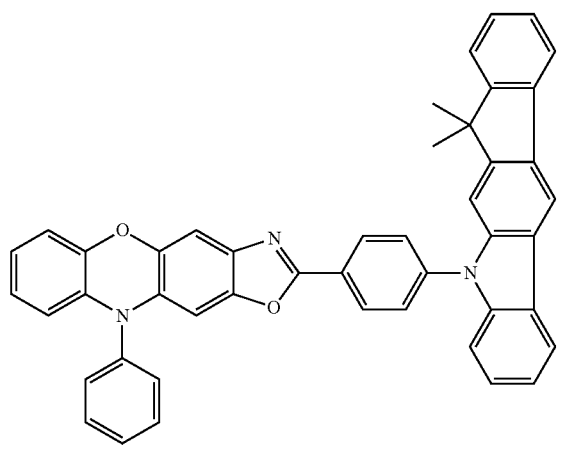 [SMILES: CC1(C)c2ccccc2-c2cc3c4ccccc4n(-c4ccc(-c5nc6cc7c(cc6o5)N(c5ccccc5)c5ccccc5O7)cc4)c3cc21]
38
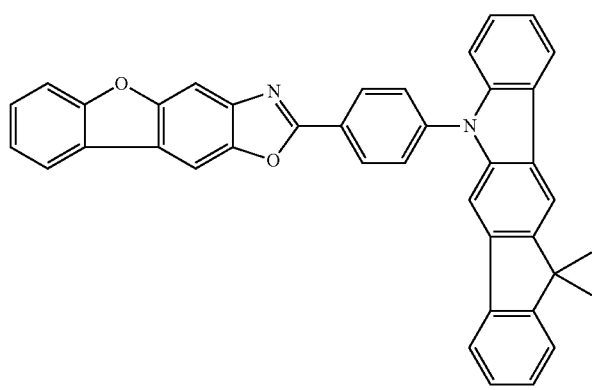 [SMILES: CC1(C)c2ccccc2-c2cc3c(cc21)c1ccccc1n3-c1ccc(-c2nc3cc4oc5ccccc5c4cc3o2)cc1]
39
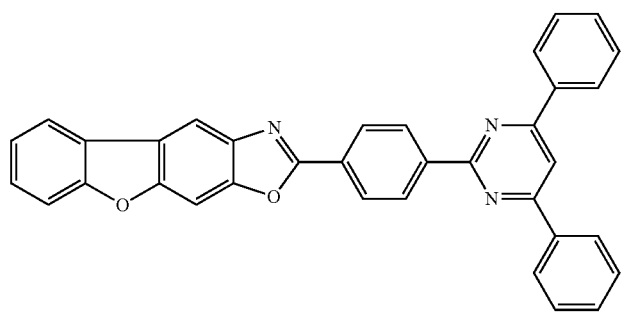
40

-continued
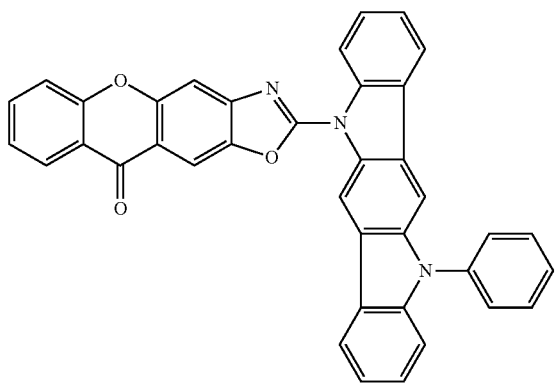 [SMILES: O=c1c2ccccc2oc2cc3nc(-n4c5ccccc5c5cc6c(cc54)c4ccccc4n6-c4ccccc4)oc3cc12]
41
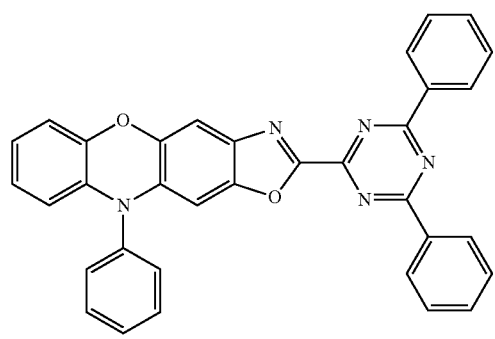
42
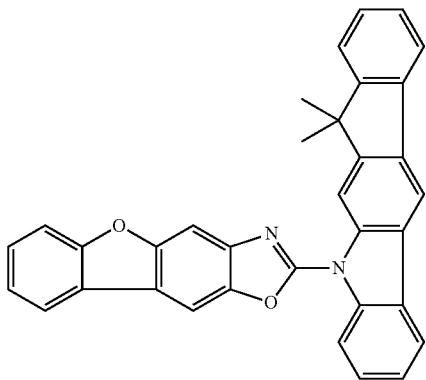 [SMILES: CC1(C)c2ccccc2-c2cc3c4ccccc4n(-c4nc5cc6oc7ccccc7c6cc5o4)c3cc21]
43
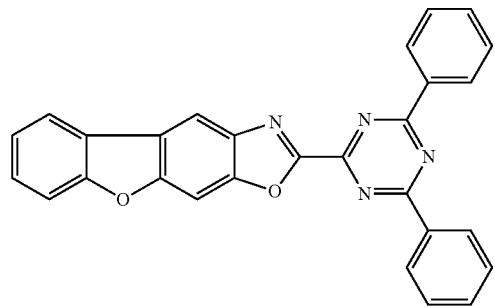 [SMILES: c1ccc(-c2nc(-c3ccccc3)nc(-c3nc4cc5c(cc4o3)oc3ccccc35)n2)cc1]
44

-continued
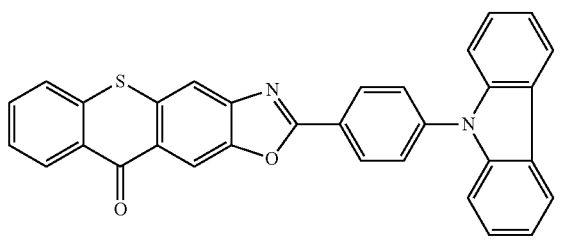
45
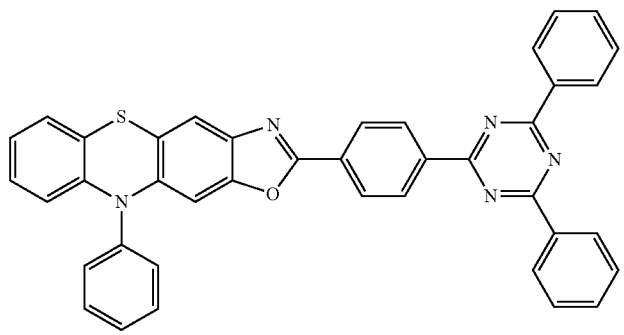 [SMILES: c1ccc(-c2nc(-c3ccccc3)nc(-c3ccc(-c4nc5cc6c(cc5o4)N(c4ccccc4)c4ccccc4S6)cc3)n2)cc1]
46
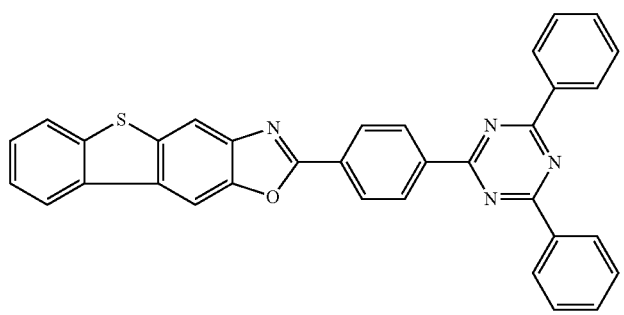
47
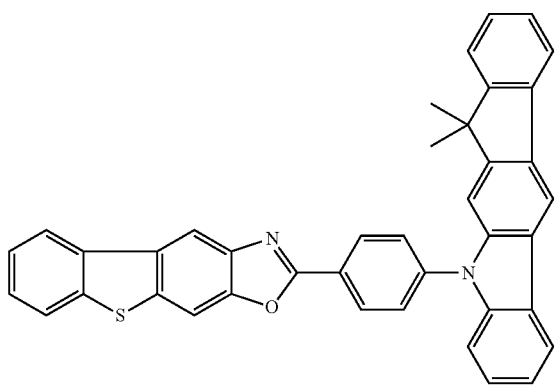 [SMILES: CC1(C)c2ccccc2-c2cc3c4ccccc4n(-c4ccc(-c5nc6cc7c(cc6o5)sc5ccccc57)cc4)c3cc21]
48
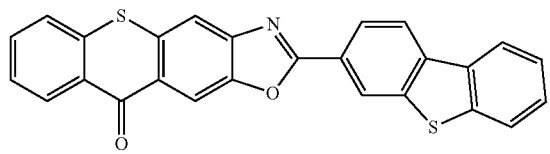 [SMILES: O=c1c2ccccc2sc2cc3nc(-c4ccc5c(c4)sc4ccccc45)oc3cc12]
49

-continued
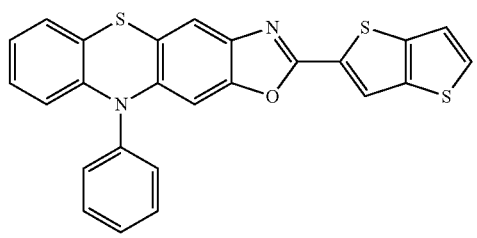 [SMILES: c1ccc(N2c3ccccc3Sc3cc4nc(-c5cc6sccc6s5)oc4cc32)cc1]
50
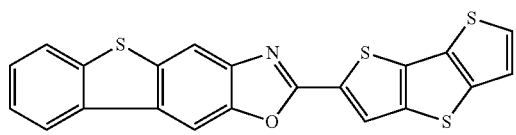 [SMILES: c1ccc2c(c1)sc1cc3nc(-c4cc5sc6ccsc6c5s4)oc3cc12]
51
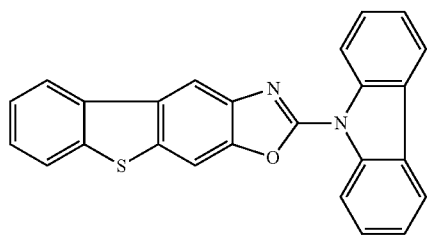 [SMILES: c1ccc2c(c1)sc1cc3oc(-n4c5ccccc5c5ccccc54)nc3cc12]
52
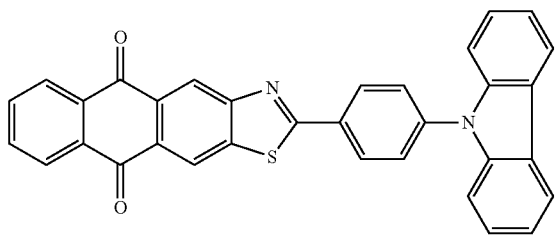 [SMILES: O=C1c2ccccc2C(=O)c2cc3sc(-c4ccc(-n5c6ccccc6c6ccccc65)cc4)nc3cc21]
53
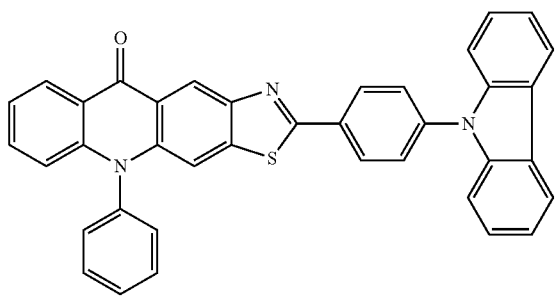 [SMILES: O=c1c2ccccc2n(-c2ccccc2)c2cc3sc(-c4ccc(-n5c6ccccc6c6ccccc65)cc4)nc3cc12]
54
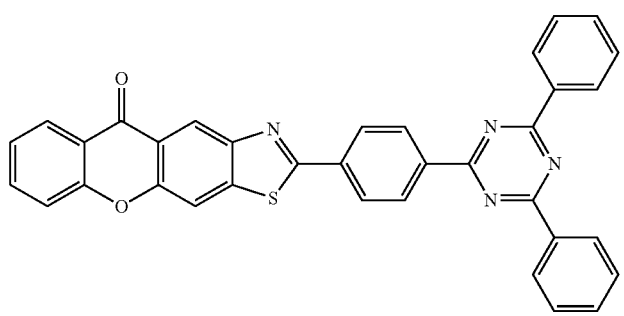 [SMILES: O=c1c2ccccc2oc2cc3sc(-c4ccc(-c5nc(-c6ccccc6)nc(-c6ccccc6)n5)cc4)nc3cc12]
55

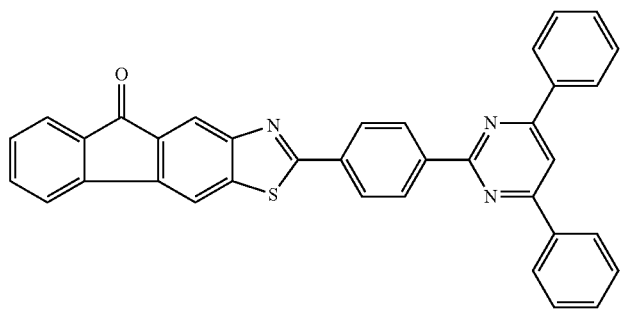 [SMILES: O=C1c2ccccc2-c2cc3sc(-c4ccc(-c5nc(-c6ccccc6)cc(-c6ccccc6)n5)cc4)nc3cc21]
56
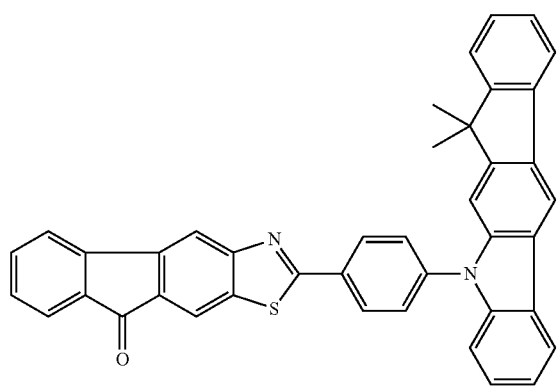 [SMILES: CC1(C)c2ccccc2-c2cc3c4ccccc4n(-c4ccc(-c5nc6cc7c(cc6s5)C(=O)c5ccccc5-7)cc4)c3cc21]
57
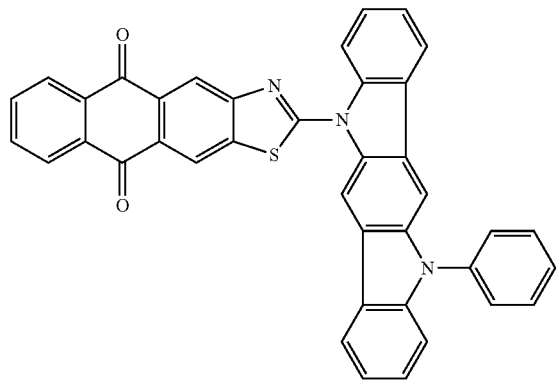 [SMILES: O=C1c2ccccc2C(=O)c2cc3sc(-n4c5ccccc5c5cc6c(cc54)c4ccccc4n6-c4ccccc4)nc3cc21]
58
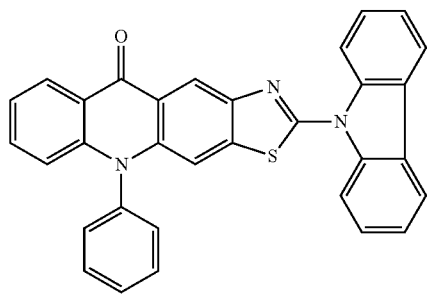
59

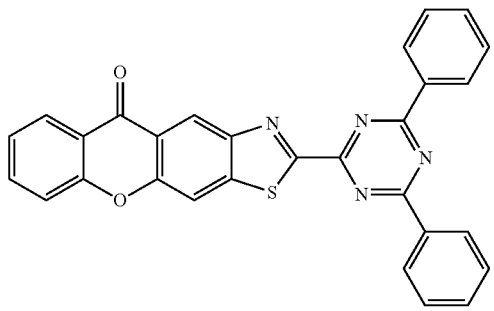 [SMILES: O=c1c2ccccc2oc2cc3sc(-c4nc(-c5ccccc5)nc(-c5ccccc5)n4)nc3cc12]
60
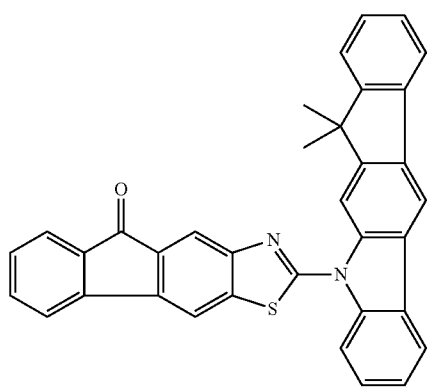 [SMILES: CC1(C)c2ccccc2-c2cc3c4ccccc4n(-c4nc5cc6c(cc5s4)-c4ccccc4C6=O)c3cc21]
61
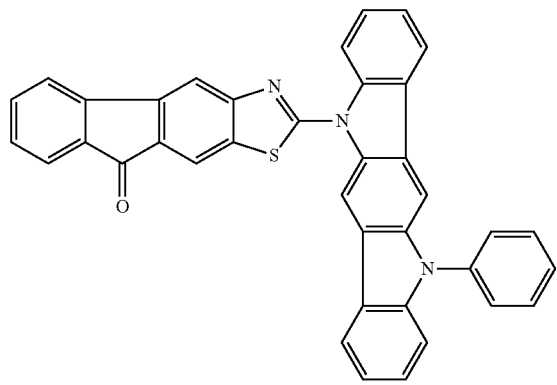 [SMILES: O=C1c2ccccc2-c2cc3nc(-n4c5ccccc5c5cc6c(cc54)c4ccccc4n6-c4ccccc4)sc3cc21]
62
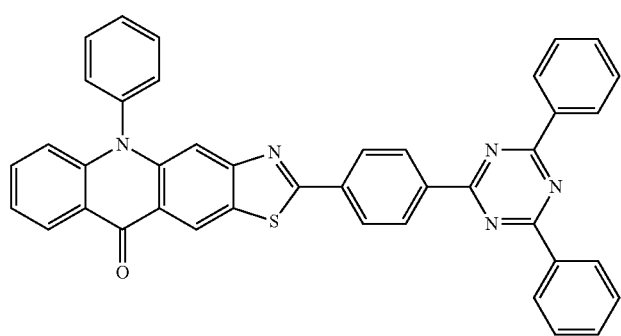 [SMILES: O=c1c2ccccc2n(-c2ccccc2)c2cc3nc(-c4ccc(-c5nc(-c6ccccc6)nc(-c6ccccc6)n5)cc4)sc3cc12]
63

-continued
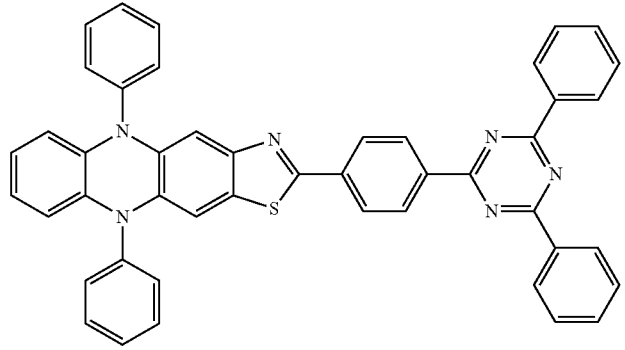 [SMILES: c1ccc(-c2nc(-c3ccccc3)nc(-c3ccc(-c4nc5cc6c(cc5s4)N(c4ccccc4)c4ccccc4N6c4ccccc4)cc3)n2)cc1]
64
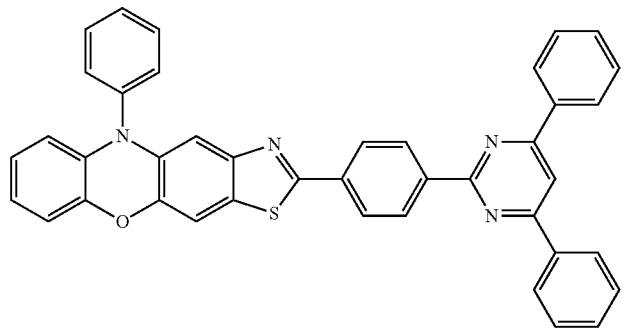 [SMILES: c1ccc(-c2cc(-c3ccccc3)nc(-c3ccc(-c4nc5cc6c(cc5s4)Oc4ccccc4N6c4ccccc4)cc3)n2)cc1]
65
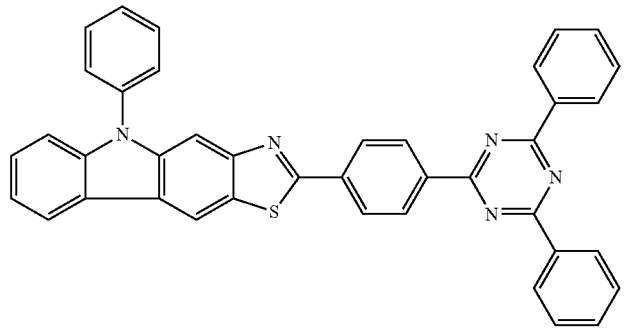 [SMILES: c1ccc(-c2nc(-c3ccccc3)nc(-c3ccc(-c4nc5cc6c(cc5s4)c4ccccc4n6-c4ccccc4)cc3)n2)cc1]
66
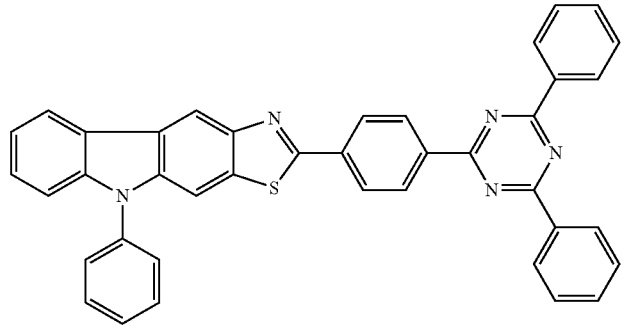
67

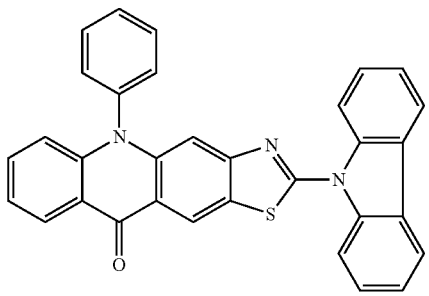 [SMILES: O=c1c2ccccc2n(-c2ccccc2)c2cc3nc(-n4c5ccccc5c5ccccc54)sc3cc12]
68
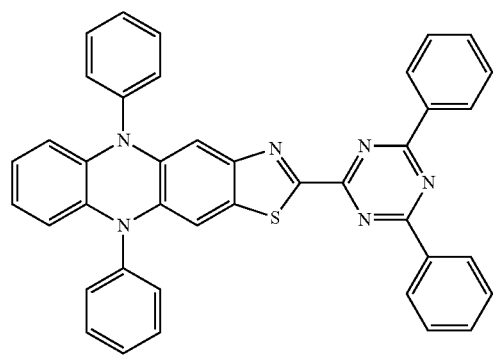 [SMILES: c1ccc(-c2nc(-c3ccccc3)nc(-c3nc4cc5c(cc4s3)N(c3ccccc3)c3ccccc3N5c3ccccc3)n2)cc1]
69
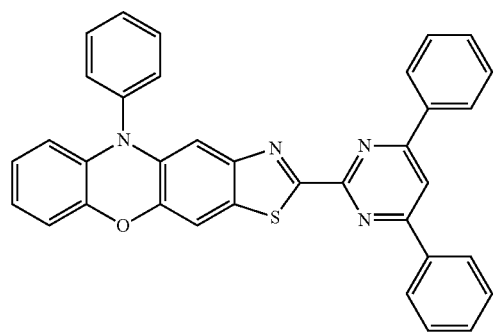 [SMILES: c1ccc(-c2cc(-c3ccccc3)nc(-c3nc4cc5c(cc4s3)Oc3ccccc3N5c3ccccc3)n2)cc1]
70
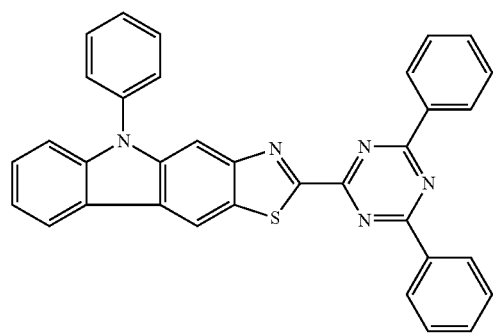 [SMILES: c1ccc(-c2nc(-c3ccccc3)nc(-c3nc4cc5c(cc4s3)c3ccccc3n5-c3ccccc3)n2)cc1]
71

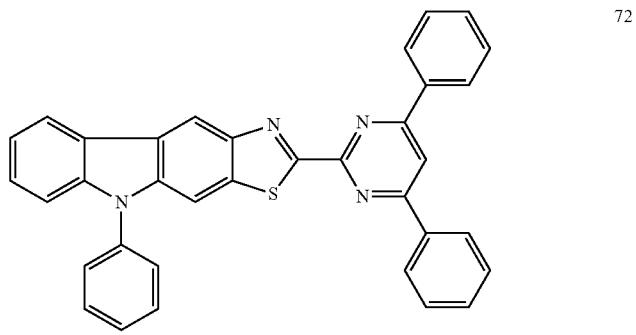
72
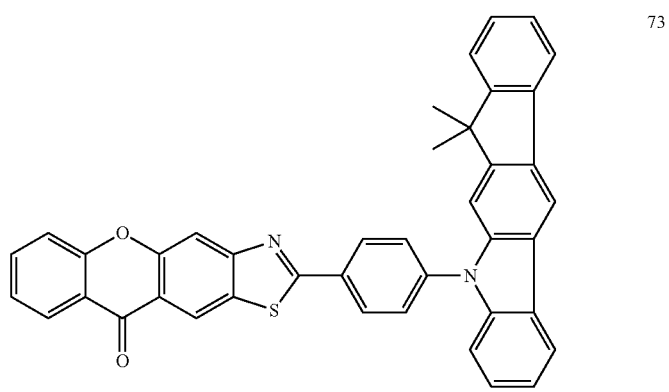
73
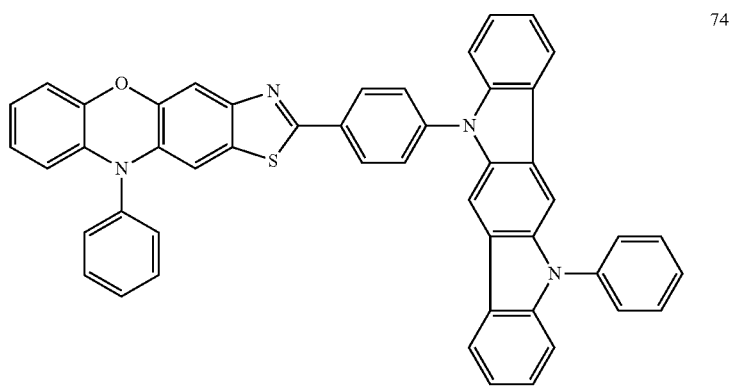
74
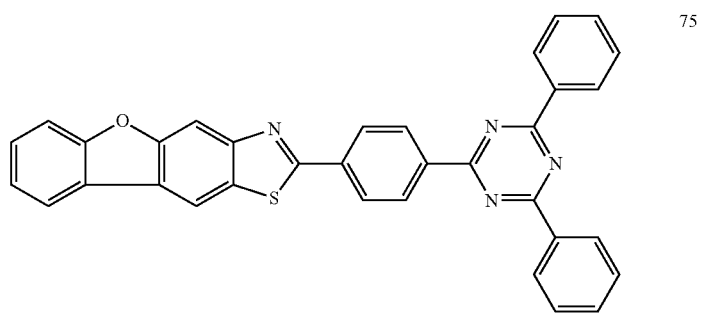
75

-continued
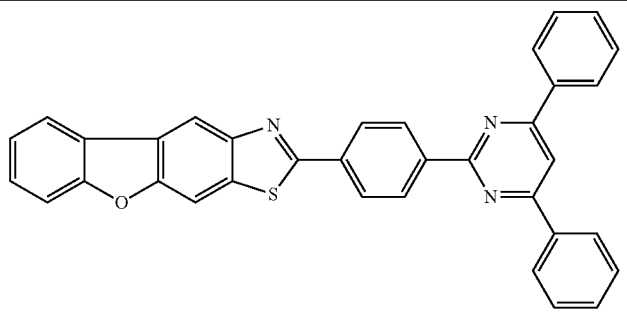
76
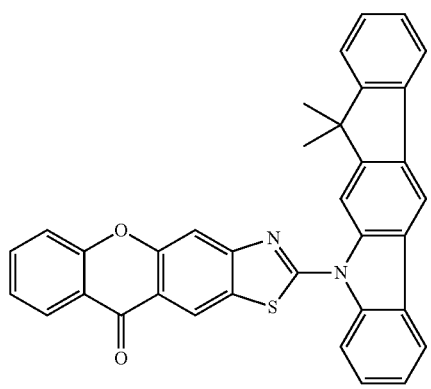 [SMILES: CC1(C)c2ccccc2-c2cc3c4ccccc4n(-c4nc5cc6oc7ccccc7c(=O)c6cc5s4)c3cc21]
77
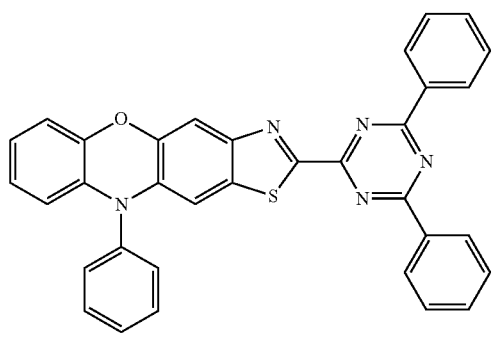
78
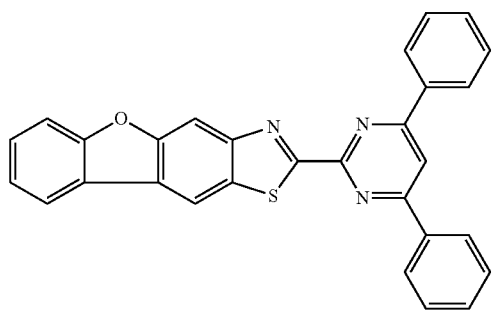 [SMILES: c1ccc(-c2cc(-c3ccccc3)nc(-c3nc4cc5oc6ccccc6c5cc4s3)n2)cc1]
79
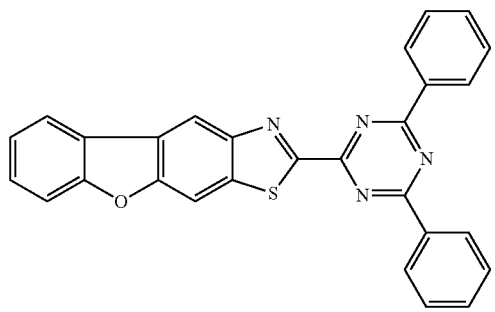
80

-continued
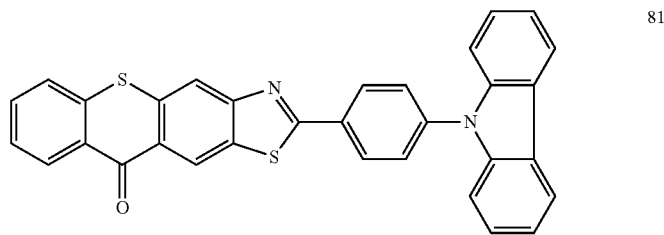
81
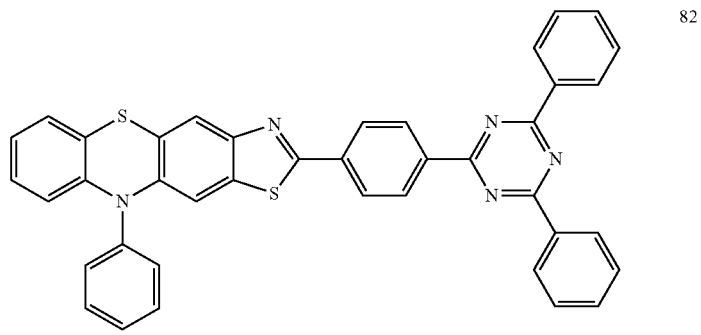
82
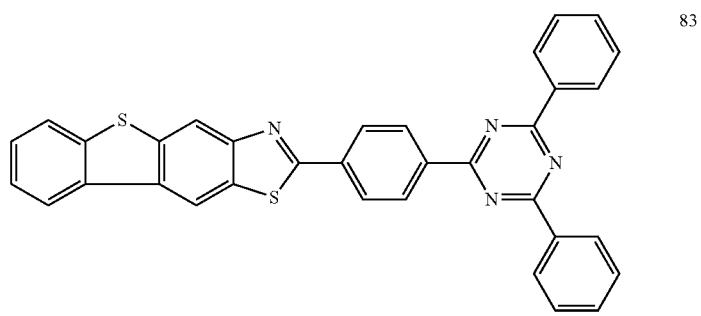
83
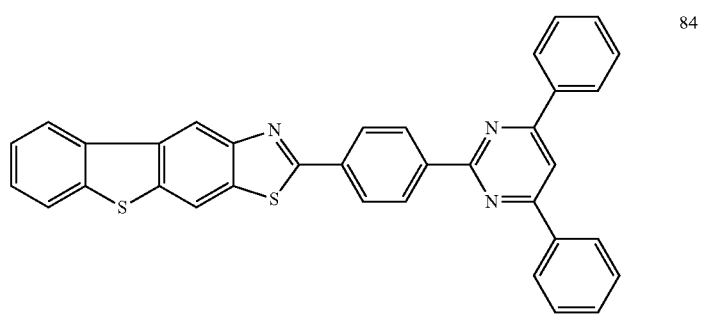
84
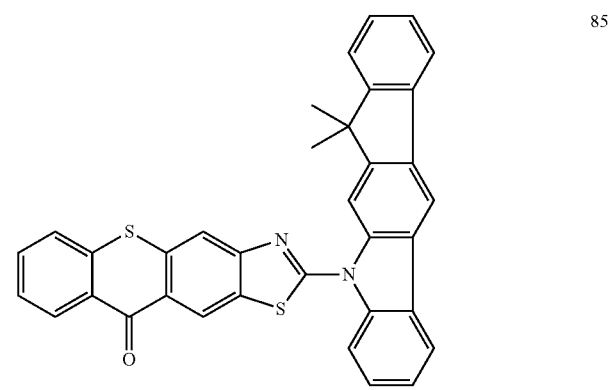
85

86
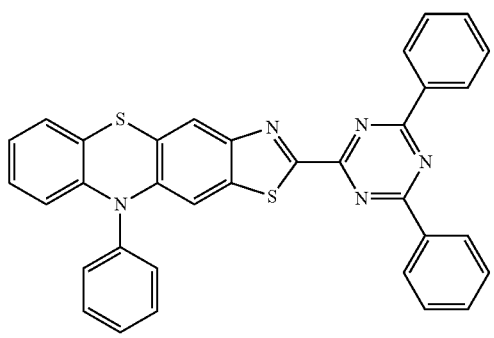 [SMILES: c1ccc(-c2nc(-c3ccccc3)nc(-c3nc4cc5c(cc4s3)N(c3ccccc3)c3ccccc3S5)n2)cc1]
87
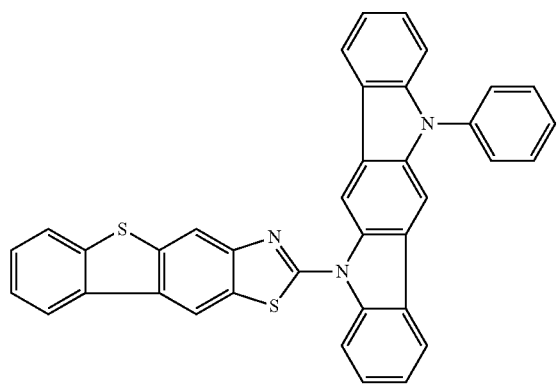 [SMILES: c1ccc(-n2c3ccccc3c3cc4c(cc32)c2ccccc2n4-c2nc3cc4sc5ccccc5c4cc3s2)cc1]
88
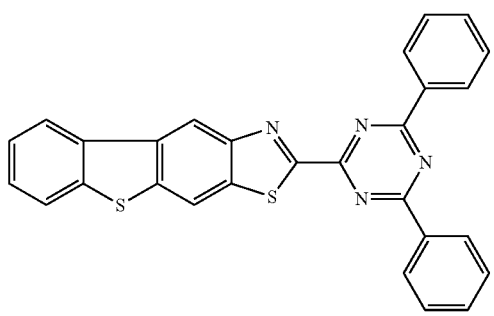
89
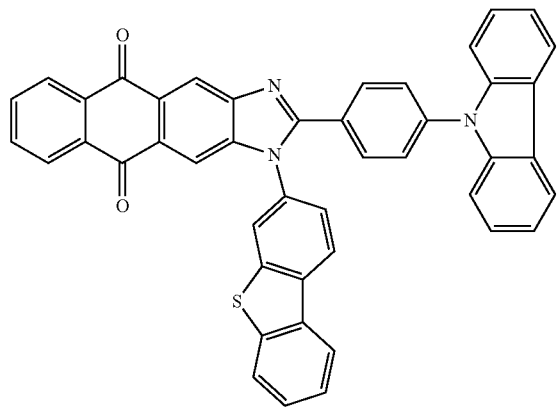 [SMILES: O=C1c2ccccc2C(=O)c2cc3c(cc21)nc(-c1ccc(-n2c4ccccc4c4ccccc42)cc1)n3-c1ccc2c(c1)sc1ccccc12]

-continued
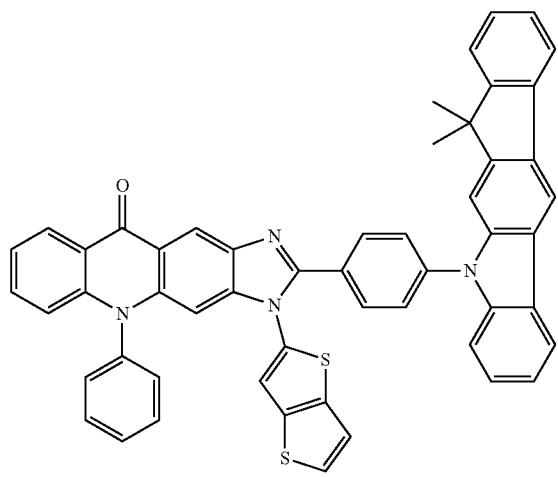 [SMILES: CC1(C)c2ccccc2-c2cc3c4ccccc4n(-c4ccc(-c5nc6cc7c(=O)c8ccccc8n(-c8ccccc8)c7cc6n5-c5cc6sccc6s5)cc4)c3cc21]
90
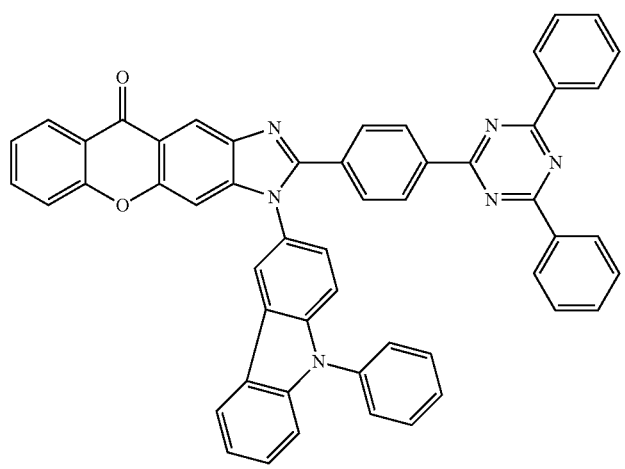 [SMILES: O=c1c2ccccc2oc2cc3c(cc12)nc(-c1ccc(-c2nc(-c4ccccc4)nc(-c4ccccc4)n2)cc1)n3-c1ccc2c(c1)c1ccccc1n2-c1ccccc1]
91
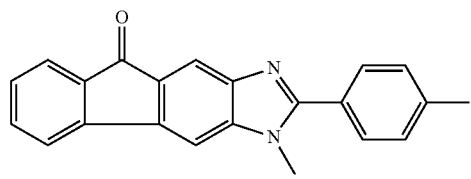 [SMILES: Cc1ccc(-c2nc3cc4c(cc3n2C)-c2ccccc2C4=O)cc1]
92

-continued
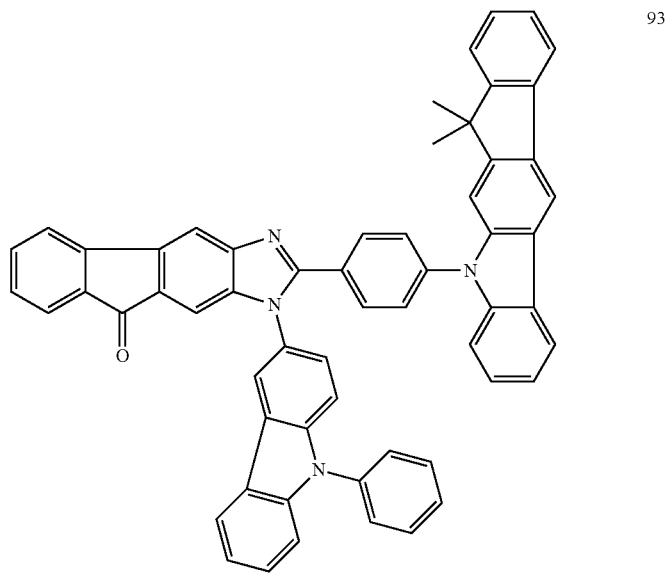
93
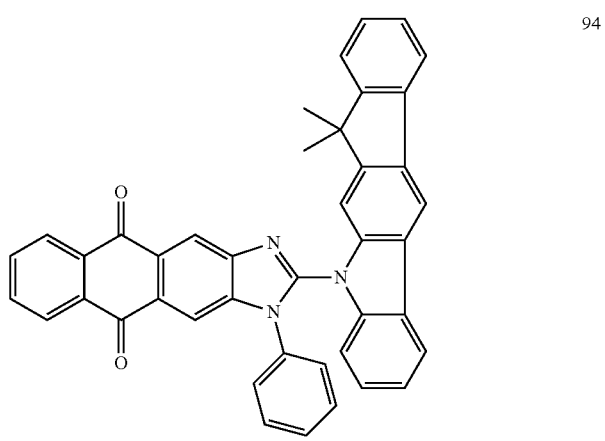
94
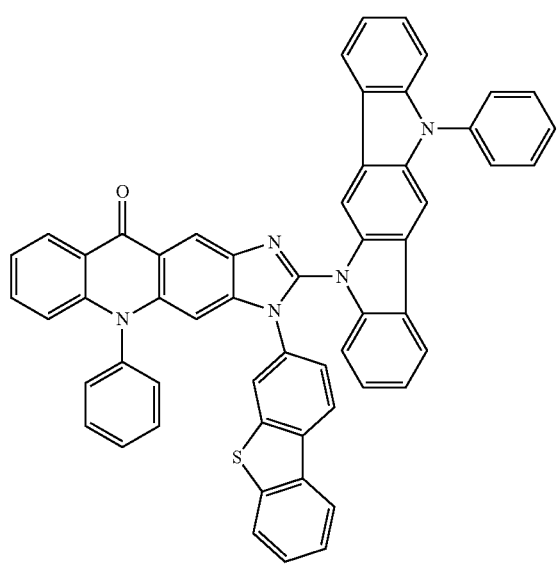 [SMILES: O=c1c2ccccc2n(-c2ccccc2)c2cc3c(cc12)nc(-n1c2ccccc2c2cc4c(cc21)c1ccccc1n4-c1ccccc1)n3-c1ccc2c(c1)sc1ccccc12]
95

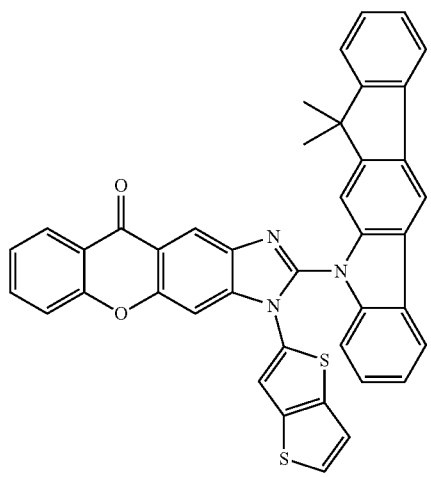 [SMILES: CC1(C)c2ccccc2-c2cc3c4ccccc4n(-c4nc5cc6c(=O)c7ccccc7oc6cc5n4-c4cc5sccc5s4)c3cc21]
96
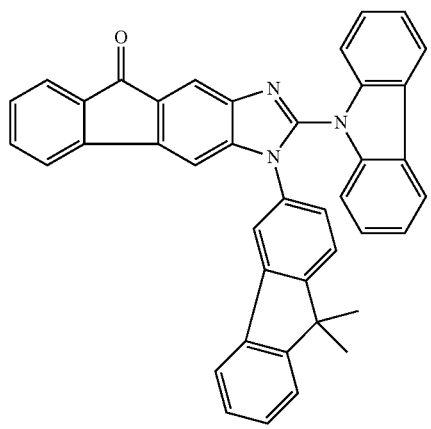 [SMILES: CC1(C)c2ccccc2-c2cc(-n3c(-n4c5ccccc5c5ccccc54)nc4cc5c(cc43)-c3ccccc3C5=O)ccc21]
97
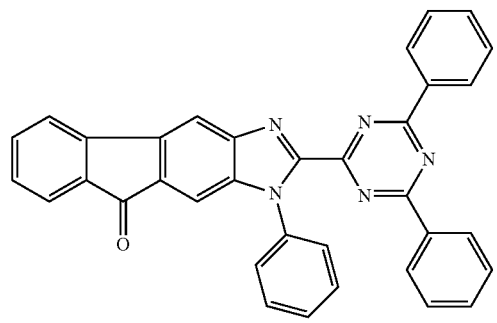 [SMILES: O=C1c2ccccc2-c2cc3nc(-c4nc(-c5ccccc5)nc(-c5ccccc5)n4)n(-c4ccccc4)c3cc21]
98

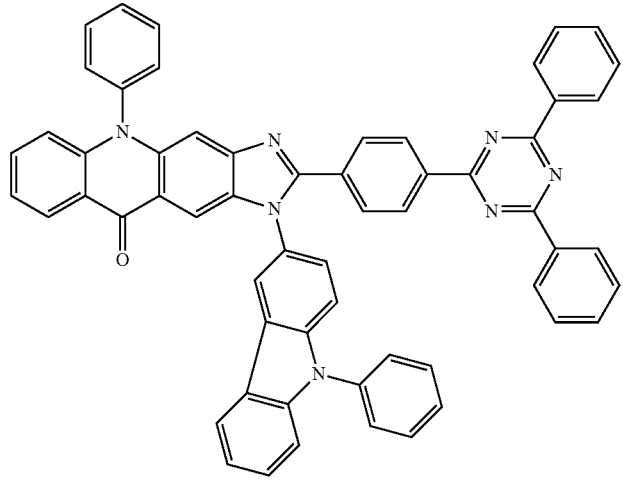 [SMILES: O=c1c2ccccc2n(-c2ccccc2)c2cc3nc(-c4ccc(-c5nc(-c6ccccc6)nc(-c6ccccc6)n5)cc4)n(-c4ccc5c(c4)c4ccccc4n5-c4ccccc4)c3cc12]
99
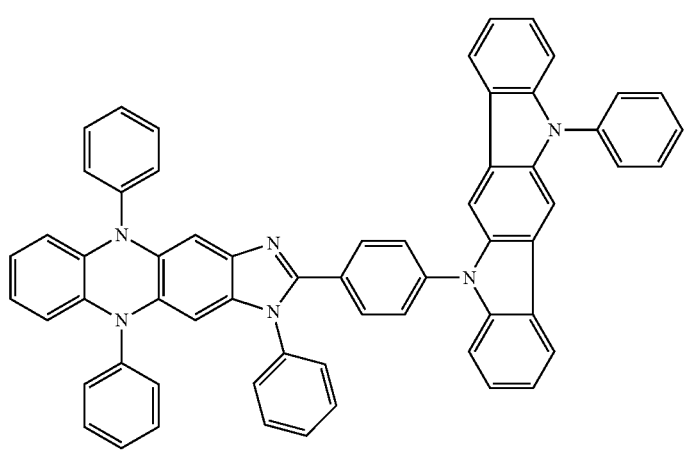 [SMILES: c1ccc(N2c3ccccc3N(c3ccccc3)c3cc4c(cc32)nc(-c2ccc(-n3c5ccccc5c5cc6c(cc53)c3ccccc3n6-c3ccccc3)cc2)n4-c2ccccc2)cc1]
100
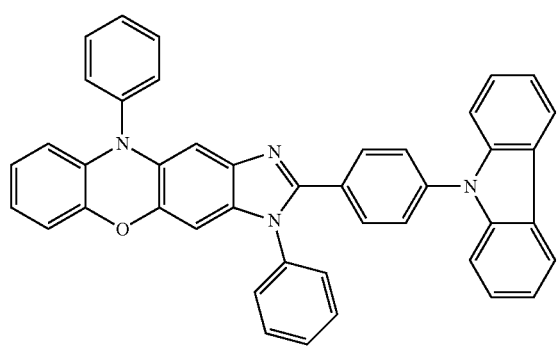 [SMILES: c1ccc(N2c3ccccc3Oc3cc4c(cc32)nc(-c2ccc(-n3c5ccccc5c5ccccc53)cc2)n4-c2ccccc2)cc1]
101
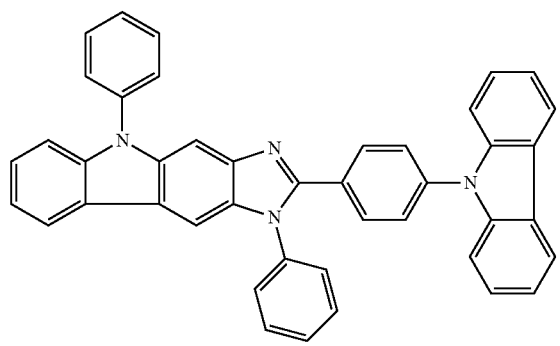 [SMILES: c1ccc(-n2c(-c3ccc(-n4c5ccccc5c5ccccc54)cc3)nc3cc4c(cc32)c2ccccc2n4-c2ccccc2)cc1]
102

-continued
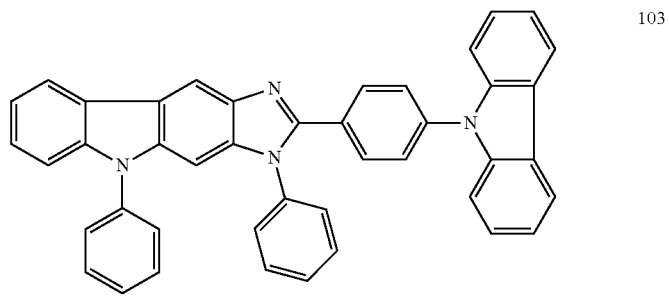
103
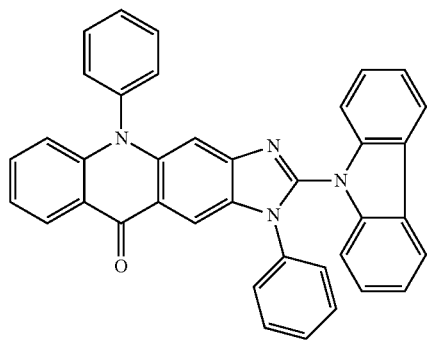 [SMILES: O=c1c2ccccc2n(-c2ccccc2)c2cc3nc(-n4c5ccccc5c5ccccc54)n(-c4ccccc4)c3cc12]
104
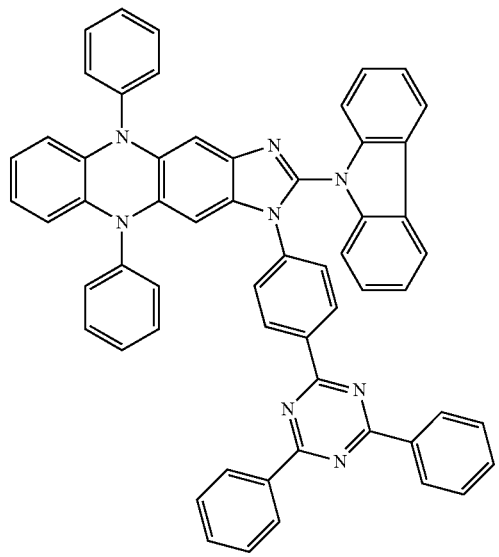 [SMILES: c1ccc(-c2nc(-c3ccccc3)nc(-c3ccc(-n4c(-n5c6ccccc6c6ccccc65)nc5cc6c(cc54)N(c4ccccc4)c4ccccc4N6c4ccccc4)cc3)n2)cc1]
105
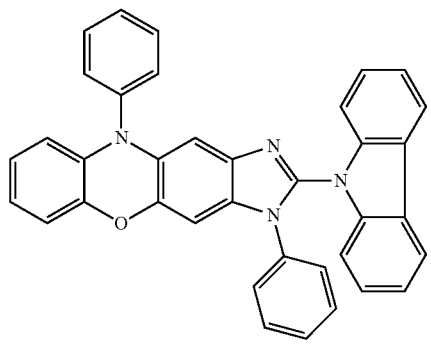 [SMILES: c1ccc(N2c3ccccc3Oc3cc4c(cc32)nc(-n2c3ccccc3c3ccccc32)n4-c2ccccc2)cc1]
106

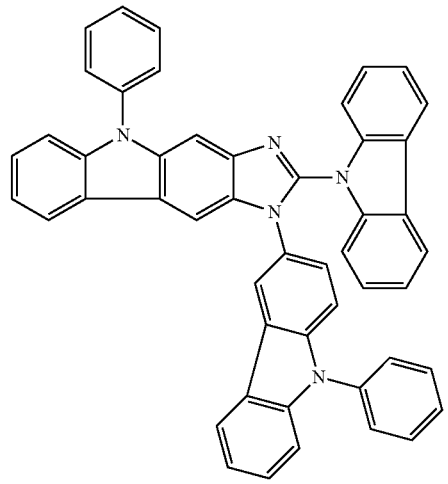 [SMILES: c1ccc(-n2c3ccccc3c3cc(-n4c(-n5c6ccccc6c6ccccc65)nc5cc6c(cc54)c4ccccc4n6-c4ccccc4)ccc32)cc1]
107
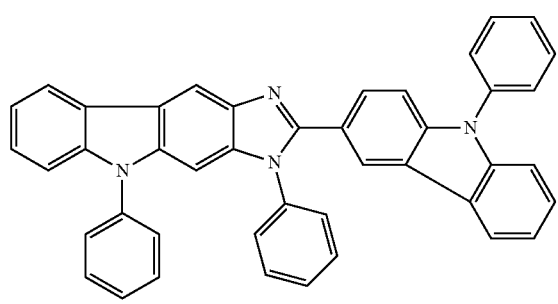 [SMILES: c1ccc(-n2c(-c3ccc4c(c3)c3ccccc3n4-c3ccccc3)nc3cc4c5ccccc5n(-c5ccccc5)c4cc32)cc1]
108
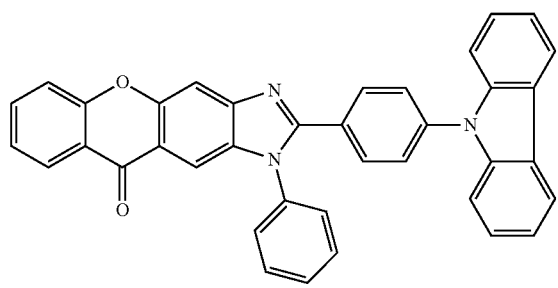 [SMILES: O=c1c2ccccc2oc2cc3nc(-c4ccc(-n5c6ccccc6c6ccccc65)cc4)n(-c4ccccc4)c3cc12]
109
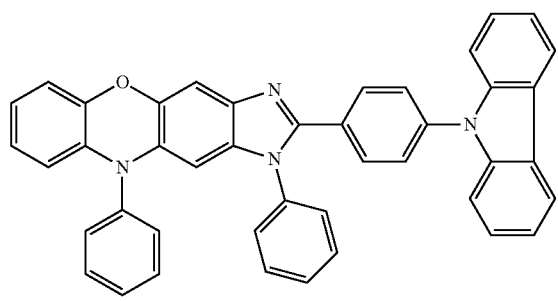 [SMILES: c1ccc(N2c3ccccc3Oc3cc4nc(-c5ccc(-n6c7ccccc7c7ccccc76)cc5)n(-c5ccccc5)c4cc32)cc1]
110

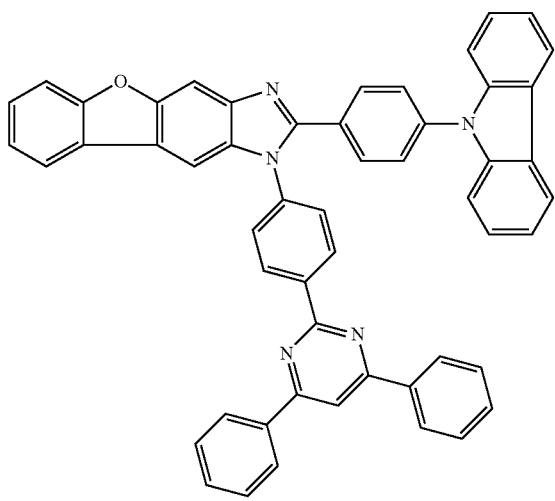 [SMILES: c1ccc(-c2cc(-c3ccccc3)nc(-c3ccc(-n4c(-c5ccc(-n6c7ccccc7c7ccccc76)cc5)nc5cc6oc7ccccc7c6cc54)cc3)n2)cc1]
111
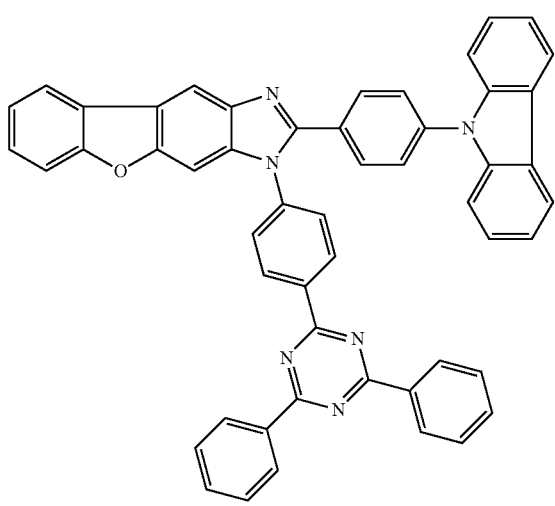 [SMILES: c1ccc(-c2nc(-c3ccccc3)nc(-c3ccc(-n4c(-c5ccc(-n6c7ccccc7c7ccccc76)cc5)nc5cc6c(cc54)oc4ccccc46)cc3)n2)cc1]
112
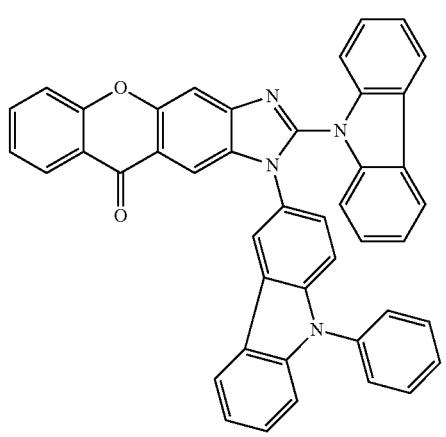 [SMILES: O=c1c2ccccc2oc2cc3nc(-n4c5ccccc5c5ccccc54)n(-c4ccc5c(c4)c4ccccc4n5-c4ccccc4)c3cc12]
113

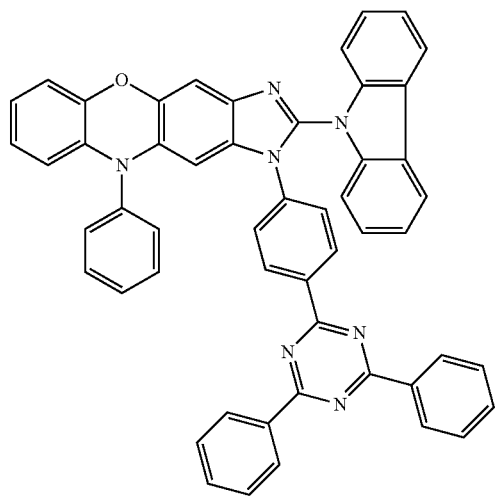 [SMILES: c1ccc(-c2nc(-c3ccccc3)nc(-c3ccc(-n4c(-n5c6ccccc6c6ccccc65)nc5cc6c(cc54)N(c4ccccc4)c4ccccc4O6)cc3)n2)cc1]
114
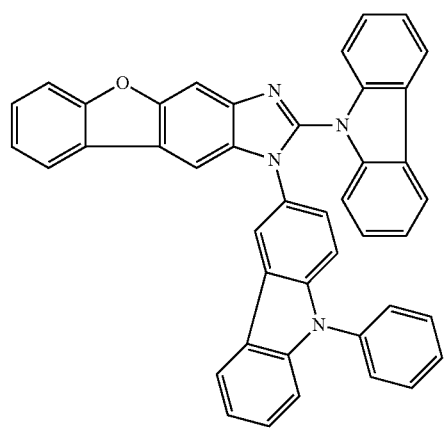 [SMILES: c1ccc(-n2c3ccccc3c3cc(-n4c(-n5c6ccccc6c6ccccc65)nc5cc6oc7ccccc7c6cc54)ccc32)cc1]
115
116

-continued
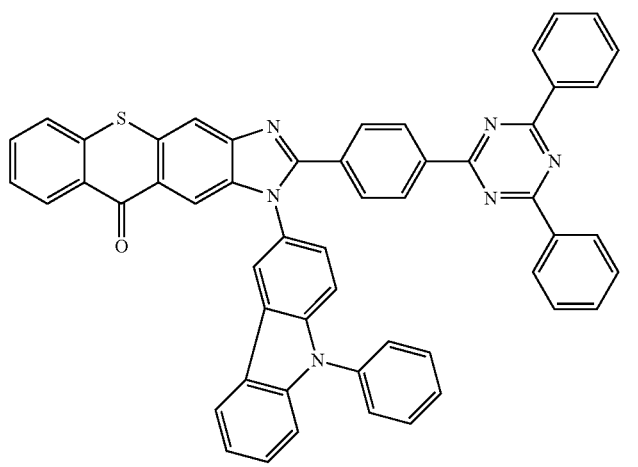 [SMILES: O=c1c2ccccc2sc2cc3nc(-c4ccc(-c5nc(-c6ccccc6)nc(-c6ccccc6)n5)cc4)n(-c4ccc5c(c4)c4ccccc4n5-c4ccccc4)c3cc12]
117
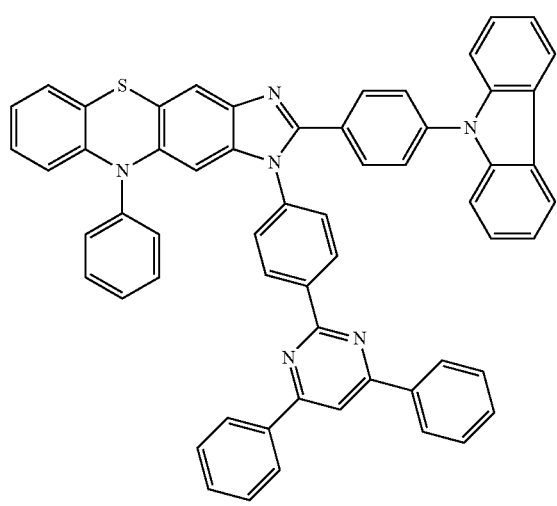 [SMILES: c1ccc(-c2cc(-c3ccccc3)nc(-c3ccc(-n4c(-c5ccc(-n6c7ccccc7c7ccccc76)cc5)nc5cc6c(cc54)N(c4ccccc4)c4ccccc4S6)cc3)n2)cc1]
118
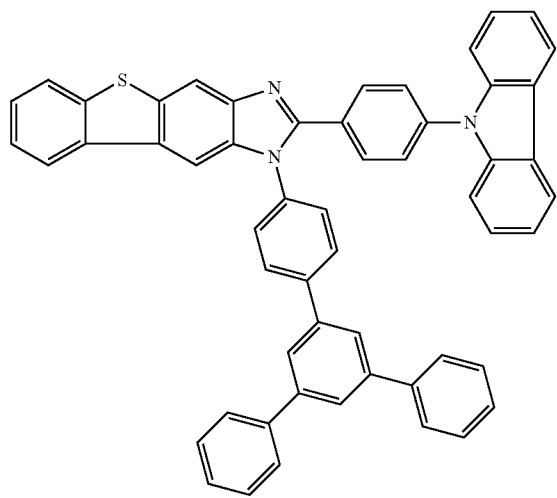 [SMILES: c1ccc(-c2cc(-c3ccccc3)cc(-c3ccc(-n4c(-c5ccc(-n6c7ccccc7c7ccccc76)cc5)nc5cc6sc7ccccc7c6cc54)cc3)c2)cc1]
119

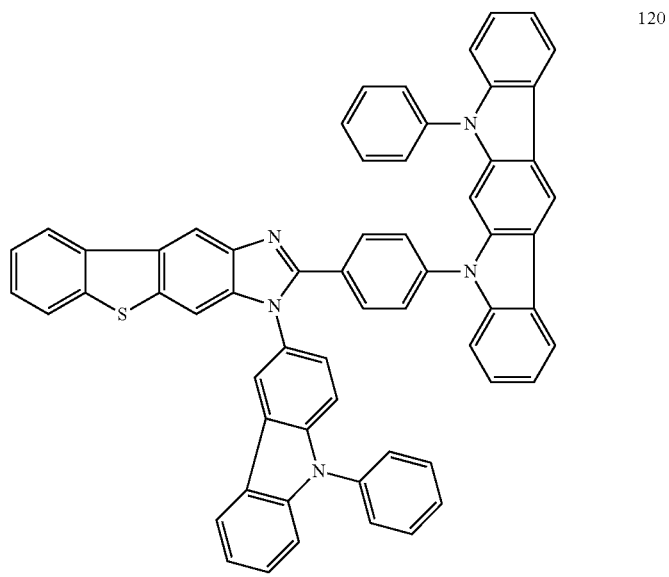
120
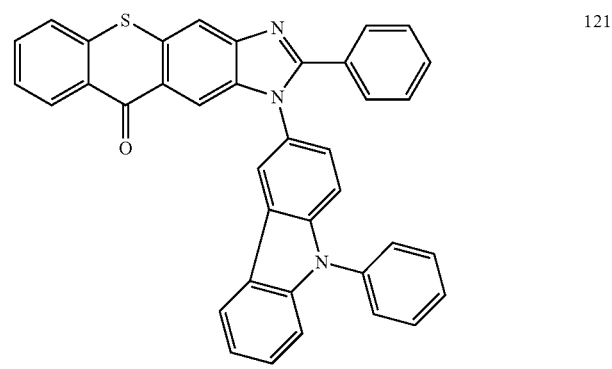
121
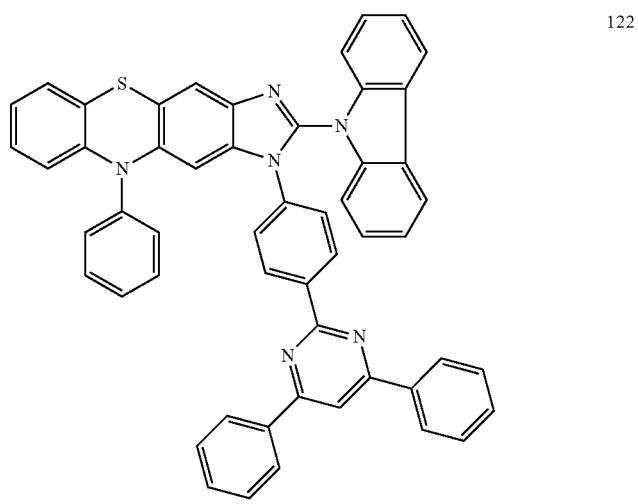
122

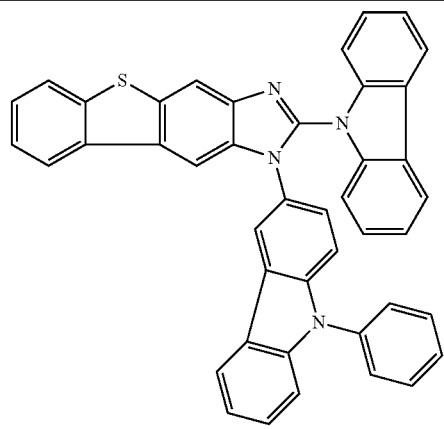

123

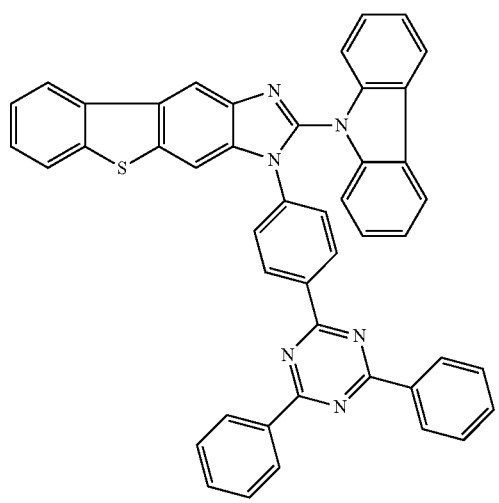 [SMILES: c1ccc(-c2nc(-c3ccccc3)nc(-c3ccc(-n4c(-n5c6ccccc6c6ccccc65)nc5cc6c(cc54)sc4ccccc46)cc3)n2)cc1]

124

The compounds can be prepared by synthesis steps known from the prior art. Use is made here, inter alia, of metal-catalysed coupling reactions, such as Buchwald coupling and Suzuki coupling. Furthermore, condensation reactions are used here for the formation of heteroaromatic rings. Again furthermore, nucleophilic substitution reactions on electron-deficient heteroaromatic compounds are used here.

One possible, preferred route for the preparation of compounds of the formula (I) is shown in Scheme 1 below.

Scheme 1

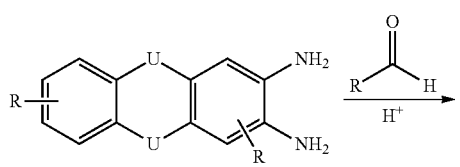

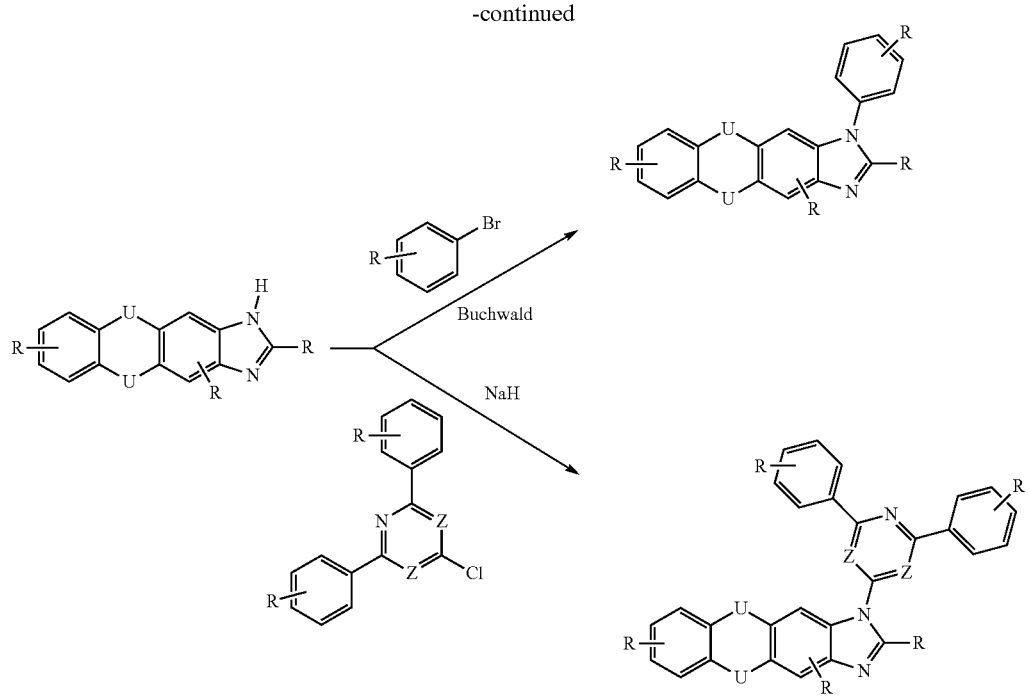

Z = C or N
R = organic radical
U = e.g. single bond, NR, O, C═O or P(═O)R

In a first step, the heteroaromatic five-membered ring is formed via a condensation reaction. The synthesis of an imidazole ring is shown, but other heteroaromatic five-membered rings in compounds of the formula (I) can also be formed in this or in analogous manner.

In a following step, either an aryl or heteroaryl group can be introduced into the molecule via a Buchwald coupling, or an electron-deficient heteroaryl group can be introduced via a nucleophilic substitution reaction, by deprotonation on the nitrogen atom of the benzimidazole.

In this way, a multiplicity of different aryl or heteroaryl groups can be introduced on the skeleton. A plurality of the above-mentioned coupling reactions can be carried out here, or a single coupling reaction can be carried out multiple times, for example a double Buchwald coupling in the case of the presence of two amino functions.

Analogously to the syntheses shown in Scheme 1, the compounds of the formula (I) can also be synthesised with variation of the substituents shown. For example, similar heterocyclic groups, such as pyridinyl and pyrimidinyl, can be introduced instead of triazine. Likewise, biphenyl, terphenyl, naphthyl, fluorenyl, carbazolyl and similar substituents can be introduced instead of the phenyl radical.

Furthermore, the coupling reactions can be followed by further functionalisation reactions in order to obtain the final compound of the formula (I).

A further possible method for the preparation of compounds of the formula (I) is shown in Scheme 2 below.

Scheme 2

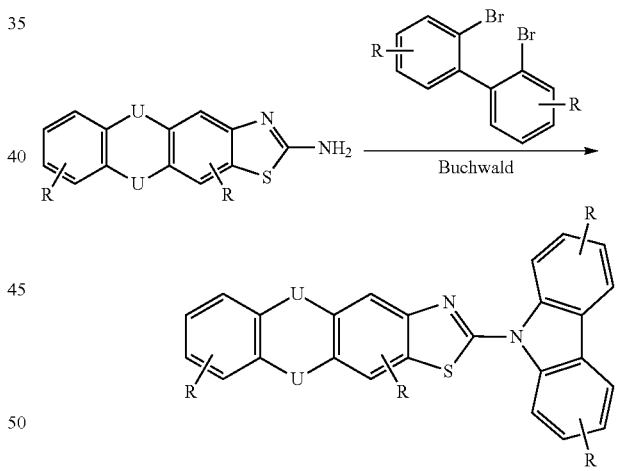

R = organic radical
U = e.g. single bond, NR, O, C═O or P(═O)R

This starts from a heterocyclic compound carrying a primary amino group. Such compounds can either be prepared easily or are in many cases also commercially available. This compound is subsequently reacted with a dibromide in a Buchwald reaction. A carbazole derivative is thereby bonded to the heteroaromatic skeleton.

The invention thus furthermore relates to a process for the preparation of a compound of the formula (I-1), characterised in that firstly the heteroaromatic skeleton is prepared, preferably using one or more condensation reactions, and subsequently one or more aryl or heteroaryl groups are introduced, preferably using Buchwald couplings or nucleophilic aromatic substitution reactions.

The compounds of the formula (I-1) described above, in particular compounds which are substituted by reactive leaving groups, such as bromine, iodine, chlorine, boronic acid or boronic acid ester, can be used as monomers for the production of corresponding oligomers, dendrimers or polymers. Suitable reactive leaving groups are, for example, bromine, iodine, chlorine, boronic acids, boronic acid esters, amines, alkenyl or alkynyl groups having a terminal C—C double bond or C—C triple bond, oxiranes, oxetanes, groups which undergo a cycloaddition, for example a 1,3-dipolar cycloaddition, such as, for example, dienes or azides, carboxylic acid derivatives, alcohols and silanes.

The invention therefore furthermore relates to oligomers, polymers or dendrimers containing one or more compounds of the formula (I-1), where the bond(s) to the polymer, oligomer or dendrimer may be localised at any desired positions in formula (I-1) which are substituted by $R^1$ or $R^2$. Depending on the linking of the compound of the formula (I-1) the compound is a constituent of a side chain of the oligomer or polymer or a constituent of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I-1) may be linked directly to one another or they may be linked to one another via a divalent group, for example via a substituted or unsubstituted alkylene group, via a heteroatom or via a divalent aromatic or heteroaromatic group. In branched and dendritic structures, for example, three or more units of the formula (I-1) may be linked via a trivalent or polyvalent group, for example via a trivalent or polyvalent aromatic or heteroaromatic group, to form a branched or dendritic oligomer or polymer.

The same preferences as described above for compounds of the formula (I-1) apply to the recurring units of the formula (I-1) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which leads to recurring units of the formula (I-1) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

For the processing of the compounds according to the invention from the liquid phase, for example by spin coating or by printing processes, formulations of the compounds according to the invention are necessary. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetol, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore furthermore relates to a formulation, in particular a solution, dispersion or emulsion, comprising at least one compound of the formula (I-1) or at least one polymer, oligomer or dendrimer containing at least one unit of the formula (I-1), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I) are suitable for use in electronic devices, in particular in organic electroluminescent devices (OLEDs). Depending on the substitution, the compounds are employed in different functions and layers. The compounds of the formula (I) are preferably used in electron-transporting layers and/or in emitting layers. In the latter, they are preferably used as matrix material, particularly preferably as matrix material for phosphorescent emitters.

The invention therefore furthermore relates to the use of a compound of the formula (I) in an electronic device. The electronic device here is preferably selected from the group consisting of organic integrated circuits (OICs), organic field-effect transistors (OFETs), organic thin-film transistors (OTFTs), organic light-emitting transistors (OFETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention relates, as already indicated above, to an electronic device comprising anode, cathode and at least one organic layer comprising at least one compound of the formula (I). The electronic device here is preferably selected from the devices mentioned above. It is particularly preferably an organic electroluminescent device comprising anode, cathode and at least one emitting layer, characterised in that at least one organic layer, which may be an emitting layer, an electron-transport layer or another layer, comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, interlayers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The sequence of the layers of the device is preferably the following: anode/hole-injection layer/hole-transport layer/emitting layer/electron-transport layer/electron-injection layer/cathode.

This preferably applies to devices in the case of which the layers are applied by gas-phase deposition.

For devices in the case of which the layers are applied from solution, the following layer sequence is preferably used:

anode/hole-injection layer/interlayer/emitting layer/cathode.

Instead of the term hole-injection layer, the term buffer layer can also be used synonymously here. Instead of the term interlayer, the term hole-transport layer can also be used synonymously here. It should again be pointed out that not all the said layers have to be present, and/or that further layers may additionally be present.

The organic electroluminescent device according to the invention may comprise a plurality of emitting layers. These emission layers in this case particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where at least one of these layers preferably comprises at least one compound of the formula (I) and where the three layers exhibit blue, green and orange or red emission (for the basic structure see, for example, WO 2005/011013). Alternatively and/or additionally, the compound according to the invention may also be present in the electron-transport layer or in another layer. It should be noted that, for the generation of white light, an emitter compound used individually which emits in a broad wavelength range may also be suitable instead of a plurality of emitter compounds emitting in colour.

The electronic device preferably comprises the compound of the formula (I) in an electron-transport layer. For the purposes of the present application, an electron-transport layer is taken to mean a layer which is located between cathode and emitting layer.

In the literature, hole-blocking layers and electron-injection layers are known as subtypes of electron-transport layers. For the purposes of the present application, these are taken to be encompassed by the term electron-transport layer. In particular, a hole-blocking layer denotes a layer which is directly adjacent to the emitting layer on the cathode side, consists of a material having a low HOMO and has good electron-transport properties. The HOMO here is preferably lower than the HOMO of the emitting layer. An electron-injection layer is taken to mean a layer which is directly adjacent to the cathode and which simplifies the entry of electrons into the organic material from the cathode.

The electron-transport layer comprising the compound of the formula (I) may comprise the compound as pure material or in combination with one or more further compounds. If further compounds are present, these are preferably present in a small proportion. Such components present in secondary amounts in the electron-transport layer are called dopants, in particular n-dopants, if they are strong reducing agents, preferably if they are stronger reducing agents than the principal component of the electron-transport layer.

In a further embodiment of the present invention, the electronic device comprises the compound of the formula (I) in an emitting layer as matrix material in combination with one or more dopants, preferably phosphorescent dopants.

The term phosphorescent dopants typically encompasses compounds in which the light emission takes place through a spin-forbidden transition, for example a transition from an excited triplet state or a state having a higher spin quantum number, for example a quintet state.

Suitable phosphorescent dopants are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent dopants used are preferably compounds which contain copper, molybdenum, tungsten, rhenium, ruthenium, osmium, rhodium, iridium, palladium, platinum, silver, gold or europium, in particular compounds which contain iridium, platinum or copper.

For the purposes of the present application, all luminescent iridium, platinum or copper complexes are regarded as phosphorescent compounds. Examples of phosphorescent dopants are indicated in the following section.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the larger.

The proportion of the matrix material in the emitting layer is in this case between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopants is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

An emitting layer of an organic electroluminescent device may also comprise systems comprising a plurality of matrix materials (mixed-matrix systems) and/or a plurality of dopants. In this case too, the dopants are generally the materials whose proportion in the system is the smaller and the matrix materials are the materials whose proportion in the system is the larger. In individual cases, however, the proportion of an individual matrix material in the system may be smaller than the proportion of an individual dopant.

In a further preferred embodiment of the invention, the compound of the formula (I) is used as a component of mixed-matrix systems. The mixed-matrix systems preferably comprise two or three different matrix materials, particularly preferably two different matrix materials. One of the two materials here is preferably a material having hole-transporting properties and the other material is a material having electron-transporting properties. However, the desired electron-transporting and hole-transporting properties of the mixed-matrix components may also be combined principally or completely in a single mixed-matrix components, where the further mixed-matrix component(s) fulfil other functions. The two different matrix materials here may be present in a ratio of 1:50 to 1:1, preferably 1:20 to 1:1, particularly preferably 1:10 to 1:1 and very particularly preferably 1:4 to 1:1. Mixed-matrix systems are preferably employed in phosphorescent organic electroluminescent devices. More precise information on mixed-matrix systems is given, inter alia, in the application WO 2010/108579.

Particularly suitable matrix materials which can be used as matrix components of a mixed-matrix system in combination with the compounds according to the invention are selected from the preferred matrix materials for phosphorescent dopants indicated below or the preferred matrix materials for fluorescent dopants, depending on what type of dopant compound is employed in the mixed-matrix system.

Preferred phosphorescent dopants for use in mixed-matrix systems are the preferred phosphorescent dopants indicated below.

Preferred embodiments of the functional layers and of the functional materials of the device according to the invention follow:

Examples of phosphorescent dopants are revealed by the applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as are used in accordance with the prior art for phosphorescent OLEDs and as are known to the person skilled in the art in the area of organic electroluminescent devices are suitable for use in the devices according to the invention.

Explicit examples of phosphorescent dopants are shown in the following table.

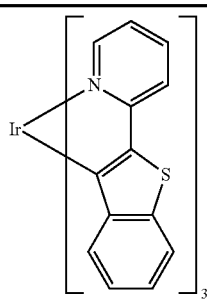

-continued

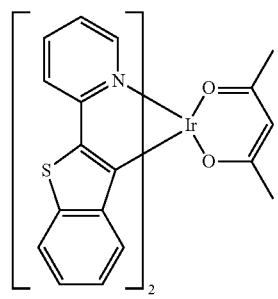

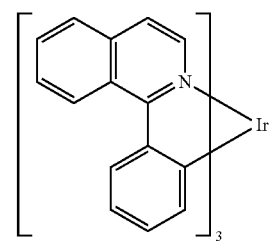

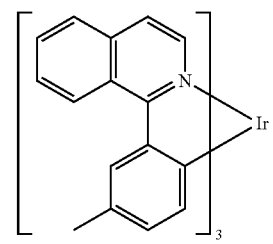

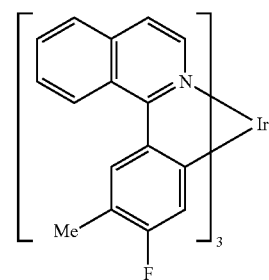

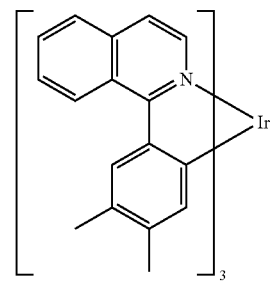

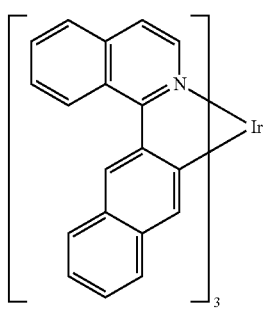
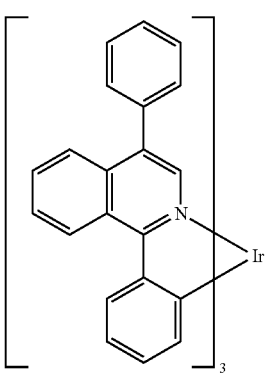
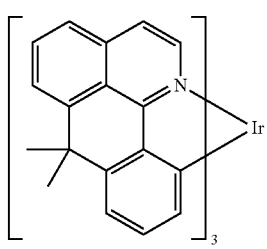
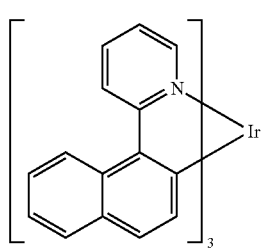
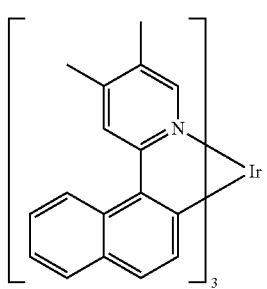
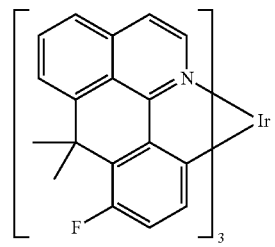
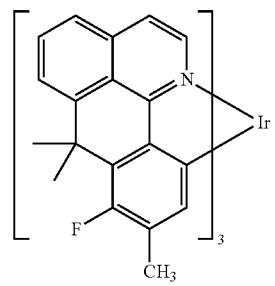
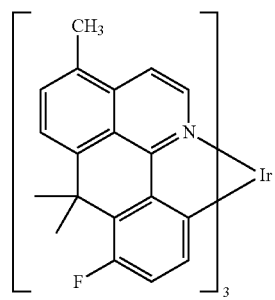
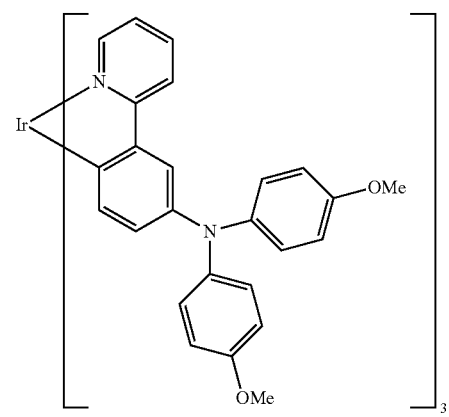
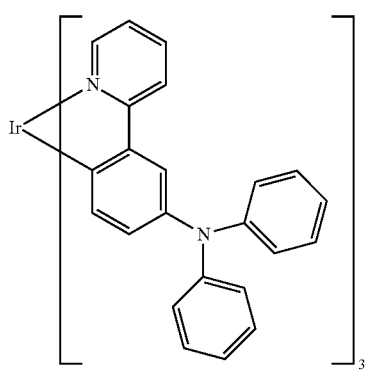

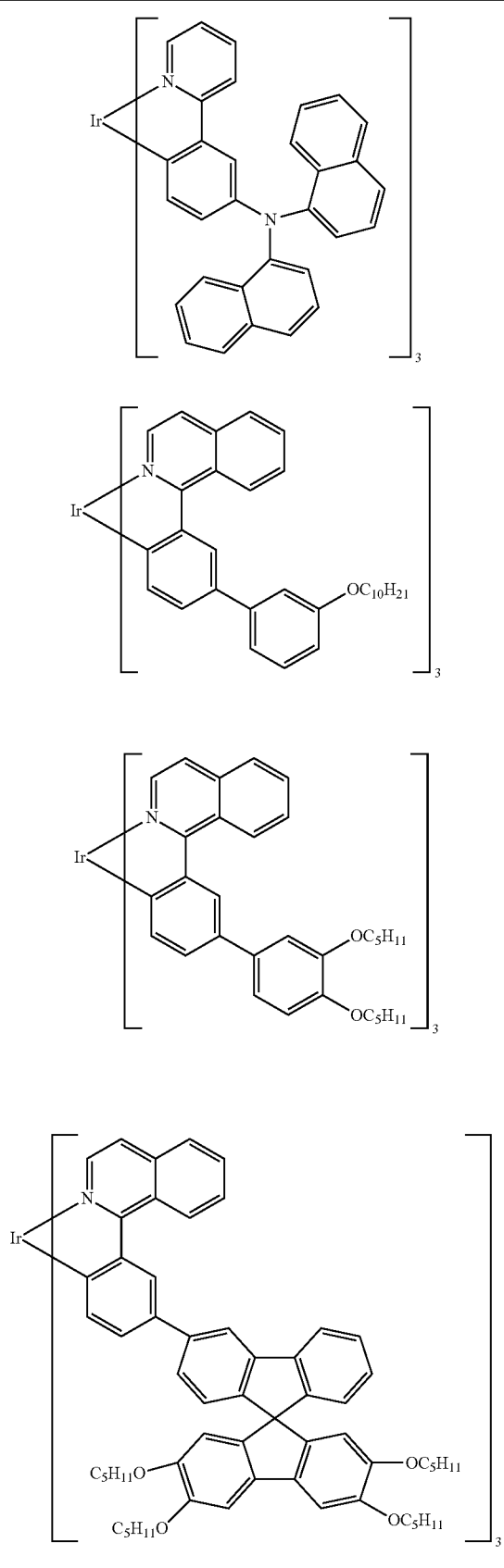
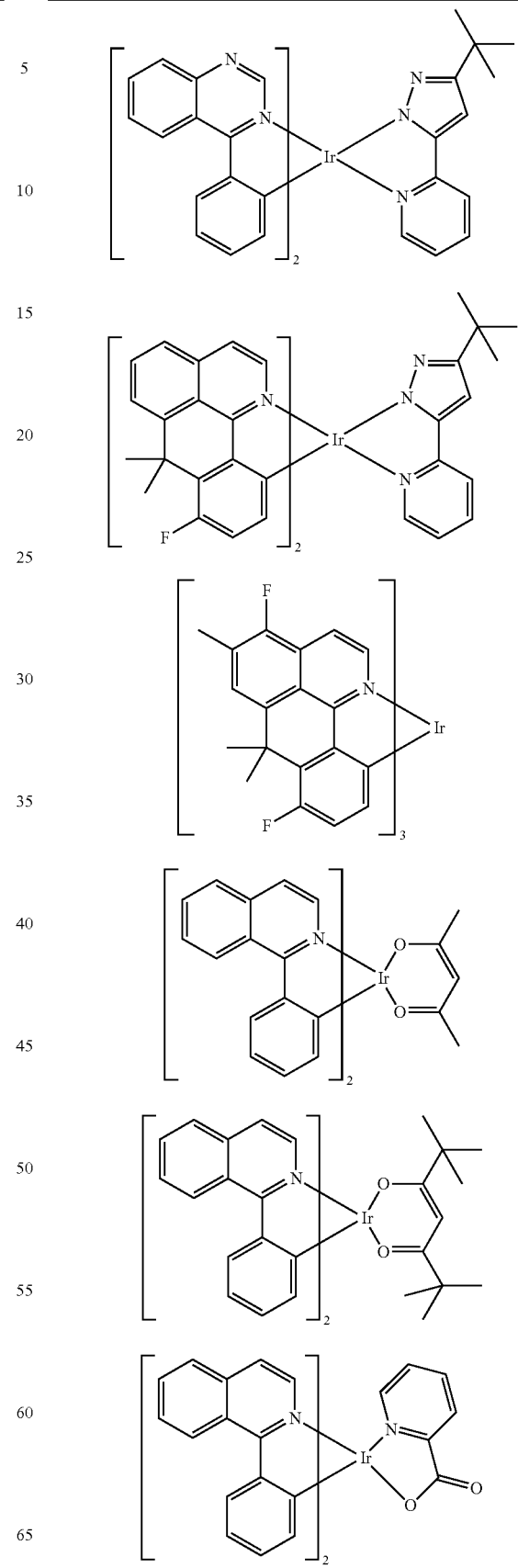

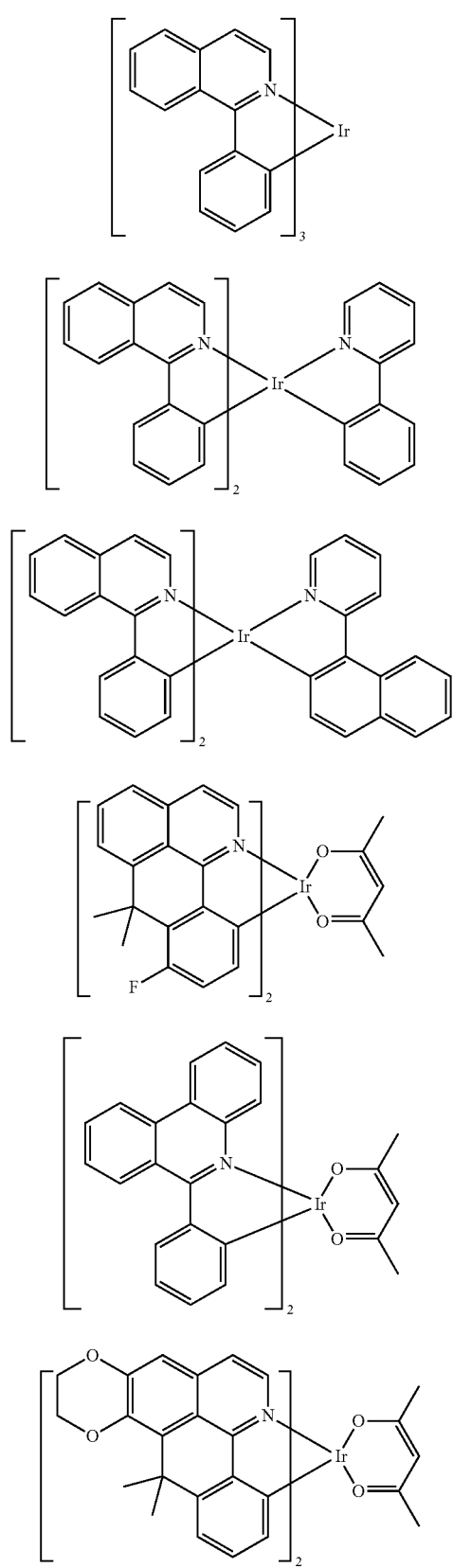
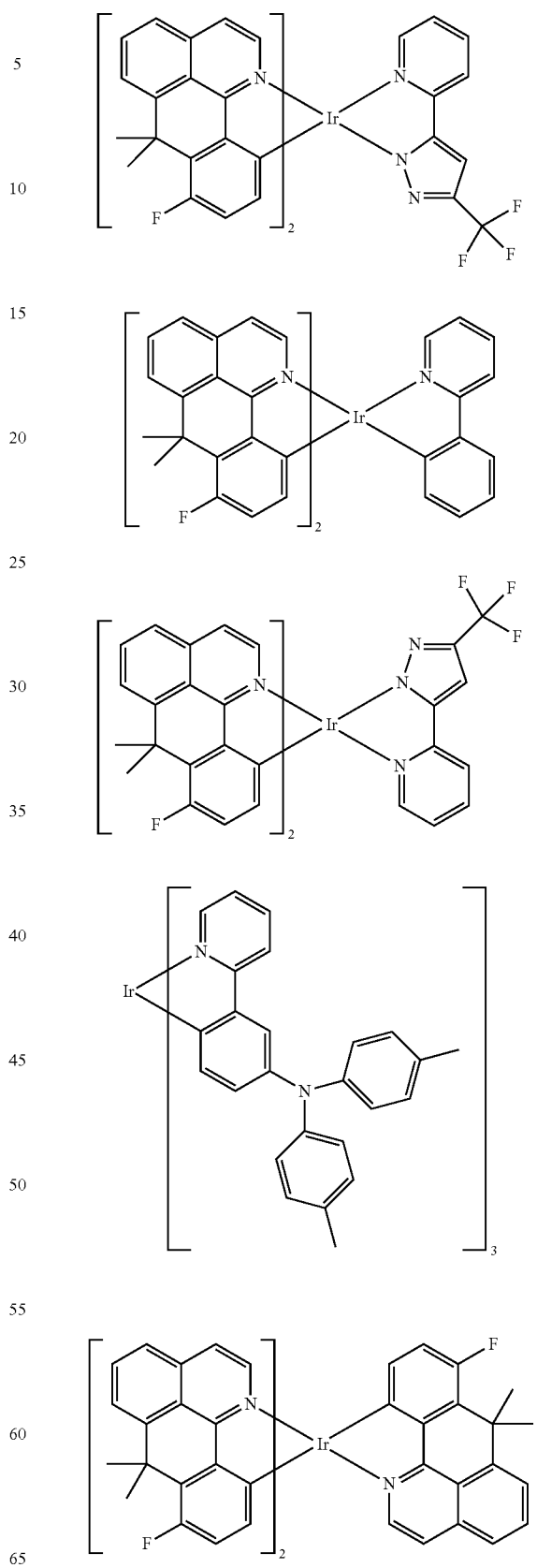

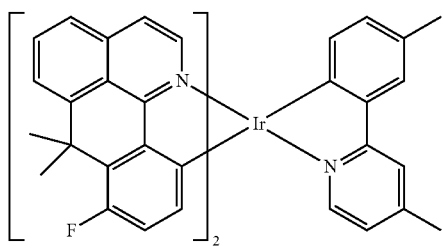
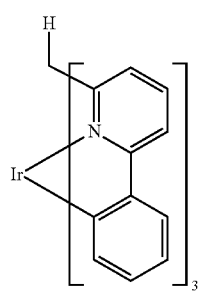
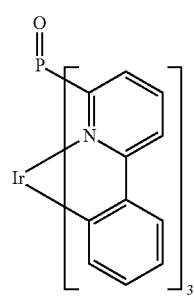
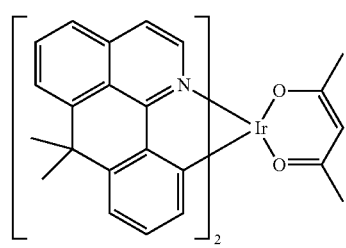
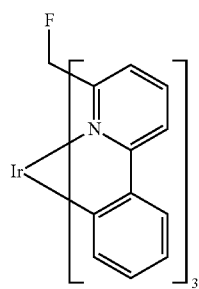
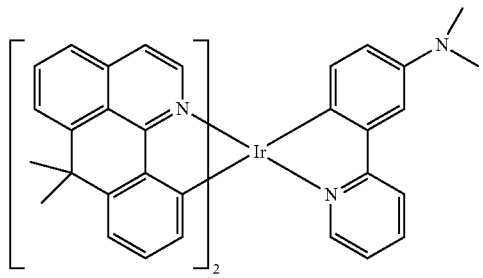
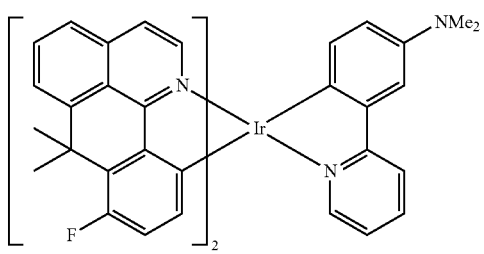
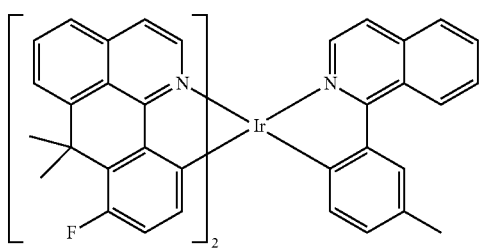
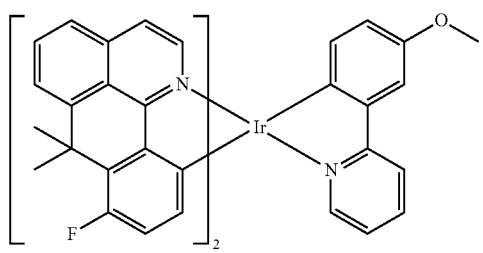
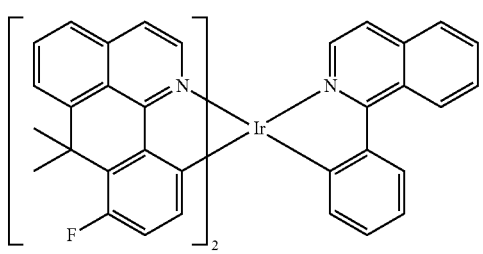
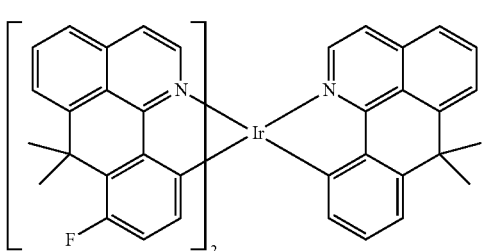

-continued
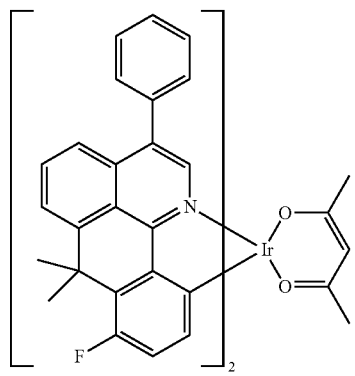
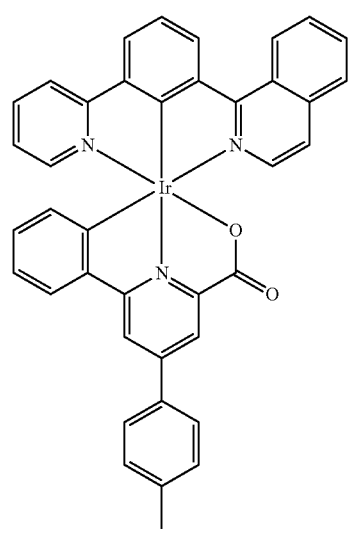
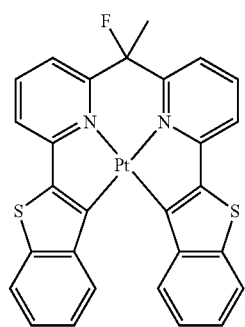
-continued
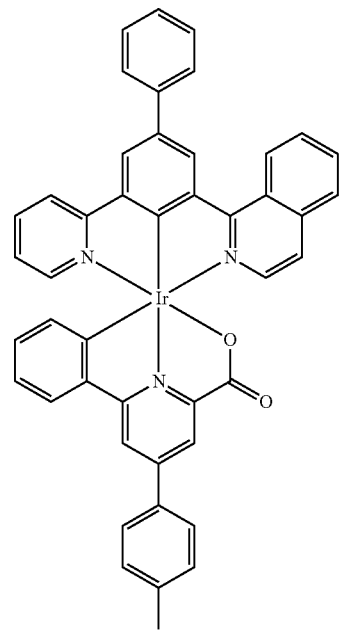
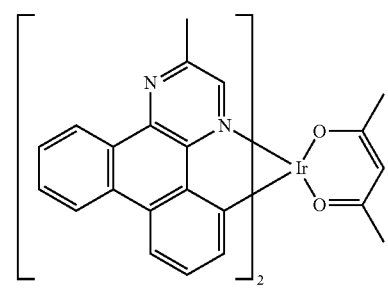
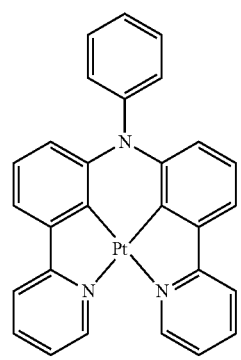
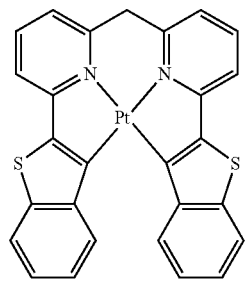

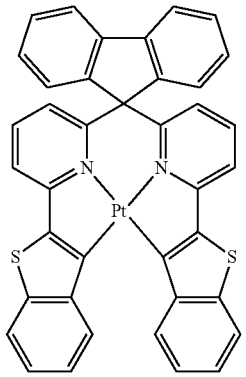
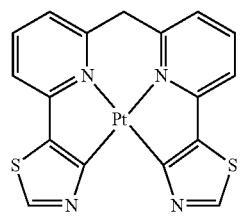
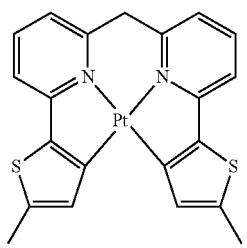
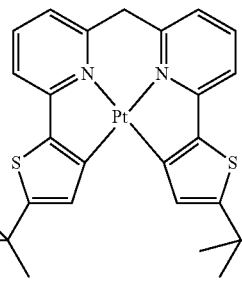
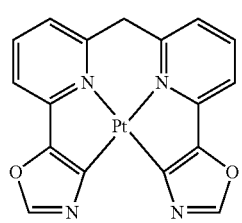
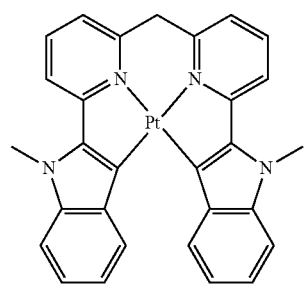
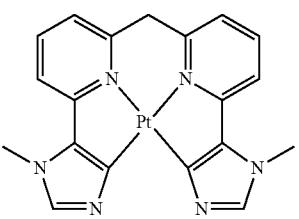
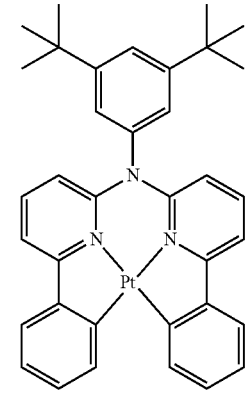
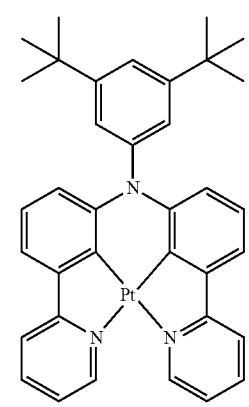
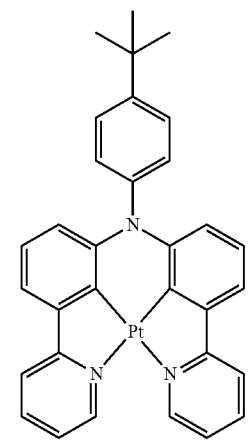

95
-continued
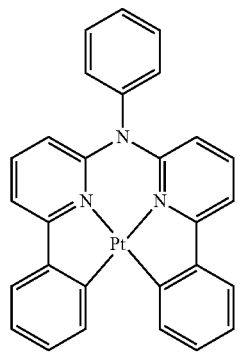
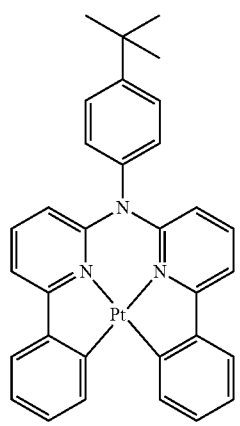
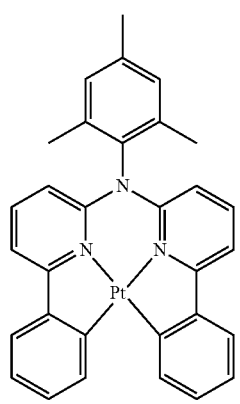
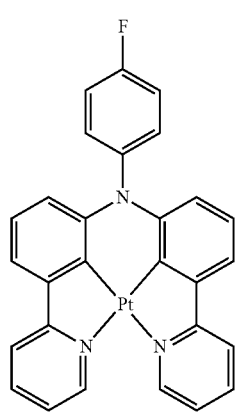
96
-continued
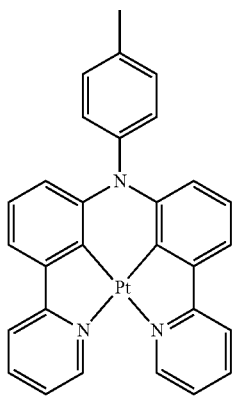
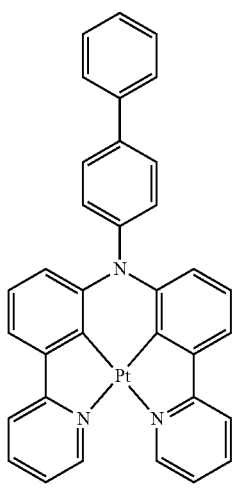
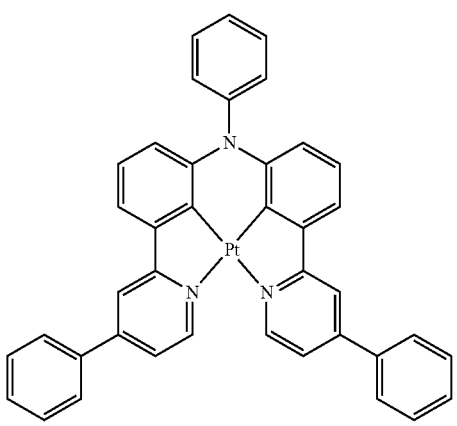

97
-continued
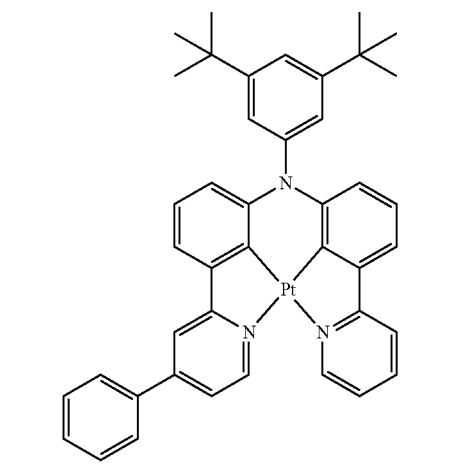
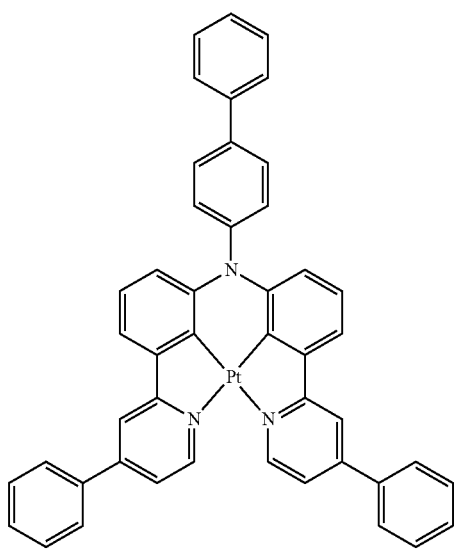
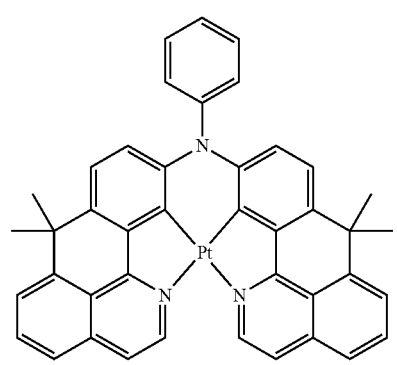
98
-continued
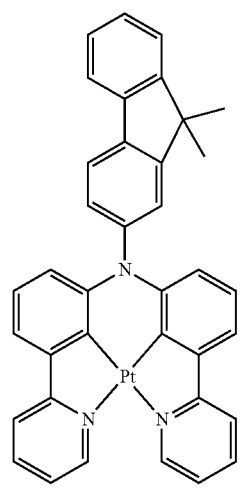
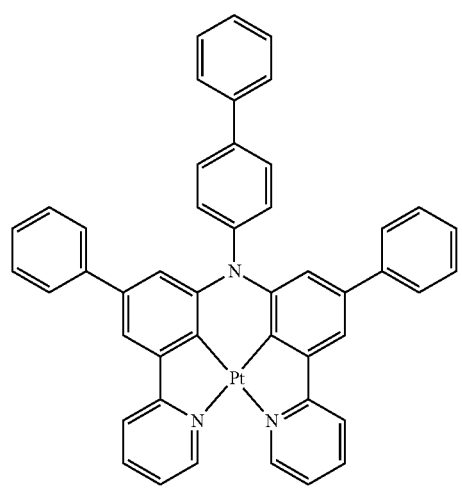
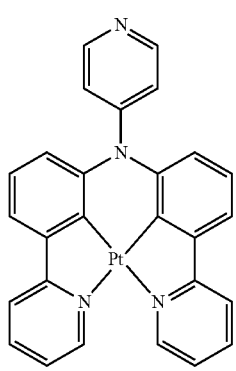

| 99 -continued | 100 -continued |
|---|---|
| 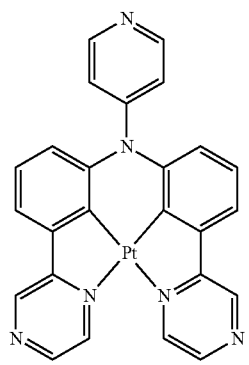<br><br>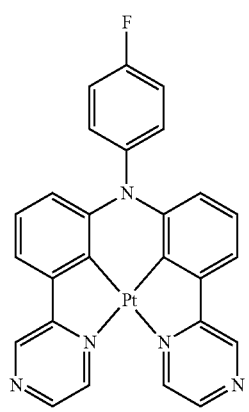<br><br>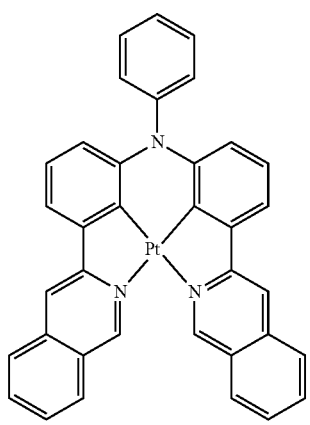<br><br>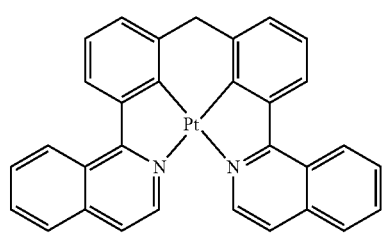 | 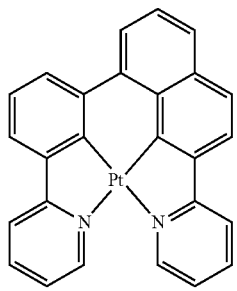<br><br>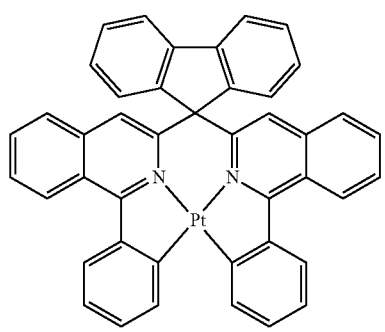<br><br>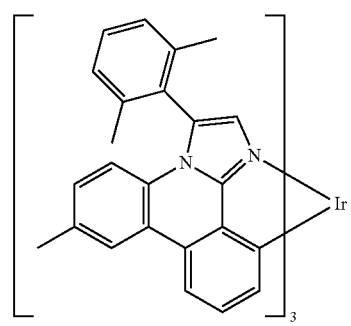<br><br>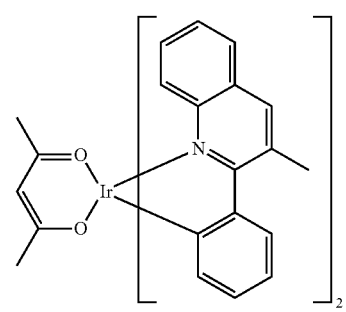<br><br>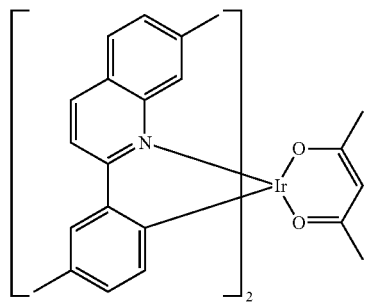 |

101
-continued
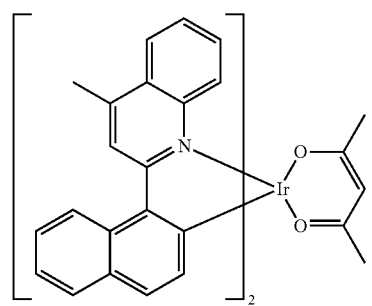
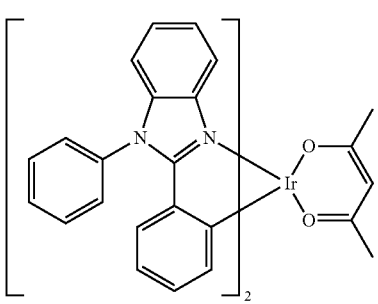
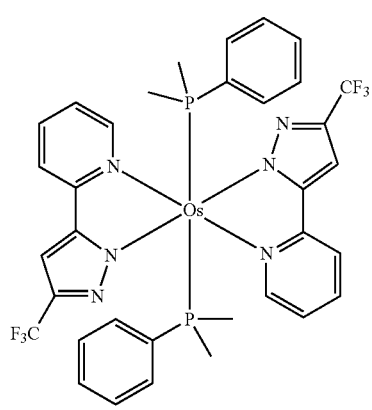
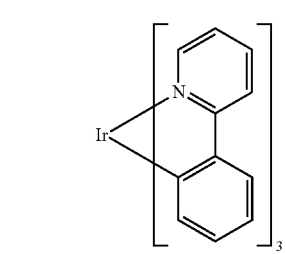
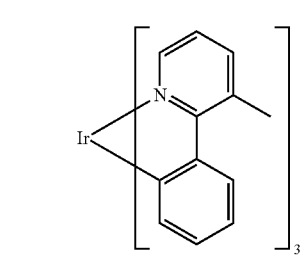
102
-continued
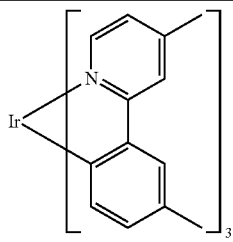
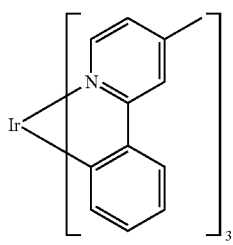
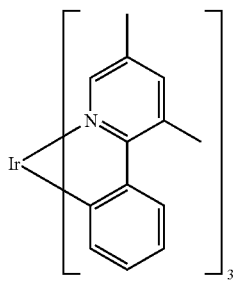
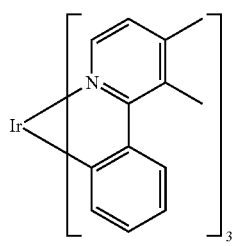
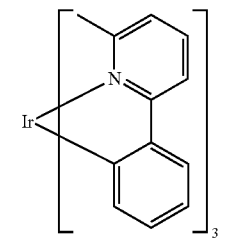
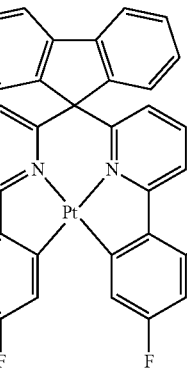

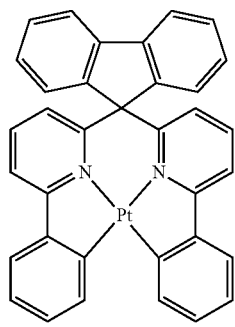
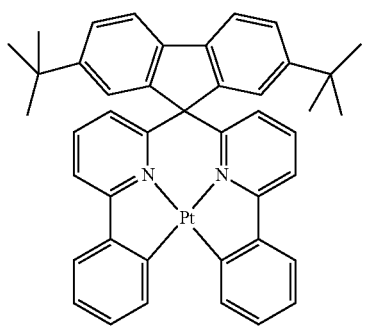
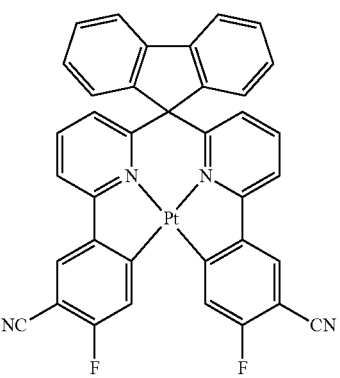
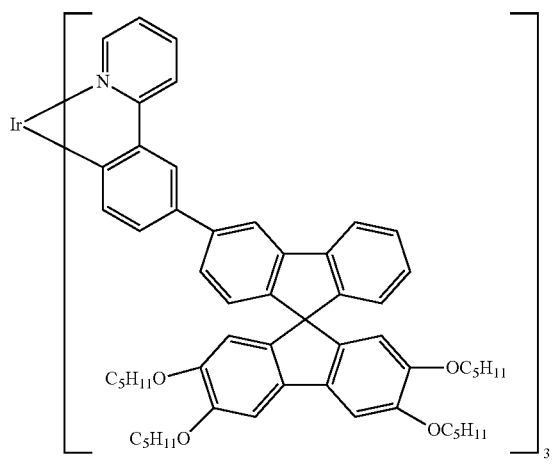
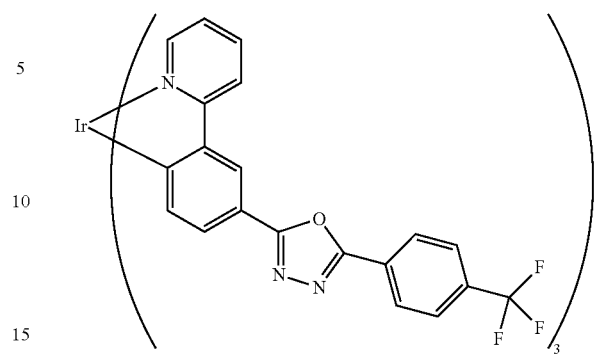
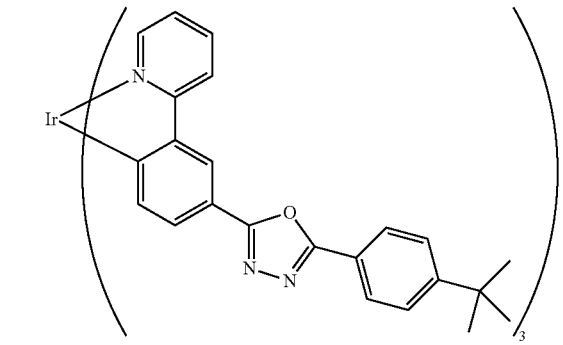
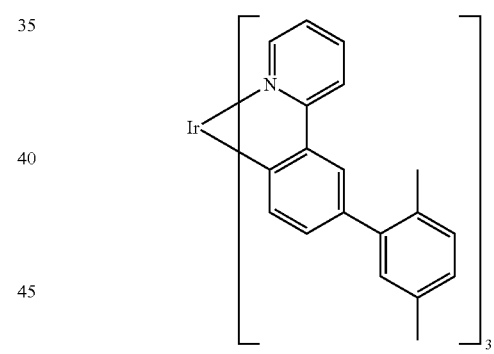
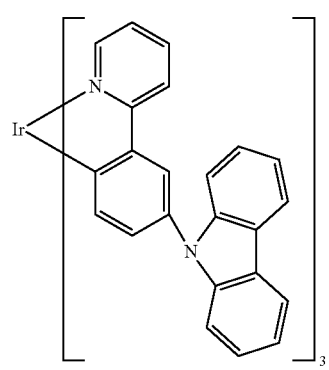

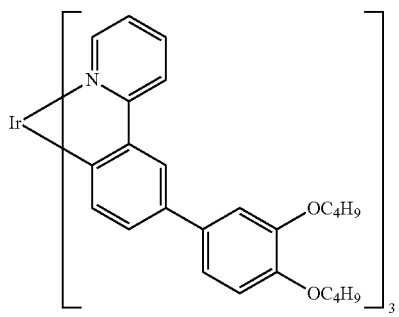
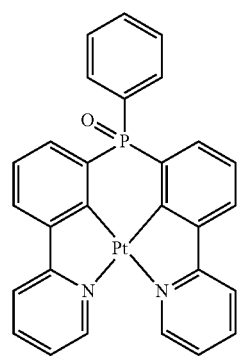
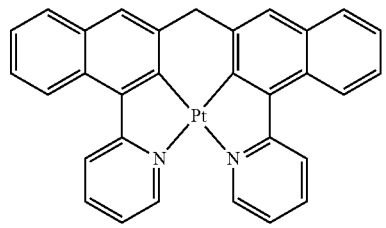
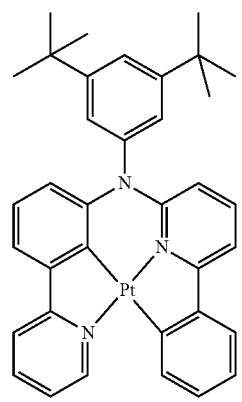
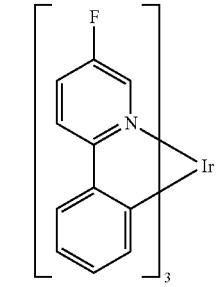
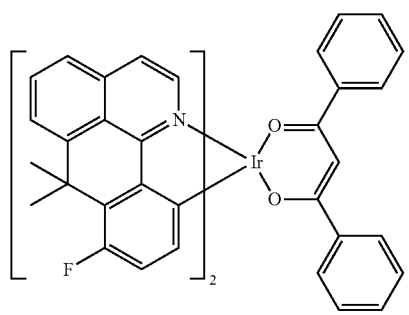
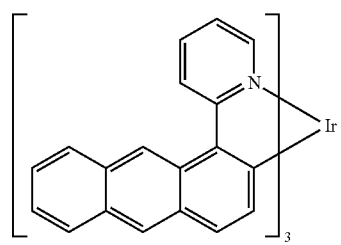
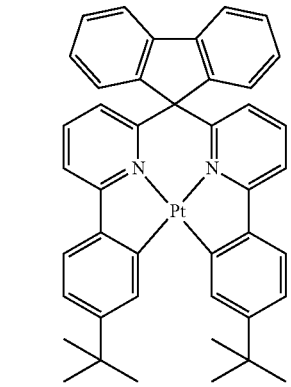
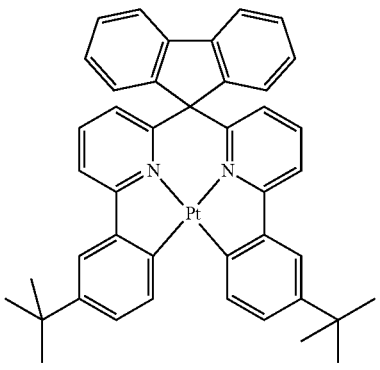

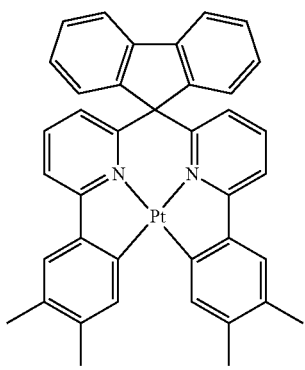
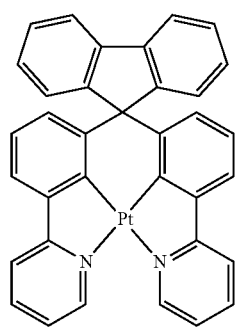
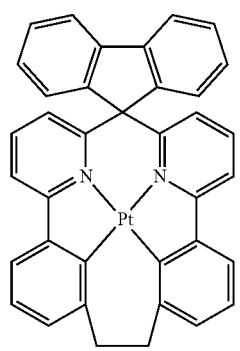
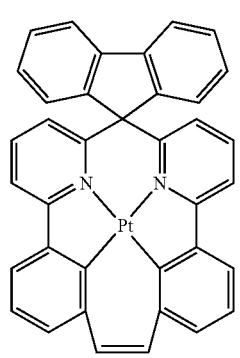
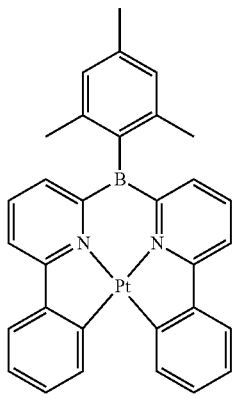
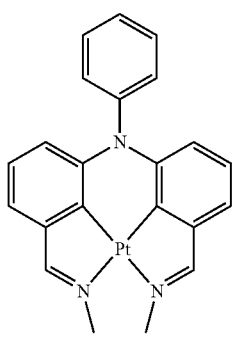
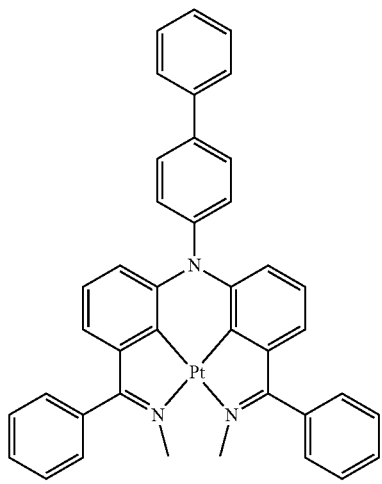
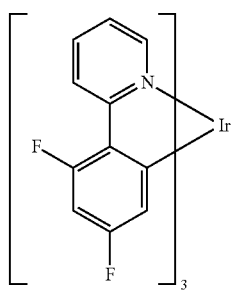

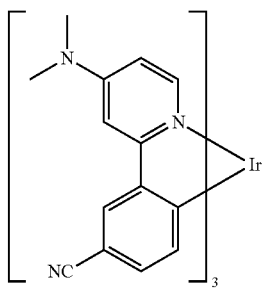
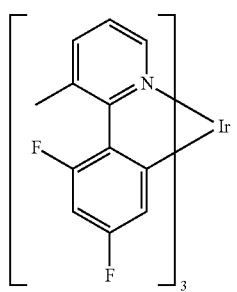
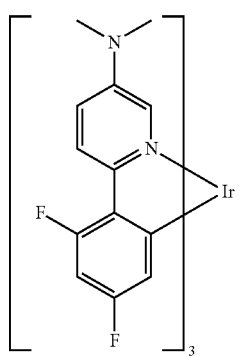
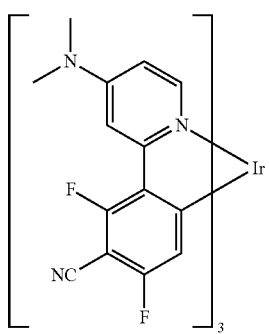
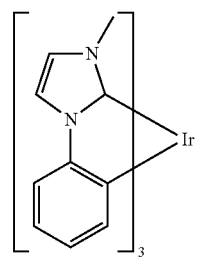
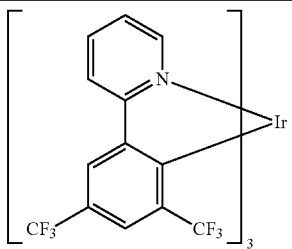
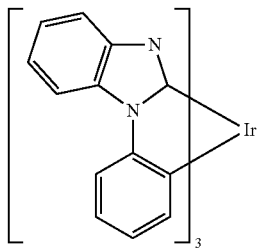
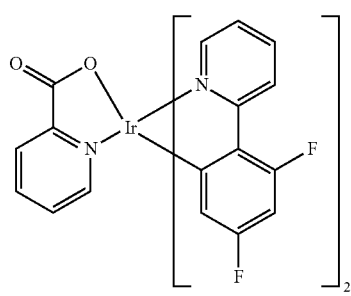
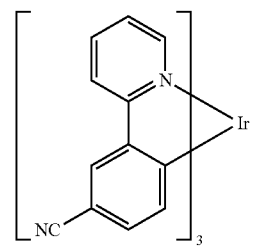
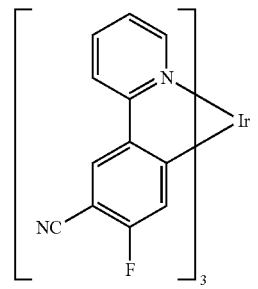
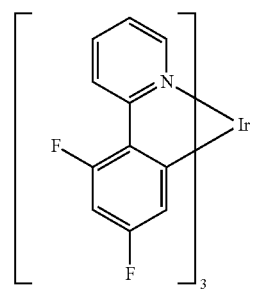

111
-continued
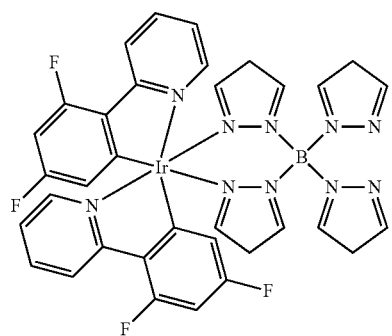
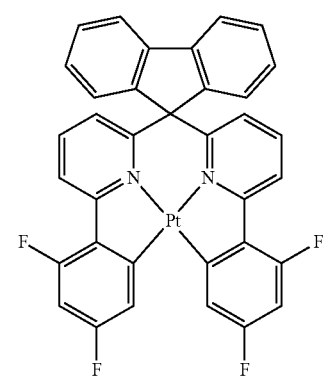
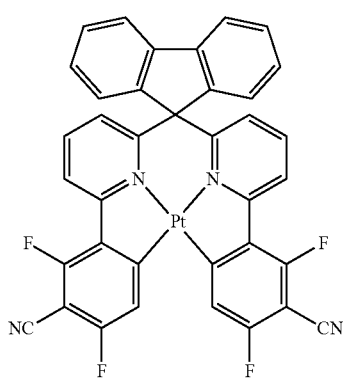
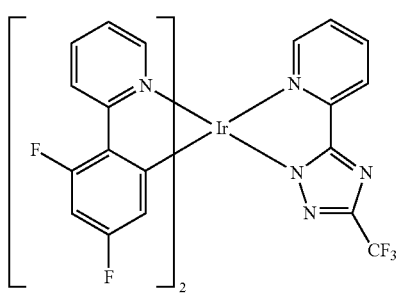
112
-continued
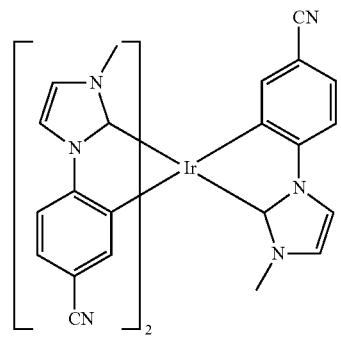
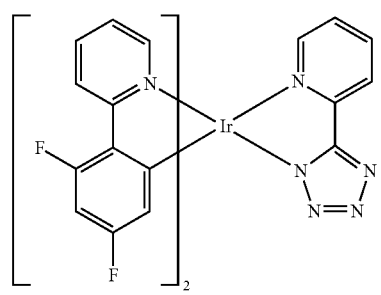
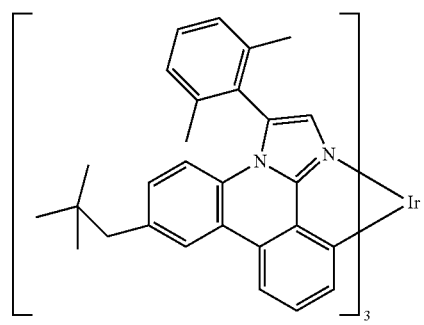
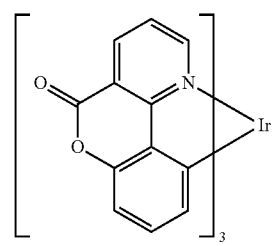
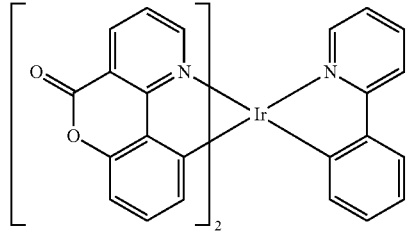

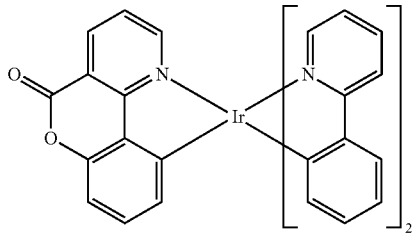

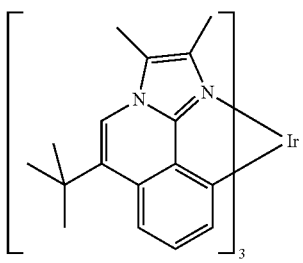

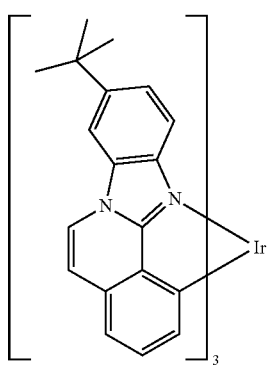

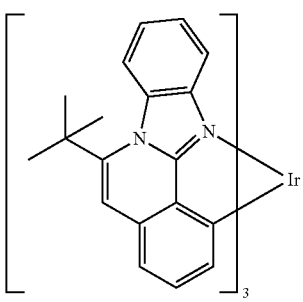

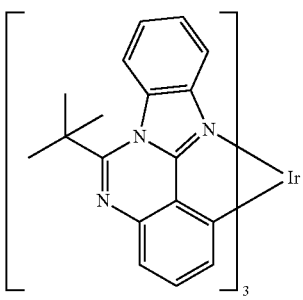

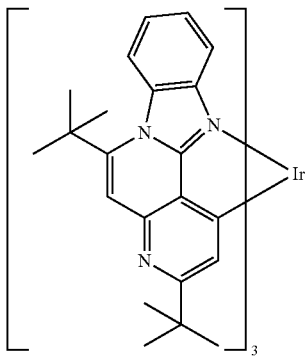

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are indenofluorenamines or indenofluorenediamines, for example in accordance with WO 2006/108497 or WO 2006/122630, benzoindenofluorenamines or benzoindenofluorenediamines, for example in accordance with WO 2008/006449, and dibenzoindenofluorenamines or dibenzoindenofluorenediamines, for example in accordance with WO 2007/140847, and the indenofluorene derivatives containing condensed aryl groups which are disclosed in WO 2010/012328.

Suitable matrix materials, preferably for fluorescent dopants, besides the compounds of the formula (I), are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopants, besides the compounds of the formula (I), are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, and diazaphosphole derivatives, for example in accordance with WO 2010/054730.

Besides the compounds of the formula (I), suitable charge-transport materials, as can be used in the hole-injection or hole-transport layer or electron-blocking layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

Besides the compounds of the formula (I), materials which can be used for the electron-transport layer are all materials as are used in accordance with the prior art as electron-transport materials in the electron-transport layer. Particularly suitable are aluminium complexes, for example $Alq_3$, zirconium complexes, for example $Zrq_4$, benzimidazole derivatives, triazine derivatives, pyrimidine derivatives, pyridine derivatives, pyrazine derivatives, quinoxaline derivatives, quinoline derivatives, oxadiazole derivatives, aromatic ketones, lactams, boranes, diazaphosphole derivatives and phosphine oxide derivatives. Furthermore suitable materials are derivatives of the above-mentioned compounds, as disclosed in JP 2000/053957, WO 2003/060956, WO 2004/028217, WO 2004/080975 and WO 2010/072300.

Materials which can be used in a hole-transport, hole-injection or electron-blocking layer of the electronic device according to the invention are indenofluorenamine derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449), dibenzoindenofluorenamines (for example in accordance with WO 07/140847), spirobifluorenamines (for example in accordance with WO 2012/034627 or the as yet unpublished EP 12000929.5), fluorenamines (for example in accordance with the as yet unpublished applications EP 12005369.9, EP 12005370.7 and EP 12005371.5), spirodibenzopyranamines (for example in accordance with WO 2013/083216) and dihydroacridine derivatives (for example in accordance with WO 2012/150001).

The cathode of the electronic device preferably comprises metals having a low work function, metal alloys or multi-layered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers. Furthermore, the anode may also consist of a plurality of layers, for example of an inner layer of ITO and an outer layer of a metal oxide, preferably tungsten oxide, molybdenum oxide or vanadium oxide.

During production, the electronic device is appropriately (depending on the application) structured, provided with contacts and finally sealed, since the lifetime of the devices according to the invention is shortened in the presence of water and/or air.

In a preferred embodiment, the electronic device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

The present invention therefore furthermore relates to the use of the compounds according to the invention and devices comprising the compounds for the treatment, prophylaxis and diagnosis of diseases. The present invention still furthermore relates to the use, of the compounds according to the invention and devices comprising the compounds for the treatment and prophylaxis of cosmetic conditions.

Details regarding the use of organic electroluminescent devices in light therapy and in the treatment and prophylaxis of cosmetic conditions are disclosed in WO 2011/069590 and WO 2011/110277. The disclosure content in this respect is incorporated into the disclosure content of the present application.

Phototherapy or light therapy is used in many medical and/or cosmetic areas. The compounds according to the invention and the devices comprising these compounds can therefore be employed for the therapy and/or prophylaxis and/or diagnosis of all diseases and/or in cosmetic applications for which the person skilled in the art considers the use of phototherapy. Besides irradiation, the term phototherapy also includes photodynamic therapy (PDT) as well as disinfection and sterilisation in general.

WORKING EXAMPLES

The following working examples serve to illustrate the invention. They should not be interpreted as restrictive.
A) Synthesis Examples The following syntheses are carried out, unless indicated otherwise, under a protective-gas atmosphere in dried solvents.
Synthesis of Precursors:

Example Int-1a

2-Phenyl-3,9-dihydro-1,3,9-triazacyclopenta[b]-fluorene

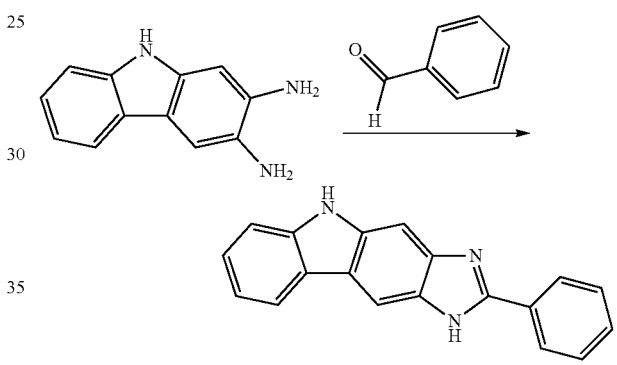

5 g (50 mmol) of benzaldehyde is added dropwise to 9.8 g (50 mmol) of 9H-carbazole-2,3-diamine in 300 ml of DMF and 10 ml of conc. sulfuric acid, and the mixture is stirred at room temperature for 2 h. The mixture is added to 500 g of ice and extracted with dichloromethane. The organic phase is washed with 4×50 ml of $H_2O$, dried over $MgSO_4$, and the solvents are removed in vacuo. The pure product is obtained by recrystallisation. The content of product according to HPLC is 98% with an overall yield of 7.3 g (25 mmol, 52%).

The following compounds can be obtained analogously:

| Ex. | Starting material | Starting material | Product |
|---|---|---|---|
| Int-1b<br>86439-50-1 | 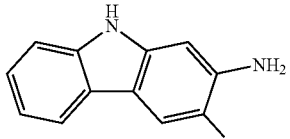 | 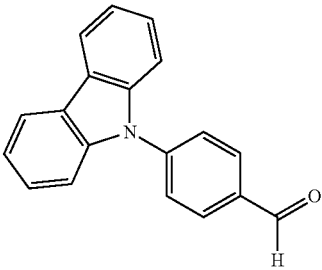 [SMILES: O=Cc1ccc(-n2c3ccccc3c3ccccc32)cc1] | 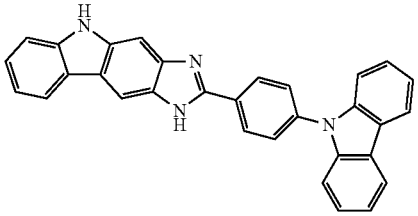 [SMILES: c1ccc2c(c1)[nH]c1cc3nc(-c4ccc(-n5c6ccccc6c6ccccc65)cc4)[nH]c3cc12] |

-continued
| Ex. | Starting material | Starting material | Product |
|---|---|---|---|
| Int-1c | 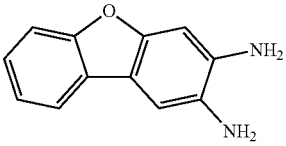 24258-73-9 | 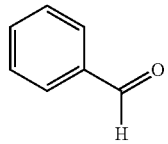 | 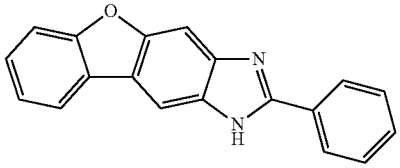 [SMILES: c1ccc(-c2nc3cc4oc5ccccc5c4cc3[nH]2)cc1] |
| Int-1d | 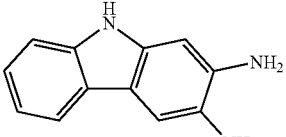 86439-50-1 | 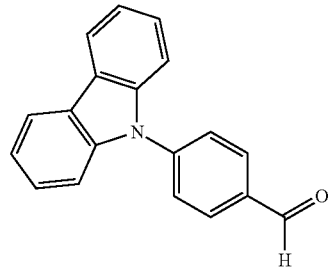 [SMILES: O=Cc1ccc(-n2c3ccccc3c3ccccc32)cc1] | 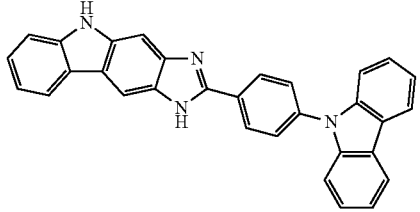 [SMILES: c1ccc2c(c1)[nH]c1cc3nc(-c4ccc(-n5c6ccccc6c6ccccc65)cc4)[nH]c3cc12] |
| Int-1e | 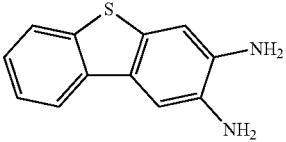 106020-19-3 | 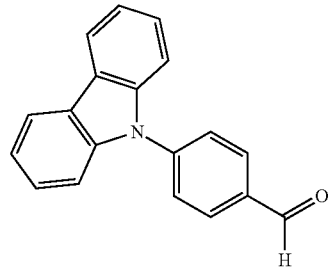 [SMILES: O=Cc1ccc(-n2c3ccccc3c3ccccc32)cc1] | 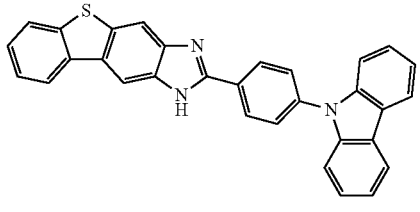 [SMILES: c1ccc2c(c1)sc1cc3nc(-c4ccc(-n5c6ccccc6c6ccccc65)cc4)[nH]c3cc12] |
| Ex. | Yield |
|---|---|
| Int-1b | 54% |
| Int-1c | 49% |
| Int-1d | 66% |
| Int-1e | 53% |
Synthesis of Compounds According to the Invention:
Example 2a
2-(4-Carbazol-9-ylphenyl)-3-(4,6-diphenylpyrimidin-2-yl)-3H-9-thia-1,3-diazacyclopenta[b]fluorene
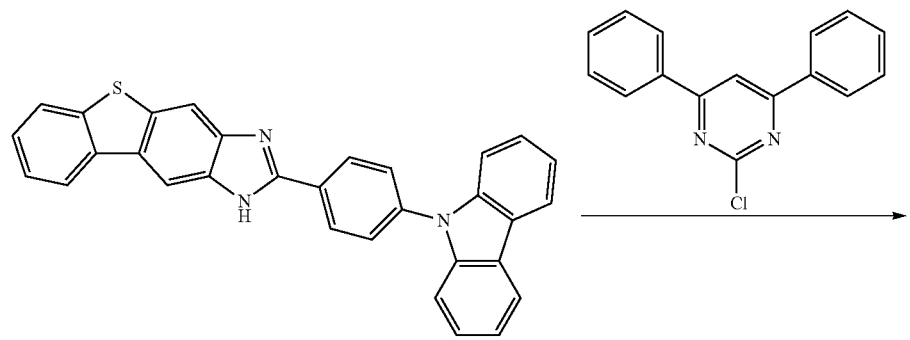

-continued

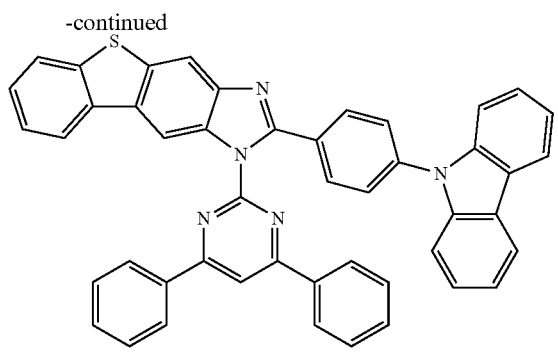

15

13.1 g (28.2 mmol) of 2-(4-carbazol-9-ylphenyl)-3H-9-thia-1,3-diazacyclopenta[b]fluorene are dissolved in 225 ml of dimethylformamide under protective-gas atmosphere, and 1.5 g of NaH, 60% in mineral oil, (37.5 mmol) are added. After 1 h at room temperature, a solution of 2-chloro-4,6-diphenyl-1,3,5-triazine (8.5 g, 31.75 mmol) in 75 ml of dimethylformamide is added dropwise. The reaction mixture is then stirred at room temperature for 12 h. After this time, the reaction mixture is poured onto ice and extracted three times with dichloromethane. The combined organic phases are dried over $Na_2SO_4$ and evaporated. The residue is extracted with hot toluene and recrystallised from toluene, finally sublimed in a high vacuum. The purity is 99.9%. The yield is 14.8 g (21 mmol, 80%).

The following compounds can be obtained analogously:

| Ex. | Starting material | Starting material | Product |
|---|---|---|---|
| 2b | | | |
| 2c | 857550-84-6 | | |

| Ex. | Yield |
|---|---|
| 2b | 58% |
| 2c | 67% |

The following compounds can be obtained analogously with 2 eq. of NaH and 2 eq. of 2-chloro-4,6-diphenyl-1,3,5-triazine:

| Ex. | Starting material | Starting material | Product |
|---|---|---|---|
| 2d | | | |
| 2e | | | |
| 2f | | (2 eq.) | |

| Ex. | Yield |
|---|---|
| 2d | 69% |
| 2e | 77% |
| 2f | 73% |

Example 3a

2-Phenyl-1-(9-phenyl-9H-carbazol-3-yl)-1H-benzo[4',5']-furo[2',3':4,5]benzo[1,2-d]imidazole

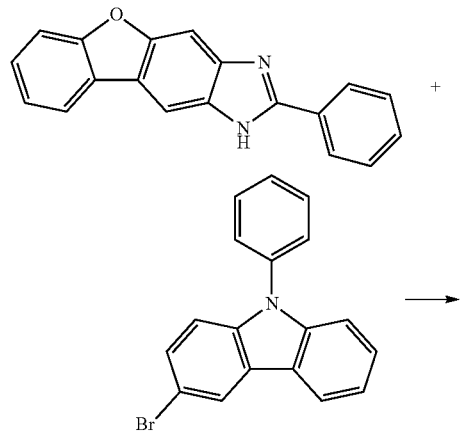

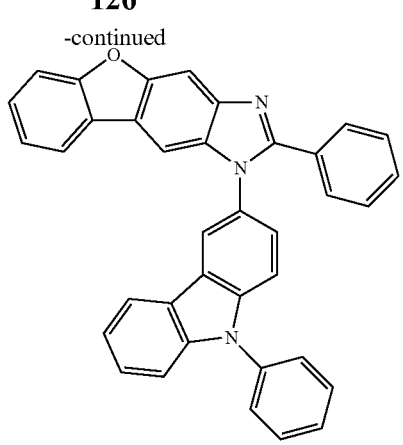

13.5 g (42.12 mmol) of 3-bromo-9-phenyl-9H-carbazole, 13.2 g (47 mmol) of 2-phenyl-1H-benzo[4',5']furo[2',3':4,5]benzo[1,2-d]imidazole and 29.2 g of $Rb_2CO_3$ are suspended in 250 ml of p-xylene. 0.95 g (4.2 mmol) of $Pd(OAc)_2$ and 12.6 ml of a 1M tri-tert-butylphosphine solution are added to this suspension. The reaction mixture is heated under reflux for 16 h. After cooling, the organic phase is separated off, washed three times with 200 ml of water and subsequently evaporated to dryness. The residue is extracted with hot toluene, recrystallised from toluene and finally sublimed in a high vacuum. The purity is 99.9%. Yield: 18 g (34 mmol), 76% of theory.

The following compounds can be obtained analogously:

| Ex. | Starting material | Starting material | Product |
|---|---|---|---|
| 3b | | 94994-62-4 | |
| 3c | | | |

-continued
| Ex. | Starting material | Starting material | Product |
|---|---|---|---|
| 3d | 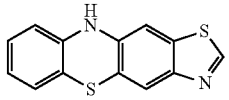 [SMILES: c1ccc2c(c1)Nc1cc3scnc3cc1S2] 21426-61-9 | 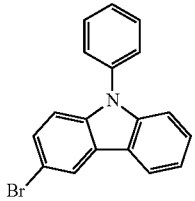 [SMILES: Brc1ccc2c(c1)c1ccccc1n2-c1ccccc1] | 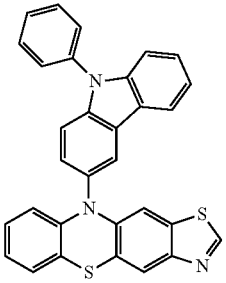 [SMILES: c1ccc(-n2c3ccccc3c3cc(N4c5ccccc5Sc5cc6ncsc6cc54)ccc32)cc1] |
| 3e | 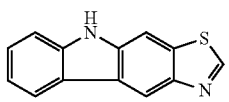 242-93-3 | 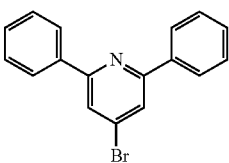 [SMILES: Brc1cc(-c2ccccc2)nc(-c2ccccc2)c1] 78500-89-7 | 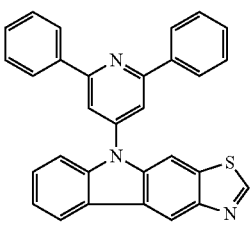 [SMILES: c1ccc(-c2cc(-n3c4ccccc4c4cc5ncsc5cc43)cc(-c3ccccc3)n2)cc1] |
| 3f | 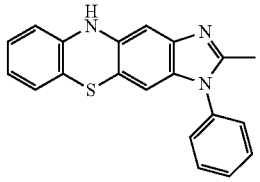 [SMILES: Cc1nc2cc3c(cc2n1-c1ccccc1)Sc1ccccc1N3] 823802-18-2 | 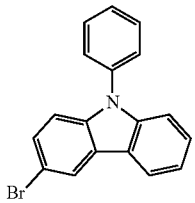 [SMILES: Brc1ccc2c(c1)c1ccccc1n2-c1ccccc1] | 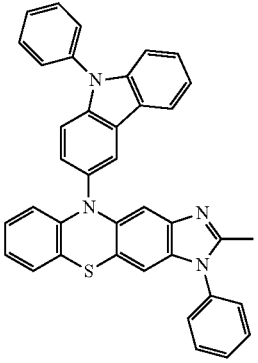 [SMILES: Cc1nc2cc3c(cc2n1-c1ccccc1)Sc1ccccc1N3c1ccc2c(c1)c1ccccc1n2-c1ccccc1] |
| 3g | 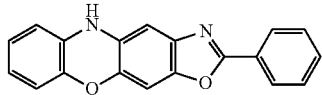 [SMILES: c1ccc(-c2nc3cc4c(cc3o2)Oc2ccccc2N4)cc1] 59225-35-3 | 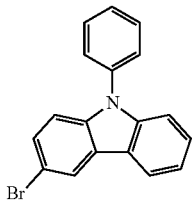 [SMILES: Brc1ccc2c(c1)c1ccccc1n2-c1ccccc1] | 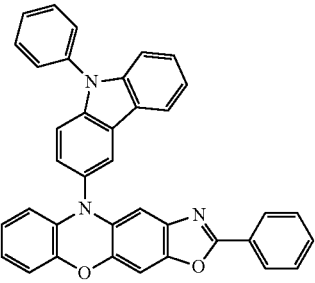 [SMILES: c1ccc(-c2nc3cc4c(cc3o2)Oc2ccccc2N4c2ccc3c(c2)c2ccccc2n3-c2ccccc2)cc1] |
| Ex. | Yield |
|---|---|
| 3b | 76% |
| 3c | 85% |
| 3d | 56% |
| 3e | 76% |
| 3f | 41% |
| 3g | 53% |

The following compounds can be obtained analogously with 2 eq. of 3-bromo-9-phenyl-9H-carbazole:

| Ex. | Starting material | Starting material | Product |
|---|---|---|---|
| 3h | | | |
| 3j | | | |

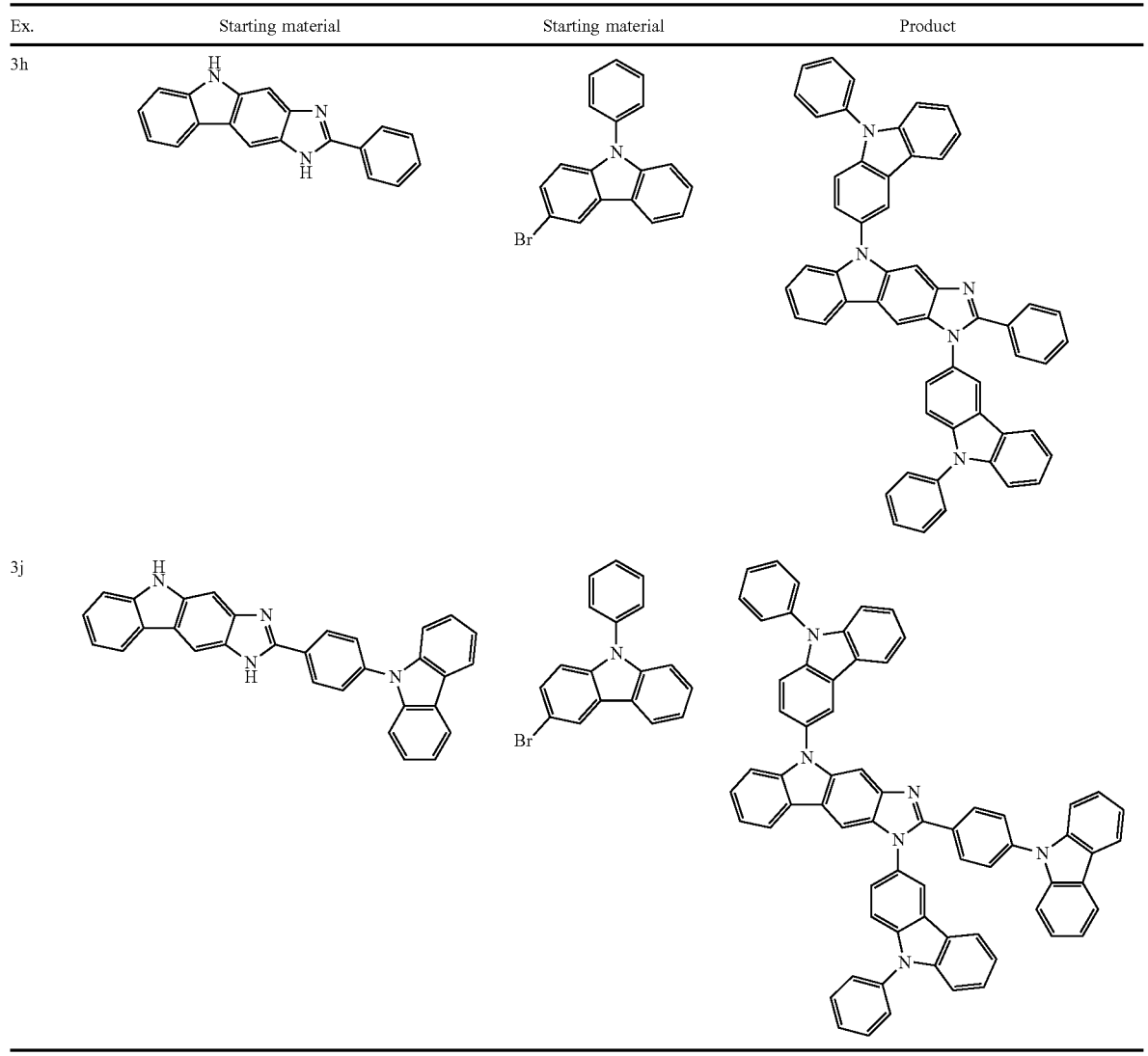

| Ex. | Yield |
|---|---|
| 3h | 64% |
| 3j | 55% |

Example 4a

2-Carbazol-9-yl-9-oxa-3-thia-1-azacyclopenta[b]fluorene

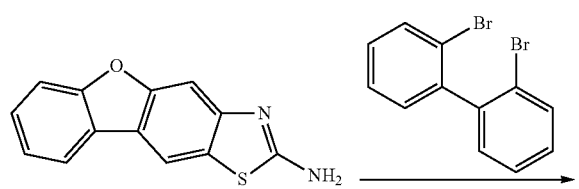

-continued

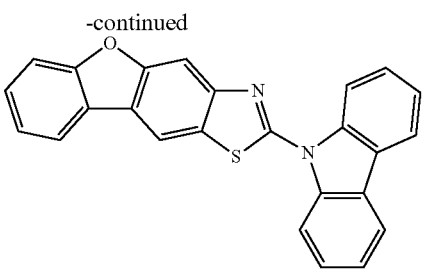

500 ml of toluene, 2.3 g (2.5 mmol) of tris(dibenzylideneacetone)dipalladium(0), 10 ml of 1M t-Bu₃P in toluene and sodium tert-butoxide 11.5 g (120 mmol) are added to 15.6 g (50 mmol) of 2,2 dibromo-1,1-biphenyl. 9.6 g (40 mmol) of 9-oxa-3-thia-1-azacyclopenta[b]fluoren-2-ylamine are subsequently added. The batch is heated at 110° C. for 20 h, then cooled to room temperature, and 400 ml of water are added. The mixture is extracted with ethyl acetate, the combined organic phases are then dried over sodium sulfate, and evaporated under reduced pressure. The residue is recrystallised from toluene and from dichloromethane/isopropanol. The yield is 8.5 g (22 mmol), corresponding to 55% of theory.

The following compounds can be obtained analogously:

B) Quantum-chemical Simulations of Compounds According to the Invention and Reference Materials The HOMO and LUMO positions and the triplet/singlet level of the organic compounds are determined via quantum-chemical calculations. To this end, the "Gaussian03W" program package (Gaussian Inc.) is used. In order to calculate organic substances without metals, firstly a geometry optimisation is carried out using a semi-empirical "Ground State/Semi-empirical/Default Spin/AM1" method (Charge 0/Spin Singlet). An energy calculation is subsequently carried out on the basis of the optimised geometry. In this, the "TD-SCF/DFT/Default Spin/B3PW91" method with the "6-31 G(d)" base set (Charge 0/Spin Singlet) is used. The most important results are HOMO/LUMO levels and energies for the triplet and singlet excited states. The first excited singlet state and the first excited triplet state are the most important and are called T1 and S1. The energy calculation gives the HOMO HEh or LUMO LEh in hartree units. The HOMO and LUMO values in electron volts are determined therefrom as follows, where these relationships arise from the calibration with reference to cyclic voltammetry measurements:

| Ex. | Starting material | Starting material | Product | Yield |
|---|---|---|---|---|
| 4b | 97339-25-8 | | | 61% |
| 4c | | | | 58% |

Other reference materials are:

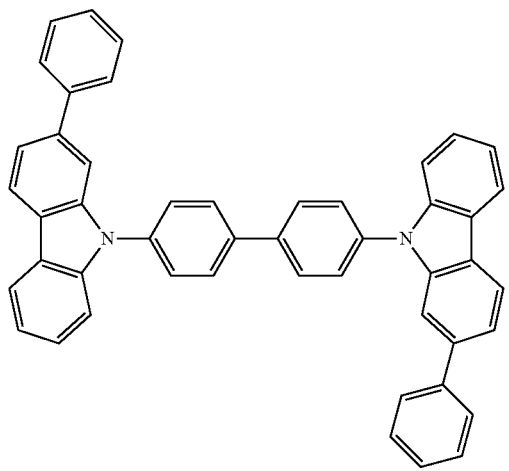

TMM1

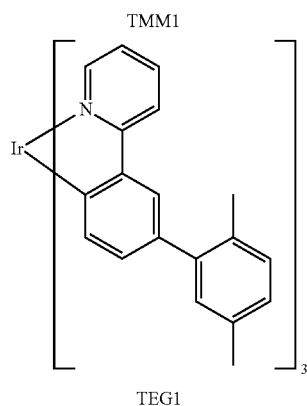

TEG1

$HOMO(eV)=((HEh*27.212)-0.9899)/1.1206$ $LUMO(eV)=((LEh*27.212)-2.0041)/1.385$

These values are to be regarded for the purposes of this application as the energetic position of the HOMO level or LUMO level of the materials. As an example, an HOMO of −0.20047 hartrees and an LUMO of −0.07772 hartrees are obtained from the calculation for compound 2a (see also Table 1), which corresponds to a calibrated HOMO of −5.75 eV and a calibrated LUMO of −2.97 eV.

The following examples show how compounds which are ideally suitable in each case can be identified by quantum-chemical calculations from compounds having the common basic structure according to the invention for the various uses in an OLED (as ETM, as HTM, as TMM).

TABLE 1

Summary of the energy levels of the compounds according to the invention and TMM1 as reference

|  | HOMO [eV] | LUMO [eV] | T1 [eV] | preferred uses |
|---|---|---|---|---|
| TMM1 | −5.68 | −2.39 | 2.84 | Matrix & ETM |
| 2a | −5.75 | −2.97 | 2.52 | ETM |
| 2b | −5.99 | −2.95 | 2.59 | Matrix & ETM |
| 2c | −6.02 | −2.98 | 2.66 | Matrix & ETM |
| 2d | −5.80 | −2.94 | 2.48 | ETM |
| 2e | −5.95 | −2.90 | 2.54 | ETM |
| 2f | −5.65 | −2.79 | 2.55 | ETM |
| 3a | −5.82 | −2.42 | 2.70 | Matrix |
| 3b | −5.87 | −2.49 | 2.70 | Matrix |
| 3c | −5.42 | −2.54 | 2.52 | HTM |
| 3d | −5.15 | −2.34 | 2.56 | Matrix & HTM |
| 3e | −5.97 | −2.48 | 2.86 | Matrix |
| 3f | −4.90 | −2.20 | 2.56 | Matrix & HTM |
| 3g | −5.20 | −2.55 | 2.26 | HTM |
| 3h | −5.30 | −2.30 | 2.67 | Matrix |
| 3j | −5.33 | −2.40 | 2.59 | Matrix &HTM |
| 4a | −5.96 | −2.60 | 2.70 | Matrix |
| 4b | −6.33 | −3.56 | 2.34 | ETM |
| 4c | −5.76 | −2.60 | 2.63 | Matrix |

The T1 level of TEG1 is 2.52 eV, which was derived from the onset of the photoluminescence spectrum of TEG1 in toluene. An optimum matrix material for TEG1 should therefore have a T1 level of >2.52 eV, preferably ≥2.57 eV. The compounds according to the invention from Table 1 in the case of which matrix is indicated under "preferred use" are therefore particularly suitable for this use.

For use as ETM, the compound should ideally have an LUMO <−2.6 eV, therefore the compounds according to the invention from Table 1 in the case of which ETM is indicated under "preferred use" are particularly suitable. And as HTM, the compound should preferably have an HOMO ≥−5.45 eV, therefore the compounds according to the invention from Table 1 in which HTM is indicated under "preferred use" are particularly suitable.

C) Device Examples

Preparation of Solutions and Compositions Comprising Matrix Materials and TEG1 for Use in OLEDs Solutions having the compositions in Table 2 are prepared as follows: firstly, 200 mg of the matrix material and 50 mg of TEG1 are dissolved in 10 ml of chlorobenzene and stirred until the solution is clear. The solution is filtered using a Millipore Millex LS, hydrophobic PTFE 5.0 μm filter.

TABLE 2

Composition of the solutions

|  | Composition | Ratio (based on weight) | Concentration |
|---|---|---|---|
| Solution Ref | TMM1 + TEG1 | 75%:25% | 25 mg/ml |
| Solution 1 | 2b + TEG1 | 75%:25% | 25 mg/ml |
| Solution 2 | 2c + TEG1 | 75%:25% | 25 mg/ml |
| Solution 3 | 3a + TEG1 | 75%:25% | 25 mg/ml |
| Solution 4 | 3b + TEG1 | 75%:25% | 25 mg/ml |
| Solution 5 | 3d + TEG1 | 75%:25% | 25 mg/ml |
| Solution 6 | 3e + TEG1 | 75%:25% | 25 mg/ml |
| Solution 7 | 3f + TEG1 | 75%:25% | 25 mg/ml |
| Solution 8 | 3h + TEG1 | 75%:25% | 25 mg/ml |
| Solution 9 | 3j + TEG1 | 75%:25% | 25 mg/ml |
| Solution 11 | 4a + TEG1 | 75%:25% | 25 mg/ml |
| Solution 12 | 4c + TEG1 | 75%:25% | 25 mg/ml |

The solutions are used in order to produce the emitting layer of OLEDs. The corresponding solid composition can be obtained by evaporating the solvent from the solutions. This can be used for the preparation of further formulations.

Production of the OLEDs

OLED-Ref to OLED12 having the structure ITO/PEDOT/interlayer/EML/cathode are produced in accordance with the following procedure using the corresponding solutions with the compositions in Table 2:

1) Coating of 80 nm of PEDOT (Clevios™ PVP AI 4083) to an ITO-coated glass substrate by spin coating, and drying by heating at 120° C. for 10 minutes.
2) Coating of a 20 nm interlayer by spin coating of a toluene solution of HIL-012 (Merck KGaA) (concentration 0.5% by weight) in a glove box.
3) Drying of the interlayer by heating at 180° C. for 1 h in a glove box.
4) Coating of an 80 nm emitting layer by spin coating of a corresponding solution in accordance with Table 2.
5) Drying of the device by heating at 180° C. for 10 min.
6) Application of a Ba/Al cathode by vapour deposition (3 nm+150 nm).
7) Encapsulation of the device.

Measurements and Comparison of the Results

The OLEDs obtained in this way are characterised by standard methods. The following properties are measured here: UIL characteristics, electroluminescence spectrum, colour coordinates, efficiency and operating voltage. The results are summarised in Table 3, where OLED-Ref serves as comparison in accordance with the prior art. In Table 3, $U_{on}$ stands for the use voltage, and U(100) stands for the voltage at 100 cd/m$^2$.

TABLE 3

Measurement results of the OLEDs according to the invention and the comparative examples

|  | Max. eff. [cd/A] | $U_{on}$ [V] | U(100) [V] | CIEx @ 100 cd/m$^2$ | CIEy @ 100 cd/m$^2$ |
|---|---|---|---|---|---|
| OLED-Ref | 8.2 | 3.8 | 6.5 | 0.33 | 0.62 |
| OLED1 | 26.1 | 3.1 | 4.9 | 0.34 | 0.62 |
| OLED2 | 24.5 | 2.5 | 3.6 | 0.33 | 0.62 |
| OLED3 | 16.4 | 3.0 | 4.9 | 0.34 | 0.63 |
| OLED4 | 14.6 | 3.1 | 5.2 | 0.34 | 0.62 |
| OLED5 | 13.4 | 3.1 | 4.9 | 0.33 | 0.62 |
| OLED6 | 14.3 | 3.3 | 5.4 | 0.34 | 0.62 |
| OLED7 | 10.4 | 2.8 | 4.4 | 0.30 | 0.58 |
| OLED8 | 12.9 | 2.5 | 3.6 | 0.33 | 0.62 |
| OLED9 | 14.7 | 3.3 | 5.4 | 0.34 | 0.62 |
| OLED11 | 23.0 | 2.8 | 4.3 | 0.34 | 0.62 |
| OLED12 | 27.0 | 2.7 | 3.8 | 0.33 | 0.62 |

As can be seen from Table 3, significantly improved phosphorescent OLEDs with respect to operating voltage and efficiency are in all cases obtained on use of the compounds according to the invention as matrix materials. All OLEDs exhibit comparable colour coordinates.

The technical effects observed are not restricted to the system shown. They can also be achieved, for example, using other phosphorescent emitters and on use of additional co-matrices.

The invention claimed is:

1. An electronic device comprising an anode, a cathode, and at least one organic layer comprising at least one compound of formula (I):

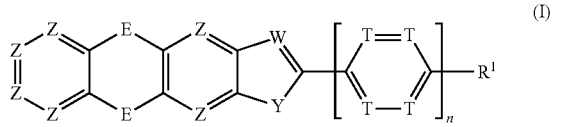

(I)

wherein

E is selected on each occurrence, identically or differently, from a single bond, $B(R^1)$, $C=O$, $N(R^1)$, $P(R^1)$, $P(=O)R^1$, O, S, $S=O$, and $S(=O)_2$, wherein both groups E cannot be a single bond;

T is on each occurrence, identically or differently, $CR^1$ or N;

W is N;

Y is $N(R^1)$, O, or S;

Z is on each occurrence, identically or differently, $CR^2$ or N;

$R^1$ is on each occurrence, identically or differently, H, D, F, $C(=O)R^3$, CN, $Si(R^3)_3$, $N(R^3)_2$, $P(=O)(R^3)_2$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein said groups are optionally substituted by one or more radicals $R^3$, wherein one or more $CH_2$ groups in said groups are optionally replaced by $C=NR3$, $C(=O)O$ —$R^3C=CR^3$—, —$C\equiv C$—, $Si(R^3)_2$, $C=O$, —$C(=O)NR^3$—, $NR^3$, $P(=O)(R^3)$, —O—, —S—, SO, or $SO_2$, and wherein one or more H atoms in said groups are optionally replaced by D, F, or CN, an aromatic or heteroaromatic ring system having 5 to 30 aromatic ring atoms optionally substituted by one or more radicals $R^3$, or an aryloxy or heteroaryloxy group having 5 to 30 aromatic ring atoms optionally substituted by one or more radicals $R^3$;

$R^2$ is on each occurrence, identically or differently, H, D, F, $C(=O)R^3$, CN, $Si(R^3)_3$, $N(R^3)_2$, $P(=O)(R^3)_2$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein said groups are optionally substituted by one or more radicals $R^3$, wherein one or more $CH_2$ groups in said groups are optionally replaced by —$R^3C=CR^3$—, —$C\equiv C$—, $Si(R^3)_2$, $C=O$, $C=NR^3$, —$C(=O)O$—, —$C(=O)NR^3$—, $NR^3$, $P(=O)(R^3)$, —O—, —S—, SO, or $SO_2$, and wherein one or more H atoms in said groups are optionally replaced by D, F, or CN, an aromatic or heteroaromatic ring system having 5 to 30 aromatic ring atoms optionally substituted by one or more radicals $R^3$, or an aryloxy or heteroaryloxy group having 5 to 30 aromatic ring atoms optionally substituted by one or more radicals $R^3$, and wherein two or more radicals $R^2$ are optionally linked to one another and optionally define an aliphatic or heteroaliphatic ring;

$R^3$ is on each occurrence, identically or differently, H, D, F, $C(=O)R^4$, CN, $Si(R^4)_3$, $N(R^4)_2$, $P(=O)(R^4)_2$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein said groups are optionally substituted by one or more radicals $R^4$, wherein one or more $CH_2$ groups in said groups are optionally replaced by —$R^4C=CR^4$—, —$C\equiv C$—, $Si(R^4)_2$, $C=O$, $C=NR^4$, —$C(=O)O$—, —$C(=O)NR^4$—, $NR^4$, $P(=O)(R^4)$, —O—, —S—, SO, or $SO_2$, and wherein one or more H atoms in said groups are optionally replaced by D, F, or CN, an aromatic or heteroaromatic ring system having 5 to 30 aromatic ring atoms optionally substituted by one or more radicals $R^4$, or an aryloxy or heteroaryloxy group having 5 to 30 aromatic ring atoms optionally substituted by one or more radicals $R^4$, and wherein two or more radicals $R^3$ are optionally linked to one another and optionally define a ring;

$R^4$ is on each occurrence, identically or differently, H, D, F, or an aliphatic, aromatic, or heteroaromatic organic radical having 1 to 20 C atoms, wherein one or more H atoms are optionally replaced by D or F; and wherein two or more substituents $R^4$ are optionally linked to one another and optionally define a ring;

n is 0 or 1;

wherein at least one group $R^1$ or $R^2$ in the compound of formula (I) is selected from an aromatic or heteroaromatic ring system having 5 to 40 aromatic ring atoms optionally substituted by one or more radicals $R^3$.

2. The electronic device of claim 1, wherein at least one group $R^1$ or $R^2$ in the compound of formula (I) is selected from a group comprising at least one of the following groups:

heteroaryl groups having 5 to 20 aromatic ring atoms which comprise at least one heteroaromatic five-membered ring having two or more heteroatoms selected from the group consisting of N, O, and S;

heteroaryl groups having 6 to 20 aromatic ring atoms which comprise at least one heteroaromatic six-membered ring having one or more heteroatoms selected from the group consisting of N, O, and S; and carbazole groups.

3. The electronic device of claim 1, wherein at least one group $R^1$ or $R^2$ in the compound of formula (I) is selected from groups of formulae (Het-a) to (Het-e):

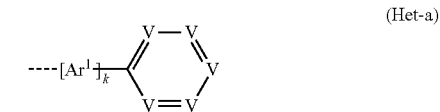
(Het-a)

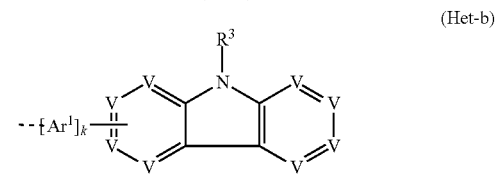
(Het-b)

(Het-c)

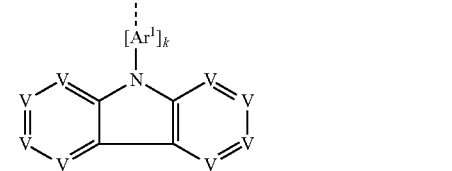

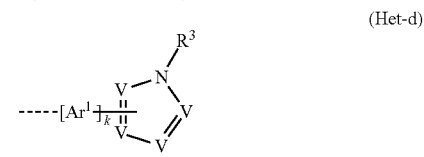
(Het-d)

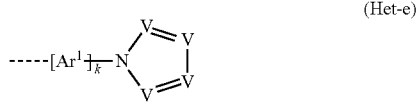

(Het-e)

wherein

Ar¹ is an aromatic or heteroaromatic ring system having 5 to 20 aromatic ring atoms optionally substituted by one or more radicals $R^3$;

V is on each occurrence, identically or differently, N or $CR^3$;

k is 0 or 1;

the dashed line denotes the bond to the remainder of the compound; and wherein at least one group V in the ring in formula (Het-a), (Het-d), and (Het-e) is N.

4. The electronic device of claim 1, wherein n is 1.

5. The electronic device of claim 1, wherein all Z are $CR^2$.

6. The electronic device of claim 1, wherein E is on each occurrence, identically or differently, a single bond, C=O, $N(R^1)$, O, S, S=O, or $S(=O)_2$, wherein both groups E cannot be a single bond.

7. The electronic device of claim 1, wherein said electronic device is selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices.

8. The electronic device of claim 1, wherein said electronic device comprises the compound of formula (I) in an electron-transport layer or comprises the compound of formula (I) in an emitting layer as matrix material in combination with one or more dopants.

9. A compound of formula (I-1):

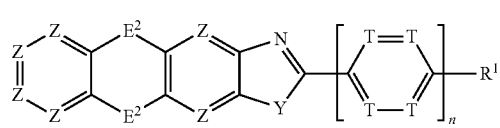

(I-1)

wherein $E^2$ is on each occurrence, identically or differently, a single bond, C=O, $N(R^1)$, O, or S, wherein both groups $E^2$ cannot be a single bond;

T is on each occurrence, identically or differently, $CR^1$ or N;

Y is $N(R^1)$, O, or S;

Z is on each occurrence, identically or differently, $CR^2$ or N;

$R^1$ is on each occurrence, identically or differently, H, D, F, $C(=O)R^3$, CN, $Si(R^3)_3$, $N(R^3)_2$, $P(=O)(R^3)_2$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein said groups are optionally substituted by one or more radicals $R^3$, wherein one or more $CH_2$ groups in said groups are optionally replaced by $-R^3C=CR^3-$, $-C\equiv C-$, $Si(R^3)_2$, C=O, $C=NR^3$, $-C(=O)O-$, $-C(=O)NR^3-$, $NR^3$, $P(=O)(R^3)$, $-O-$, $-S-$, SO, or $SO_2$, and wherein one or more H atoms in said groups are optionally replaced by D, F, or CN, an aromatic or heteroaromatic ring system having 5 to 30 aromatic ring atoms optionally substituted by one or more radicals $R^3$, or an aryloxy or heteroaryloxy group having 5 to 30 aromatic ring atoms optionally substituted by one or more radicals $R^3$;

$R^2$ is on each occurrence, identically or differently, H, D, F, $C(=O)R^3$, CN, $Si(R^3)_3$, $N(R^3)_2$, $P(=O)(R^3)_2$, $S(=O)R^3$, $S(=O)_2R^3$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein said groups are optionally substituted by one or more radicals $R^3$, wherein one or more $CH_2$ groups in said groups are optionally replaced by $-R^3C=CR^3-$, $-C\equiv C-$, $Si(R^3)_2$, C=O, $C=NR^3$, $-C(=O)O-$, $-C(=O)NR^3-$, $NR^3$, $P(=O)(R^3)$, $-O-$, $-S-$, SO, or $SO_2$, and wherein one or more H atoms in said groups are optionally replaced by D, F, or CN, an aromatic or heteroaromatic ring system having 5 to 30 aromatic ring atoms optionally substituted by one or more radicals $R^3$, or an aryloxy or heteroaryloxy group having 5 to 30 aromatic ring atoms optionally substituted by one or more radicals $R^3$, and wherein two or more radicals $R^2$ are optionally linked to one another and optionally define an aliphatic or heteroaliphatic ring;

$R^3$ is on each occurrence, identically or differently, H, D, F, $C(=O)R^4$, CN, $Si(R^4)_3$, $N(R^4)_2$, $P(=O)(R^4)_2$, $S(=O)R^4$, $S(=O)_2R^4$, a straight-chain alkyl or alkoxy group having 1 to 20 C atoms or a branched or cyclic alkyl or alkoxy group having 3 to 20 C atoms or an alkenyl or alkynyl group having 2 to 20 C atoms, wherein said groups are optionally substituted by one or more radicals $R^4$, wherein one or more $CH_2$ groups in said groups are optionally replaced by $-R^4C=CR^4-$, $-C\equiv C-$, $Si(R^4)_2$, C=O, $C=NR^4$, $-C(=O)O-$, $-C(=O)NR^4-$, $NR^4$, $P(=O)(R^4)$, $-O-$, $-S-$, SO, or $SO_2$, and wherein one or more H atoms in said groups are optionally replaced by D, F, or CN, an aromatic or heteroaromatic ring system having 5 to 30 aromatic ring atoms optionally substituted by one or more radicals $R^4$, or an aryloxy or heteroaryloxy group having 5 to 30 aromatic ring atoms optionally substituted by one or more radicals $R^4$, and wherein two or more radicals $R^3$ are optionally linked to one another and optionally define a ring;

$R^4$ is on each occurrence, identically or differently, H, D, F, or an aliphatic, aromatic, or heteroaromatic organic radical having 1 to 20 C atoms, wherein one or more H atoms are optionally replaced by D or F; and wherein two or more substituents $R^4$ are optionally linked to one another and optionally define a ring;

n is 0 or 1;

wherein at least one group $R^1$ or $R^2$ in the compound of formula (I) is selected from an aromatic or heteroaromatic ring system having 5 to 40 aromatic ring atoms optionally substituted by one or more radicals $R^3$; and wherein at least one group $R^1$ is selected from groups of formulae (Het-a) to (Het-e):

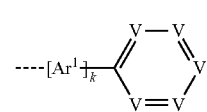

(Het-a)

-continued

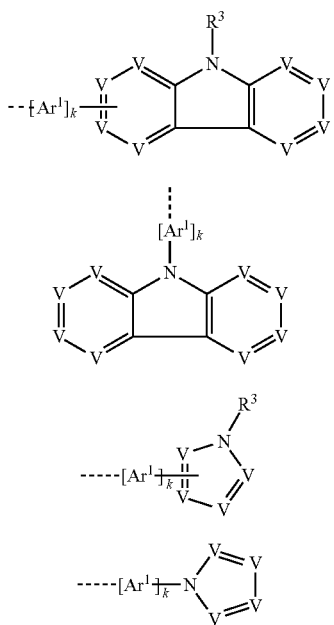

wherein

Ar$^1$ is an aromatic or heteroaromatic ring system having 5 to 20 aromatic ring atoms optionally substituted by one or more radicals R$^3$;

V is on each occurrence, identically or differently, N or CR$^3$;

k is 0 or 1;

the dashed line denotes the bond to the remainder of the compound; and wherein at least one group V in the ring in formula (Het-a), (Het-d), and (Het-e) is N.

10. The compound of claim 9, wherein Y is NR$^1$.

11. The compound of claim 9, wherein E$^2$ is on each occurrence, identically or differently, a single bond, NR$^1$, O, or S, wherein both groups E$^2$ cannot be a single bond.

12. An oligomer, polymer, or dendrimer comprising one or more compounds of claim 9, wherein the bond(s) to the polymer, oligomer, or dendrimer are optionally localised at any positions in formula (I-1) substituted by R$^1$ or R$^2$.

13. A formulation comprising at least one polymer, oligomer, or dendrimer of claim 12 and at least one solvent.

14. A formulation comprising at least one compound of claim 9 and at least one solvent.

* * * * *